United States Patent
Zhang et al.

(10) Patent No.: US 10,494,332 B2
(45) Date of Patent: *Dec. 3, 2019

(54) PROTEIN TYROSINE PHOSPHATASES OR SHP2 INHIBITORS AND USES THEREOF

(71) Applicant: Indiana University Research and Technology Corporation, Indianapolis, IN (US)

(72) Inventors: Zhong-Yin Zhang, West Lafayette, IN (US); Rongjun He, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/577,417

(22) PCT Filed: Jun. 1, 2016

(86) PCT No.: PCT/US2016/035212
§ 371 (c)(1),
(2) Date: Nov. 28, 2017

(87) PCT Pub. No.: WO2016/196591
PCT Pub. Date: Dec. 8, 2016

(65) Prior Publication Data
US 2018/0170862 A1    Jun. 21, 2018

Related U.S. Application Data

(60) Provisional application No. 62/169,148, filed on Jun. 1, 2015, provisional application No. 62/169,122, filed on Jun. 1, 2015.

(51) Int. Cl.
| | | |
|---|---|---|
| C07C 317/02 | (2006.01) | |
| C07C 317/08 | (2006.01) | |
| C07C 317/18 | (2006.01) | |
| C07D 211/14 | (2006.01) | |
| C07D 215/00 | (2006.01) | |
| C07D 209/04 | (2006.01) | |
| C07D 307/52 | (2006.01) | |
| C07C 309/24 | (2006.01) | |
| A61K 45/06 | (2006.01) | |
| C07C 309/17 | (2006.01) | |
| A61P 25/28 | (2006.01) | |
| A61P 3/10 | (2006.01) | |
| A61P 31/06 | (2006.01) | |
| A61P 35/00 | (2006.01) | |
| C07D 211/16 | (2006.01) | |
| C07D 211/18 | (2006.01) | |
| C07D 215/08 | (2006.01) | |
| C07D 231/40 | (2006.01) | |
| C07D 233/64 | (2006.01) | |
| C07D 235/10 | (2006.01) | |
| C07D 235/14 | (2006.01) | |
| C07D 277/46 | (2006.01) | |
| C07D 277/82 | (2006.01) | |
| C07D 285/135 | (2006.01) | |
| C07D 307/68 | (2006.01) | |
| C07D 333/20 | (2006.01) | |

(Continued)

(52) U.S. Cl.
CPC ............ *C07C 309/24* (2013.01); *A61K 45/06* (2013.01); *A61P 3/10* (2018.01); *A61P 25/28* (2018.01); *A61P 31/06* (2018.01); *A61P 35/00* (2018.01); *A61P 35/02* (2018.01); *C07C 309/17* (2013.01); *C07C 309/18* (2013.01); *C07D 211/16* (2013.01); *C07D 211/18* (2013.01); *C07D 215/08* (2013.01); *C07D 215/38* (2013.01); *C07D 231/40* (2013.01); *C07D 233/61* (2013.01); *C07D 233/64* (2013.01); *C07D 235/10* (2013.01); *C07D 235/14* (2013.01); *C07D 277/46* (2013.01); *C07D 277/82* (2013.01); *C07D 285/135* (2013.01); *C07D 295/135* (2013.01); *C07D 307/68* (2013.01); *C07D 333/20* (2013.01)

(58) Field of Classification Search
CPC ... C07C 317/02; C07C 317/08; C07C 317/18; C07D 211/14; C07D 215/00; C07D 209/04; C07D 307/52
See application file for complete search history.

(56) References Cited

U.S. PATENT DOCUMENTS

| | | |
|---|---|---|
| 2005/0124590 A1 | 6/2005 | Kuwada |
| 2006/0141632 A1 | 6/2006 | Keough et al. |
| 2014/0186467 A1 | 7/2014 | Diggs et al. |

FOREIGN PATENT DOCUMENTS

| | | |
|---|---|---|
| WO | 2014035961 A1 | 3/2014 |
| WO | 2014080251 A1 | 5/2014 |

OTHER PUBLICATIONS

Chen et al., Identification and Characterization of Novel Inhibitors of mPTPB, an Essential Virulent Phosphatase from *Mycobacterium tuberculosis*, ACS Med. Chem. Lett. 2010, vol. 1, pp. 355-359.

(Continued)

*Primary Examiner* — Bruck Kifle
(74) *Attorney, Agent, or Firm* — Faegre Baker Daniels LLP

(57) ABSTRACT

Small molecule compounds derived from α-sulfophenylacetic amide (SPAA) are provided as novel sulfonic acid based pTyr mimetics. These compounds effectively inhibit a variety of protein tyrosine phosphatases (PTPs), such as mPTPA, mPTPB, LMWPTP, and Laforin. Use of these compounds as pharmaceutical agents for treating diseases associated with abnormal protein tyrosine phosphatase activity is also provided.

9 Claims, 34 Drawing Sheets

(51) Int. Cl.
    *A61P 35/02*     (2006.01)
    *C07C 309/18*     (2006.01)
    *C07D 215/38*     (2006.01)
    *C07D 233/61*     (2006.01)
    *C07D 295/135*     (2006.01)

(56) References Cited

OTHER PUBLICATIONS

Combs A. P., Structure-Based Design and Discovery of Protein Tyrosine Phosphatase Inhibitors Incorporating Novel Isothiazolidinone Heterocyclic Phosphotyrosine Mimetics, J. Med. Chem. 2010, vol. 53, pp. 2333-2344.

Correa et al., Identification of Inhibitors for Mycobacterial Protein Tyrosine Phosphatase B (MptpB) by Biology-Oriented Synthesis (BIOS), Chem. Asian J. 2007, vol. 2, No. 9, pp. 1109-1126.

Gandhi et al., Mulitdrug-resistant and extensively drug-resistant tuberculosis: a threat to global control of tuberculosis; Lancet, 2010, vol. 375, pp. 1830-1843.

Grundner et al., Structural Basis for Selective Inhibition of *Mycobacterium tuberculosis* Protein Tyrosine Phosphatase PtpB; Stucture, 2007, vol. 15, No. 4, pp. 499-509.

Harries et al., Tuberculosis 3; The HIV-associated tuberculosis epidemic—when will we act?; Lancet, 2010, vol. 375, pp. 1906-1919.

Marals et al., Tuberculosis 8; Scale-up of services and research priorities for diagnosis, management, and control of tuberculosis: a call to action; Lancet, 2010, vol. 375, pp. 2179-2191.

Noren-Muller et al., Discovery of protein phosphatase inhibitor classes by biology-oriented synthesis; PNAS, 2006, vol. 103, No. 28, pp. 10606-10611.

Noren-Muller et al., Discovery of a new class of inhibitors of *Mycobacterium tuberculosis* protein tyrosine phosphatase B by biology-oriented synthesis., Angew. Chem. Int. Ed. 2008, vol. 47, pp. 5973-5977.

PubChem: Open Chemistry Database; US20060141632A1-20060629-C00007_1; SID 139195423.

PubChem: Open Chemistry Database; SCHEMBL9236764; SID 234661969.

Rawls et al., Fragment-based discovery of selective inhibitors of the *Mycobacterium tuberculosis* protein tyrosine phosphatase PtpA; Bioorg Med Chem Lett., 2009, vol. 19, No. 24, pp. 6851-6854.

Soellner et al., Fragment-Based Substrate Activity Screening Method for the Identification of Potent Inhibitors of the *Mycobacterium tuberculosis* Phosphatase PtpB, J. Am. Chem. Soc. 2007, vol. 129, pp. 9613-9615.

Tan et al., High-Throughput Discovery of *Mycobacterium tuberculosis* Protein Tyrosine Phosphatase B (MptpB) Inhibitors Using Click Chemistry, Org. Lett. 2009, vol. 11, pp. 5102-5105.

Trott et al., AutoDock Vina: improving the speed and accuracy of docketing with a new scoring function, efficient optimization and multithreading; J Comput Chem., 2010, vol. 31, No. 2, pp. 455-461.

Vagin et al., MOLREP: an Automated Program for Molecular Replacement, Appl. Crystallogr. 1997, vol. 30, pp. 1022-1025.

Vintonyak et al., Identification of thiazolidinones spiro-fused to indolin-2-ones as potent and selective inhibitors of the *Mycobacterium tuberculosis* protein tyrosine phosphatase B., Angew. Chem. Int. Ed. 2010, vol. 49, pp. 5902-5905.

World Health Organization; WHO 2010 (Global Tuberculosis Control 2010); 218 pages.

Weide et al, 3-Substituted Indolizine-1-carbonitrile Derivatives as Phosphatase Inhibitors; Bioorg. Med.Chem. Lett. 2006, vol. 16, pp. 59-63.

Zhou et al., Targeting *Mycobacterium* protein tyrosine phosphatase B for antituberculosis agents; PNAS, 2010, vol. 107, No. 10, pp. 4573-4578.

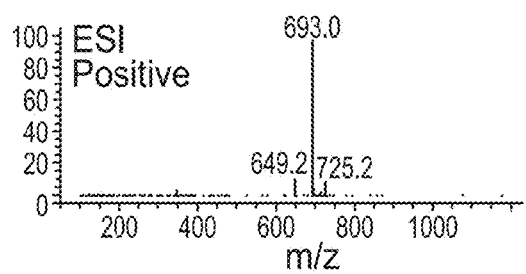
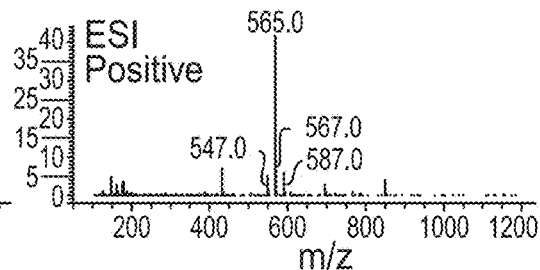
FIG. 22A
FIG. 22B
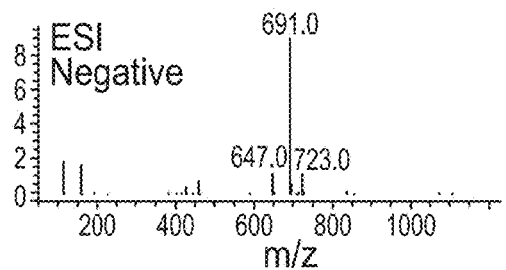
Exact Mass: 692.2
Molecular Weight: 692.8
FIG. 22C
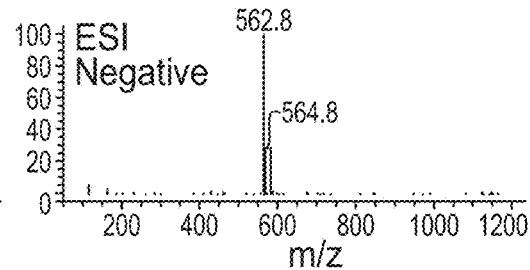
Exact Mass: 564.0
Molecular Weight: 564.7
FIG. 22D

PROTEIN TYROSINE PHOSPHATASES OR SHP2 INHIBITORS AND USES THEREOF

CROSS REFERENCE TO RELATED APPLICATIONS

This application claims priority to International Application Number PCT/US2016/035212, filed on 1 Jun. 2016, which claims priority to U.S. Provisional Application Ser. No. 62/169,148 filed Jun. 1, 2015 and U.S. Provisional Application Ser. No. 62/169,122, filed Jun. 1, 2015, each of which are hereby incorporated by reference in their entireties.

STATEMENT REGARDING FEDERALLY SPONSORED RESEARCH & DEVELOPMENT

This invention was made with government support under CA152194 awarded by the National Institutes of Health. The government has certain rights in the invention.

BACKGROUND OF THE DISCLOSURE

The field of the disclosure relates generally to small molecule inhibitors of protein tyrosine phosphatases (PTPs). Protein tyrosine phosphorylation is a key post-translational modification used by eukaryotic organisms to control protein function. Proper levels of tyrosine phosphorylation are maintained by protein tyrosine kinases (PTKs) and protein tyrosine phosphatases (PTPs). Disturbance of the coordinated and opposing activities of PTKs and PTPs leads to aberrant tyrosine phosphorylation, which is associated with the development and pathogenesis of numerous human diseases including cancer, diabetes and autoimmune disorders. Accordingly, dysfunctional tyrosine phosphorylation mediated signaling networks present enormous opportunities for therapeutic intervention. This has prompted the development of inhibitors for disease-associated PTKs, over two-dozen of which have already been approved for clinical use.

For example, mPTPB, a virulence factor of the *Mycobacterium tuberculosis* (Mtb) strain, is a novel drug target of tuberculosis (TB). Tuberculosis continues to be a leading epidemic in the world which kills approximately 2 million and infects 9 million people annually (WHO Report, 2010 on Global TB Control, 2010). The present short course chemo therapy, formulated 40 years ago, starts with administration of isoniazid, pyrazinamide, and rifampicin for two months, and then isoniazid or rifampicin for four months, which is time-consuming, tedious and costly. The emergence of multidrug-resistant (MDR), extensively resistant (XDR), and HIV-associated TB has also severally challenged current therapies (Harries et al., Lancet 2010, 375, 1906-1919; Gandhi et al., Lancet 2010, 375, 1830-1843). With the currently available approaches, it is impossible to eliminate the TB disease as a worldwide threat by reducing incidence below one case per million populations by 2050, a long term target of Millennium Development Goals (Marais et al., Lancet 2010, 375, 2179-2191). In this regard, molecules targeting mPTPB provide a solution for these challenges.

mPTPA is another PTP (17.5 kDa) secreted by the Mtb strain, which has 38% sequence and large overall structural similarities with human low molecular weight PTPs (LMPTP). It has been found that the expression level of mPTPA in *M. bovis* BCG increased upon entry into stationary phase in vitro or upon infection of human monocytes, implying a positive role of this enzyme during infections. mPTPA is also capable of inhibiting phagocytosis and increasing actin polymerizations in macrophages. Human mPTPA, when combined with its substrate (VPS33B), inhibits phagosome-lysosome fusion, a process arrested in Mtb's infection. A genetic deletion of mPTPA attenuated Mtb growth in human macrophages. These findings indicate that mPTPA is another potential target for the development of novel anti-TB agents, in addition to mPTPB. So far, only few mPTPA inhibitors have been reported, and most of them lack potency and specificity over human PTPs. The compound developed by Ellman (Rawls et al., Bioorg. Med. Chem. Lett. 2009, 19, 6851-6854) based on phosphonodifluoromethyl phenylalanine (F2PMP) as a phosphotyrosine (pTyr) mimetic, with a Ki value at 1.4 µM, is 11-fold selective for mPTPA over LMPTP, and is 70-fold selective for several mammalian PTPs such as PTP1B, TcPTP, CD45.

LMWPTP is a positive regulator of tumor onset and progression probably by dephosphorylating ephrin A2 (EphA2) receptor tyrosine kinase. Clinically, elevated LMWPTP mRNA and protein level have been observed in malignant samples of breast, colon, bladder, and kidney. LMWPTP is also a key negative regulator of insulin signaling, and inhibition of LMWPTP (e.g. by antisense oligonucleotide (ASO) in cultured mouse hepatocytes, liver and fat tissues of diet-induced obese (DIO) mice and ob/ob mice) leads to increased phosphorylation and activity of key insulin signaling intermediates, including insulin receptor-β subunit, phosphatidylinositol 3-kinase, and Akt. Recently, LMWPTP is shown to be a good drug target for cancer and type 2 diabetes Accordingly, small molecule inhibitors of LMWPTP are potential treatments for cancer, insulin resistance, type 2 diabetes and obesity. Unfortunately, the development of LMWPTP inhibitors has met with little success. Moderately active LMWPTP inhibitors have been reported, but these compounds also inhibit other PTPS, such as PTP1B, TcPTP, PTPβ.

Laforin is a dual specificity phosphatase encoded by the EPM2A gene, the mutation of which has been found in patients with Lafora disease, a fatal autosomal recessive genetic disorder characterized by the existence of inclusion bodies (Lafora bodies) in neurons, heart, liver, muscle, and skin. Patients with this disease usually die within 10 years of showing symptoms and do not live beyond the age of 25. Currently there is no cure for the disease. It is proposed that this disease is caused by the mutation in Laforin's carbohydrate binding domain (CBD), making Laforin unable to locate its substrate and eventually leading to the formation of insoluble polyglucocans, the main component of Lafora bodies. Remarkably, whether PTP activity is involved in the development of Lafora disease is one of the open questions in the field, and a specific Laforin inhibitor can provide useful insight.

Further, the Src homology 2 (SH2) domain containing protein tyrosine phosphatase-2 (SHP2), encoded by the PTPN11 gene, has generated considerable interest as an oncology target. Biochemically, SHP2 serves as a positive signal-transducer downstream of most, if not all, receptor PTKs and is required for Ras-ERK1/2 cascade activation. Consistent with its oncogenic potential, germline gain-of-function mutations in PTPN11 cause Noonan syndrome, whereas somatic activating PTPN11 mutations occur in juvenile and adult myeloproliferative diseases and contribute to several types of solid tumors including lung adenocarcinoma, colon and prostate cancer, neuroblastoma, glioblastoma, melanoma, and hepatocellular carcinoma. SHP2 is also shown to play a critical role in both triple-negative and HER2+ breast cancer. Finally, given the essential role of SHP2 in growth factor signaling, thwarting SHP2 action may also prove effective for cancers caused by abnormal activation of receptor PTKs. These findings have spurred an intense effort to develop SHP2 inhibitors for novel anticancer agents.

Small molecule inhibitors of PTP are invaluable in elucidating the mechanisms of these diseases and in providing novel therapeutic interventions. However, as discussed above, the development in this area has been largely hurdled by the challenges of developing potent, selective and bioavailable, or simple drug-like PTP inhibitors. The underlying reasons are that more than 100 PTPs identified to date utilize a common catalytic mechanism, and that their highly positively charged active sites share a high level of similarity. Targeting an active site with negatively charged phosphotyrosine (pTyr) substrate mimetics, and surrounding regions with additional fragments is a major strategy having a certain degree of success. pTyr mimetics play a vital role in this regard, and serve as foundations for the development of potent and specific PTP inhibitors. This is well demonstrated by F2PMP, a non-hydrolyzable pTyr mimetic designed nearly two decades ago that led to the discovery of many PTP1B inhibitors to date (FIG. 1).

Carboxylic acid is another typical class of pTyr mimetic that has been studied extensively. Specifically, salicylic acid is a novel, cell permeable pTyr mimetic discovered recently, from which specific inhibitors against LYP, SHP2, and mPTPB have been developed. Consequently, one would consider sulfonic acids as pTyr mimetics in addition to phosphonic and carboxylic acids. Unfortunately, research in this subject had obtained very limited success, with scarce reports on several moderately active and nonspecific PTP inhibitors.

Accordingly, there is a need in the art to provide small molecule inhibitors of PTPs, and more particularly, there is a need for highly potent and specific bioavailable inhibitors of several distinct FTPs, including mPTPA, mPTPB, LMW-FPTP, Laforin, SHP2, LYP, and HePTP.

SUMMARY OF THE DISCLOSURE

The present disclosure generally relates to small molecule inhibitors of PTPs and the use of these inhibitors as therapeutics for various diseases associated with abnormal protein tyrosine phosphatase activity.

In one aspect, the present disclosure provides a compound of Formula 1b:

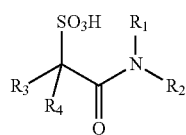

Formula 1b or a therapeutically suitable prodrug thereof or a therapeutically suitable salt thereof, wherein $R_1$ is hydrogen and $R_2$ is aryl or heteroaryl and is substituted with $—(CH_2)_s—NH—CO—R_z$;
wherein s is 0-4;
wherein $R_z$ is aryl or heteroaryl, and the aryl or heteroaryl are independently optionally substituted with one or more substituent selected from the group consisting of $C_1$-$C_4$ alkyl, benzoyl, benzyl, benzyloxy (—OBn), phenyl, halogen, 1H-benzimidazole-2-yl, and 2-thiophenyl;
or wherein $R_1$, $R_2$, and the N atom to which they are attached are joined together to form a monocyclic or bicyclic heterocycle;
wherein $R_3$ is hydrogen or halogen; and
wherein $R_4$ is hydrogen or aryl, the aryl being optionally substituted with one or more substituent selected from the group consisting of halogen, $C_1$-$C_4$ alkyl, $C_1$-$C_4$ alkoxy, phenyl, nitro, cyano, and —COCF$_3$.

In another aspect, the present disclosure provides a compound having Formula 3:

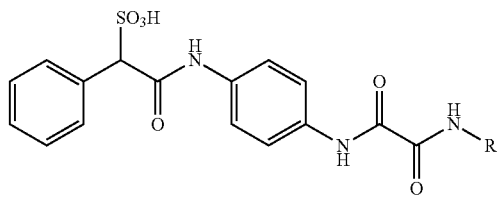

Formula 3 or a therapeutically suitable prodrug thereof or a therapeutically suitable salt thereof, wherein R is aryl or heteroaryl, optionally substituted with one or more substituent selected from the group consisting of $C_1$-$C_4$ alkyl, halogen, 1-imidazolyl, benzyl, and 2-thiophenyl.

In another aspect, the present disclosure provides a method of inhibiting a Src homogloy 2 typrosine phosophatase (SHP2) in a subject in need thereof. The method comprises administering to the subject a therapeutically effective amount of the compound of Formula 1b or of Formula 3, or a therapeutically suitable prodrug thereof or a therapeutically suitable salt thereof.

In another aspect, the present disclosure provides a method of treating a cancer in a subject in need thereof. The method comprises administering to the subject a therapeutically effective amount of the compound of Formula 1b or of Formula 3, or a therapeutically suitable prodrug thereof or a therapeutically suitable salt thereof.

In yet another aspect, the present disclosure provides a pharmaceutical composition comprising a compound of Formula 1b or of Formula 3, and a pharmaceutically acceptable carrier.

BRIEF DESCRIPTION OF THE DRAWINGS

FIG. 3A depicts a library in which SPAA was attached to diamine linkers and then coupled with 192 carboxylic acids to give a library of 960 compounds. FIG. 3B depicts a library in which SPAA with various substituents were coupled with 192 amines to give a library of 3264 compounds. FIG. 3C depicts a library in which SPAA was attached to oxalyl linkers and then coupled with 192 amines to give a library of 960 compounds.

FIG. 16A: Under inhibition assay conditions (pH 7 and 25° C., 20 nM SHP2, 3 mM pNPP, 100 μM cefsulodin, 50 mM 3,3-dimethylglutarate and 1 mM EDTA with an ionic strength of 0.15 M adjusted by addition of NaCl, total volume 100 μL), the reaction mixture was monitored at UV absorbance at 254 nm and analyzed by LC-MS at time points of 0 h, 3 h, 24 h and 48 h. LC-MS spectra at various time points showed no change in cefsulodin (retention time 6.1 min) and isonicotinamide (retention time 1.0 min, a marker of cefsulodin degradation) concentrations, while the level of pNPP (retention time 2.0 and 3.5 min) decreased progressively with concurrent increase of its hydrolyzed protein p-nitrophenol (retention time 8.6 min), indicating SHP2 was active throughout the 48 hours. FIG. 16B: Incubation with cefsulodin at a higher concentration of SHP2 (10 μM) under the same conditions for 3 hours showed no cefsulodin degradation, indicating cefsulodin was not reacting with SHP2.

FIG. 17A: ESI-MS analysis of SHP2 indicated that it has a molecular weight of 32224.58. FIG. 17B: After incubation of cefsulodin (100 μM) and SHP2 (100 μM) in 50 mM 3,3-dimethylglutarate and 1 mM EDTA with an ionic strength of 0.15 M (pH=7) for 3 hours, ESI-MS analysis showed only one peak at 32225.39. FIG. 17C: After incubation of cefsulodin (100 μM) and SHP2 (10 μM) in 50 mM 3,3-dimethylglutarate and 1 mM EDTA with an ionic strength of 0.15 M (pH=7.0) for 3 hours, ESI-MS analysis again showed only one peak at 32224.43. FIG. 17D: After incubation of phenyl vinyl sulfone (PVS) (100 μM) and SHP2 (100 nM) in 50 mM 3,3-dimethylglutarate and 1 mM EDTA with an ionic strength of 0.15 M (pH 7) for 10 minutes, ESI-MS analysis showed the unmodified SHP2 peak at 32224.20 and SHP2.PVS covalent adduct at 32392.34. PVS has a molecular mass of 168.21.

FIG. 18A. Fo-Fc electron density map (contoured at 3.0σ) around the catalytic P-loop after the refinement of apo-form SHP2 structure. FIG. 18B. 2Fo-Fc electron density map (contoured at 1.0σ) around the bound molecule (shown in stick) after the refinement of the complex structure. FIG. 18C. Chemical structure of the altered form observed in co-crystal structure. The molecular weight of the unambiguously observed part is 430. FIG. 18D. The molecule (represent in stick) binds into the active site of SHP2 (represent in surface) with abundant interactions with catalytic P-loop, pY-loop, Q-loop and WPD-loop. FIG. 18E. The detailed interactions between the altered cefsulodin (stick, green carbon) and SHP2. Residues within 5 Å of the altered cefsulodin are shown in white-carbon stick, and four loops constituting the active site pocket are shown in ribbon diagram and labeled. FIG. 18F. Superimposing structures of PTP1B.phosphopeptide complex (PDBID: 1EEN) and SHP29. Cefsulodin reveals that SPAA overlaps very well with pTyr residue in the phosphopeptide (cyan), suggesting it is a pTyr mimic.

FIG. 19A: The QTOF ESI-MS data of re-dissolved SHP2 crystals shows single peak at 32224.57. FIG. 19B: The QTOF ESI-MS data of re-dissolved co-crystal of SHP2 with Cefsulodin shows the protein peak at 32224.56 and an additional peak at 32652.80, and the difference of 428.24 corresponds to molecular mass of compound 1 after covalent bond formation between cefsulodin and SHP2.

FIG. 20A: The 2Fo-Fc electron density map (contoured at 1.0σ) around the backbone atoms (C, Cα and N, shown in stick) of the loop (residues 314-324) after the structure refinement. FIG. 20B: The compound 1 is covalently bonded to C318 of symmetric SHP2 molecule. FIG. 20C: The 2Fo-Fc electron density map (contoured at 1.0σ or 0.7σ) around the compound 1 indicates the covalent bond formation.

FIG. 21A: LC-MS analysis of freshly prepared cefsulodin in pH 7.0 buffer containing 50 mM 3,3-dimethylglutarate and 1 mM EDTA with an ionic strength of 0.15 M adjusted by addition of NaCl shows cefsulodin (retention time 6.1 min) was very pure with tiny amount of nicotinamide (retention time 1.0 min). FIG. 21B: In MES buffer with pH=5.8, cefsulodin and isonicotinamide concentrations were almost unchanged at all time points of 12 h, 1 d, 2 d, indicating cefsulodin was stable for at least 2 days. FIG. 21C: In CBTP buffer with pH=7.4, cefsulodin concentrations decreased progressively with the increase of isonicotinamide concentration through time points of 12 h, 1 d, 2 d, the minor peak at retention time 7.9 min belongs to cefsulodin and CBTP conjugated product (see FIG. 21A). Minor peak (retention time 6.0 min) left to cefsulodin belongs to racemized cefsulodin. FIG. 21D: In CBTP buffer with pH=9.1, cefsulodin concentrations decreased rapidly with the increase of isonicotinamide concentration through time point of 3 h, 6 h, 12 h, and cefsulodin was gone after 12 h. FIG. 21E: In crystallization solution, cefsulodin concentrations decreased progressively with the increase of isonicotinamide concentration through time points of 3 h, 1 d, 2 d, and the majority of cefsulodin was gone after 2 d, the minor peak at retention time 8.8 min belongs to cefsulodin and DTI conjugated product (see FIG. 21B).

FIGS. 22A-22D depict ESI-MS data of cefsulodin with buffer components. FIG. 22A: ESI-MS data of the minor peak at retention time 7.0 min in FIG. 22C middle spectrum shows the positive ion at 693.0 and the negative ion at 691.0, indicating the existence of a molecule with mass around 692.0. FIG. 22B: ESI-MS data of the minor peak at retention time 8.8 min in FIG. 21E middle spectrum shows the positive ion at 565.0 and the negative ion at 563.0, indicating the existence of a molecule with mass around 564.0. FIG. 22C: The chemical structure, exact mass, and molecule weight of a conjugate adduct of cefsulodin and CBTP, corresponding to the molecule with a retention time of 7.9 min in FIG. 22C middle spectrum. FIG. 22D: The chemical structure, exact mass, and molecule weight of a conjugate adduct of cefsulodin and DTI, corresponding to the molecule with a retention time of 8.8 min in FIG. 22E middle spectrum.

FIG. 23A: Two probable binding modes with similar calculated binding free energy. Cefsulodin is represented in stick, and SHP2 is represented in surface. FIG. 23B: Detailed interactions between cefsulodin and SHP2 in mode II. Residues within 5 Å distance of the cefsulodin are shown in white carbon stick, and four loops constituting the active site pocket are shown in ribbon diagram and highlighted.

FIG. 24A: The design of novel and stable SHP2 inhibitors that resemble cefsulodin structures. FIG. 24B: 4 sub-libraries were designed, in which carboxylic acid will couple with a set of 192 amines to afford a total of 768 compounds. FIG. 24C: The chemical structures of hits that inhibit SHP2 with good activity and specificity.

FIG. 26A: MTT assay for compounds 2 to 7 in H1975 non-small cell lung cancer (NSCLC) cell line. Compounds 2, 5, 6 significantly ($p<0.01$) reduced cell proliferation at 20 μM and 40 μM in a dose dependent manner. FIG. 26B: MTT assay of compounds 2 to 7 in MDA-MB-231 breast cancer cell line. Compounds 2, 5, 6 also significantly ($p<0.01$) reduced cell survival at 20 μM and 40 μM in dose dependent manner. FIG. 26C: In H1975 lung cancer cells, compound 2 was able to decrease the EGF-mediated ERK1/2 phosphorylation in a dose dependent manner. FIG. 26D: The structurally related negative control compound 7 failed to block EGF-mediated ERK1/2 phosphorylation at 40 μM. FIG. 26E: compound 2 had no effect on PMA-stimulated ERK1/2 phosphorylation.

FIG. 27A. SKBR3 cell growth in Matrigel over 5 days in the presence of vehicle or the indicated concentrations of compound 2. FIG. 27B. The levels of total and phospho ERK1/2 were detected by immunoblot from lysates prepared from cells recovered from Matrigel shown in FIG. 27A.

DEFINITIONS

Figure 1:
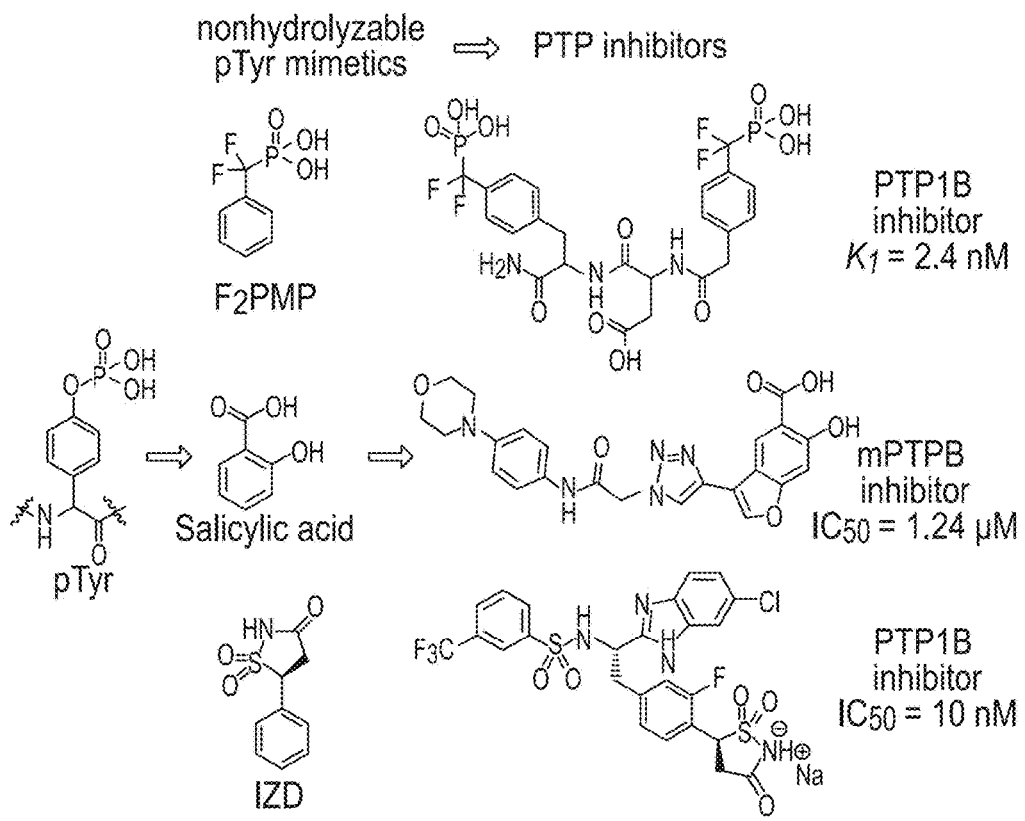
FIG. 1 depicts the development of FTP inhibitors that rely on the design of pTyr mimetics.

As intended herein, the terms "a" and "an" include singular as well as plural references unless the context clearly dictates otherwise. For example, the term "a PTP inhibitor" can include one or more such inhibitors.

As used herein, "inhibition" or "inhibitory activity" each encompass whole or partial reduction of activity or effect of an enzyme.

As used herein, "susceptible" and "at risk" refer to having little resistance to a certain disease, disorder or condition, including being genetically predisposed, having a family history of, and/or having symptoms of the disease, disorder or condition.

"Treatment" as used herein includes the alleviation, prevention, reversal, amelioration or control of a pathology, disease, disorder, process, condition or event, such as diabetes, or the symptoms of such pathology, disease, disorder, process, condition or event. In this context, the term "treatment" is further to be understood as embracing the use of a compound to inhibit, block, reverse, restrict or control progression of a disease, disorder, or condition associated with inappropriate activity of a protein phosphatase.

As used herein, the terms "pharmaceutical composition" and "pharmaceutical formulation" refer to compositions of matter comprising at least one pharmaceutical compound.

The term "therapeutically suitable salt," refers to salts or zwitterions of pharmaceutical compounds which are water or oil-soluble or dispersible, suitable for treatment of disorders and effective for their intended use. The salts may be prepared, for instance, during the final isolation and purification of the compounds or separately by reacting an amino group of the compounds with a suitable acid. For example, a compound may be dissolved in a suitable solvent, such as, but not limited to methanol and water, and treated with at least one equivalent of an acid, for instance hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of a compound may also be quaternized with alkyl chlorides, bromides, and iodides such as methyl, ethyl, propyl, isopropyl, butyl, lauryl, myristyl, stearyl, and the like.

Basic addition salts may be prepared, for instance, during the final isolation and purification of pharmaceutical compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts may be derived, for example, from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like.

The term "therapeutically suitable prodrug," refers to those prodrugs or zwitterions which are suitable for use in contact with the tissues of subjects and are effective for their intended use. The term "prodrug" refers to compounds that are transformed in vivo to a pharmaceutical compound, for example, by hydrolysis in blood. The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art.

The terms "specificity" or "selectivity" or "preference" of a certain PTP inhibitor for one PTP over another PTP, as described herein, is expressed as fold of increase in inhibition activity, which is calculated as the inverted ratio of $IC_{50}$ of the same inhibitor against different FTPs. For example, specificity for mPTPB over mPTPA equals $[IC_{50}$ (mPTPA)]/$[IC_{50}$ (mFTPB)].

The term "associated with abnormal activity of a protein tyrosine phosphatase" encompasses all diseases, disorders, or conditions in which symptoms are, in part, related to excessive or deficient activity of a protein tyrosine phosphatase, as compared to the activity of the protein tyrosine phosphatase of a subject without such diseases, disorders, or conditions.

DETAILED DESCRIPTION OF THE DISCLOSURE

The present disclosure is generally directed to small molecule inhibitors of PTPs and their uses as effective therapeutics, and more particularly, to inhibitors of mPTPA, mFPTPB, LMWPTP, Laforin, SHP2, LYP, and HePTP. These inhibitors can be administered to treat/control/mitigate diseases and conditions including cancer, diabetes, infectious and neurological diseases.

Generally, the present disclosure provides a library of compounds derived from α-sulfophenylacetic amide (SPAA) as novel sulfonic acid based pTyr mimetics. These compounds have a structure of Formula 1:

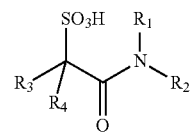

Formula 1 or a therapeutically suitable prodrug thereof or a therapeutically suitable salt thereof, wherein $R_1$ is hydrogen and $R_2$ is selected from $C_1$-$C_{10}$ alkyl, aryl, heteroaryl, —NH—$R_{2a}$, —(CH$_2$)$_m$NH—CO—$R_x$, and —(CH$_2$)$_n$—$R_{2b}$—(CH$_2$)$_q$—NH—CO—CO—NH—$R_y$;

wherein, when $R_2$ is aryl or heteroaryl, $R_2$ is optionally substituted with one or more substituent selected from the group consisting of $C_1$-$C_4$ alkyl, $C_1$-$C_4$ alkoxy, $C_1$-$C_4$ alkoxy carbonyl, amino, aryl, benzyloxy (—OBn), —CF$_3$, carboxy, halogen, 1-imidazolyl, 4-morpholinyl, nitro, and —(CH$_2$)$_s$—NH—CO—$R_1$;

wherein m, n, q, and s independently are 0-4;

wherein $R_2$, and $R_{2b}$ independently are aryl;

wherein $R_x$, $R_y$, and $R_z$ independently are aryl or heteroaryl, and the aryl or heteroaryl are independently optionally substituted with one or more substituent selected from the group consisting of $C_1$-$C_4$ alkyl, benzoyl, benzyl, benzyloxy (—OBn), phenyl, halogen, 1H-benzimidazole-2-yl, and 2-thiophenyl;

or wherein $R_1$, $R_2$, and the N atom to which they are attached are joined together to form a monocyclic or bicyclic heterocycle;

wherein $R_3$ is hydrogen or halogen; and wherein $R_4$ is hydrogen or aryl, the aryl being optionally substituted with one or more substituent selected from the group consisting of halogen, $C_1$-$C_4$ alkyl, $C_1$-$C_4$ alkoxy, phenyl, nitro, cyano, and —COCF$_3$.

Figure 3A:
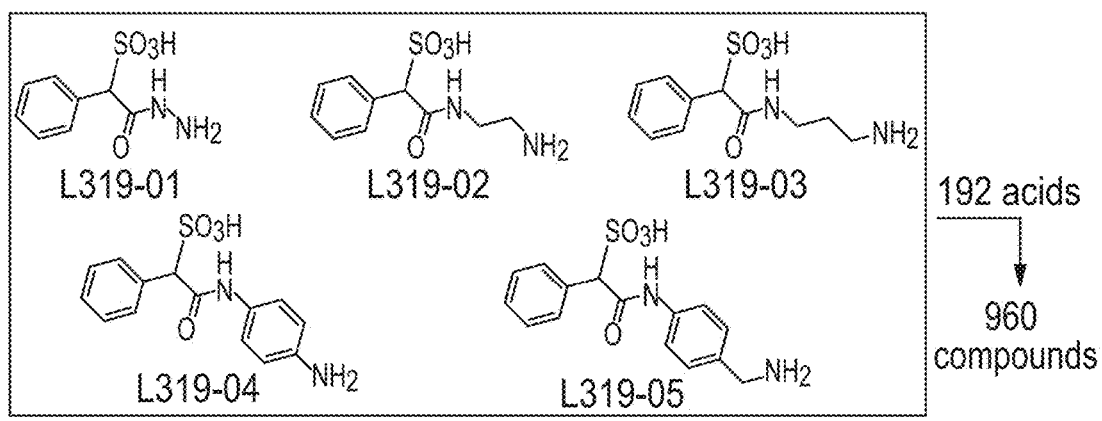
FIGS. 3A-3C depict three libraries between α-sulfophenyl acetic acid and amines under peptide coupling conditions.
Figure 3B:
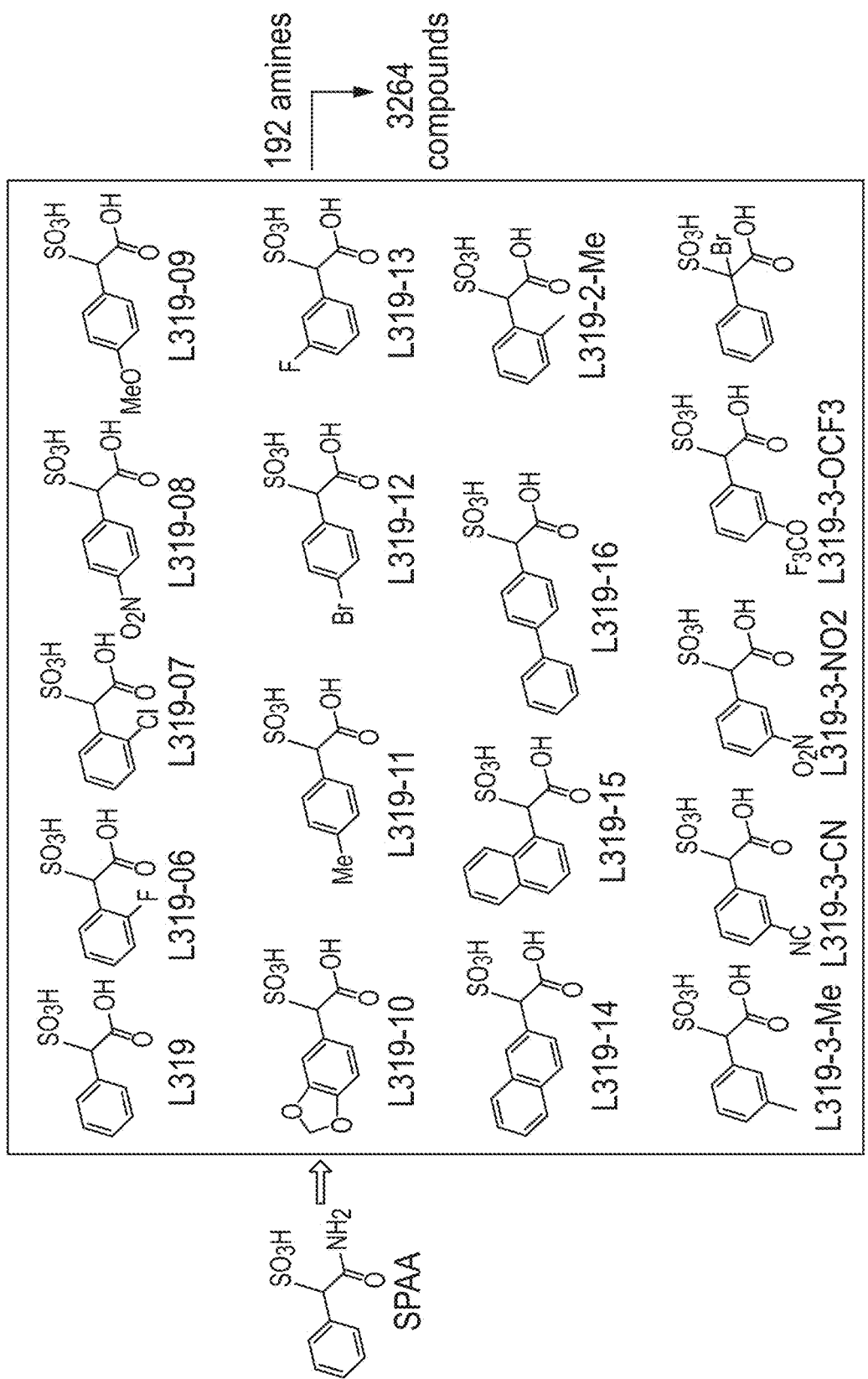
Figure 3C:
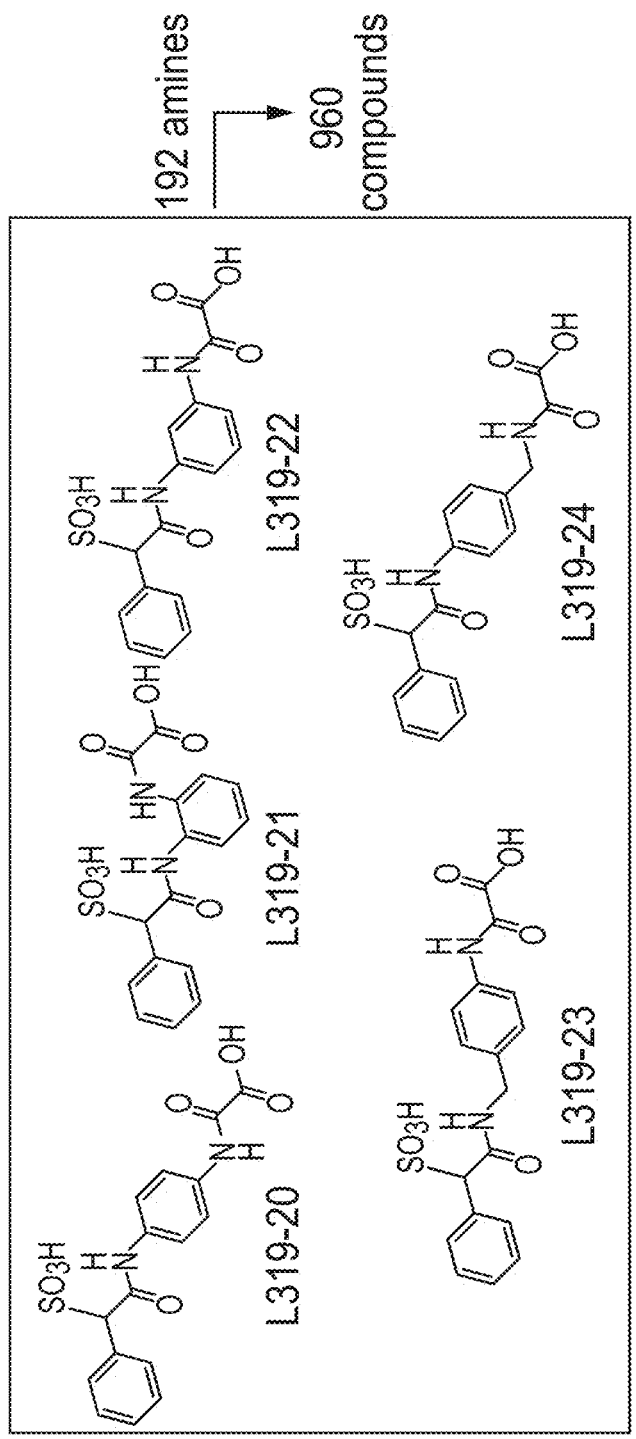

Based on the structure of α-sulfophenylacetic amide (SPAA), three libraries of compounds are provided herein. A total of more than 5000 compounds have been synthesized through peptide coupling reaction using 192 carboxylic acids (for free amines intermediates) and 192 amines (for free carboxylic acid intermediates). As shown in FIGS. 3A-3C, the three libraries of compounds are derived from 3 groups of SPAA analogs: Group A with diamine linker, Group B with substitution on the phenyl residue or on the α-carbon, and Group C with oxalyl linkers. Coupling of the library of carboxylic acids or amines with the corresponding amino or carboxy SPAA analogs in Groups A-C through peptide bond formation provides exemplary compounds of Formula 1 (typically with a molecular weight (MW) of 200 to 700).

Accordingly, in Formula 1, $R_1$ and $R_2$ can be separate moieties and $R_1$ is hydrogen. In some embodiments, $R_1$ is hydrogen, and $R_2$ is aryl or heteroaryl. Suitably, in some embodiments, $R_2$ is phenyl or benzo[d]thiazol-2-yl, optionally substituted with one or more substituent selected from the group consisting of $C_1$-$C_4$ alkyl, $C_1$-$C_4$ alkoxy, $C_1$-$C_4$ alkoxy carbonyl, amino, aryl, benzyloxy (—OBn), —CF$_3$, carboxy, halogen, 1-imidazolyl, 4-morpholinyl, and nitro.

More particularly, in one aspect for example, the present disclosure provides compounds of Formula 1a:

Formula 1a

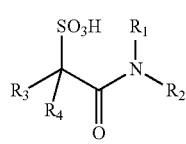

or a therapeutically suitable prodrug thereof or a therapeutically suitable salt thereof, wherein $R_1$ is hydrogen and $R_2$ is selected from $C_1$-$C_{10}$ alkyl, aryl, heteroaryl, —NH—$R_{2a}$, —(CH$_2$)$_m$NH—CO—$R_x$, and —(CH$_2$)$_n$—$R_{2b}$—(CH$_2$)$_q$—NH—CO—CO—NH—$R_y$;
  wherein, when $R_2$ is aryl or heteroaryl, $R_2$ is optionally substituted with one or more substituent selected from the group consisting of $C_1$-$C_4$ alkyl, $C_1$-$C_4$ alkoxy, $C_1$-$C_4$ alkoxy carbonyl, amino, aryl, benzyloxy (—OBn), —CF$_3$, carboxy, halogen, 1-imidazolyl, 4-morpholinyl, and nitro;
  wherein m, n, and q independently are 0-4;
  wherein $R_{2a}$ and $R_{2b}$ independently are aryl;
  wherein $R_x$ and $R_y$ independently are aryl or heteroaryl, and the aryl or heteroaryl are independently optionally substituted with one or more substituent selected from the group consisting of $C_1$-$C_4$ alkyl, benzoyl, benzyl, benzyloxy (—OBn), phenyl, halogen, 1H-benzimidazole-2-yl, and 2-thiophenyl;
or wherein $R_1$, $R_2$, and the N atom to which they are attached are joined together to form a monocyclic or bicyclic heterocycle;
wherein $R_3$ is hydrogen or halogen; and
wherein $R_4$ is hydrogen or aryl, the aryl being optionally substituted with one or more substituent selected from the group consisting of halogen, $C_1$-$C_4$ alkyl, $C_1$-$C_4$ alkoxy, phenyl, nitro, cyano, and —COCF$_3$.

In another aspect for example, the present disclosure provides compounds of Formula 1b:

Formula 1b

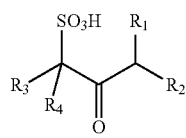

or a therapeutically suitable prodrug thereof or a therapeutically suitable salt thereof, wherein R1 is hydrogen and R2 is aryl or heteroaryl and is substituted with —(CH$_2$)$_s$—NH—CO—$R_z$;
  wherein s is 0-4;
  wherein $R_z$ is aryl or heteroaryl, and the aryl or heteroaryl are independently optionally substituted with one or more substituent selected from the group consisting of $C_1$-$C_4$ alkyl, benzoyl, benzyl, benzyloxy (—OBn), phenyl, halogen, 1H-benzimidazole-2-yl, and 2-thiophenyl;
or wherein $R_1$, $R_2$, and the N atom to which they are attached are joined together to form a monocyclic or bicyclic heterocycle;
wherein $R_3$ is hydrogen or halogen; and
wherein $R_4$ is hydrogen or aryl, the aryl being optionally substituted with one or more substituent selected from the group consisting of halogen, $C_1$-$C_4$ alkyl, $C_1$-$C_4$ alkoxy, phenyl, nitro, cyano, and —COCF$_3$.

By way of further examples, as shown in Table 1, $R_2$ can be a phenyl substituted with bromo and methyl groups (L319M34), or $R_2$ can be a benzo[d]thiazol-2-yl moiety (L319-15). In other embodiments, the —NH—$R_2$ structure is derived from a diamine linker (i.e. library of Group A compounds), such as the ones shown in L319-02-A60 and L319-05-A64 (Table 2). In other embodiments, the —NH—$R_2$ structure is derived from an oxalyl linker, which is coupled to the α-sulfophenylacetyl moiety through a diamine linker, such as the ones shown in L319-21-M52 (Table 2), L319-20-M24 (Table 3), and L319-24-M77 (Table 3).

TABLE 1

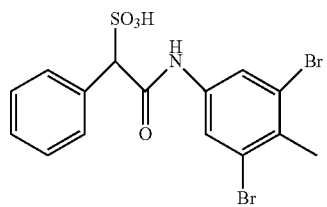 [SMILES: Cc1c(Br)cc(NC(=O)C(c2ccccc2)S(=O)(=O)O)cc1Br]
L319M34

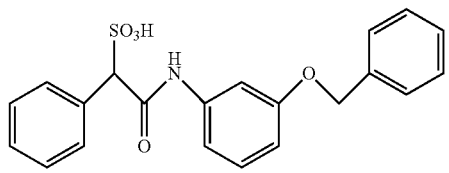 [SMILES: O=C(Nc1cccc(OCc2ccccc2)c1)C(c1ccccc1)S(=O)(=O)O]
L319M52

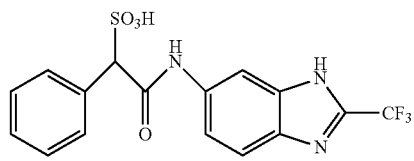 [SMILES: O=C(Nc1ccc2nc(C(F)(F)F)[nH]c2c1)C(c1ccccc1)S(=O)(=O)O]
L319M54

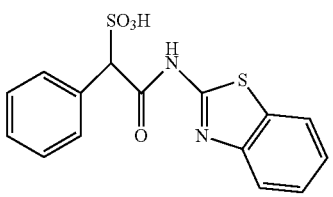 [SMILES: O=C(Nc1nc2ccccc2s1)C(c1ccccc1)S(=O)(=O)O]
L319N15

TABLE 1-continued
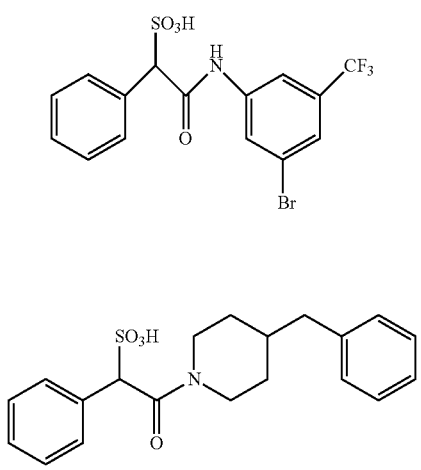
L319N22
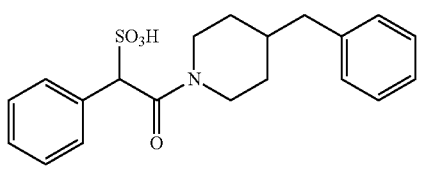 [SMILES: O=C(C(c1ccccc1)S(=O)(=O)O)N1CCC(Cc2ccccc2)CC1]
L319N46
TABLE 1-continued
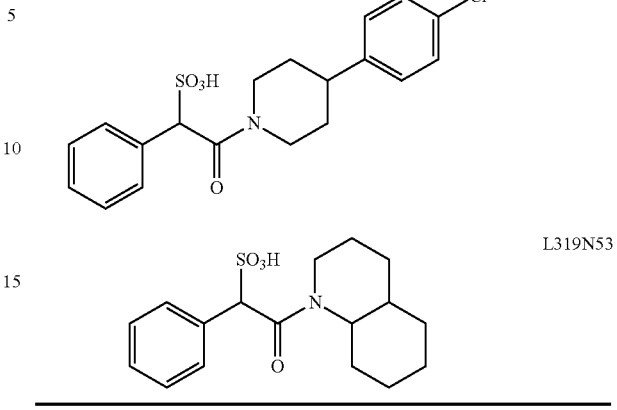
L319N47
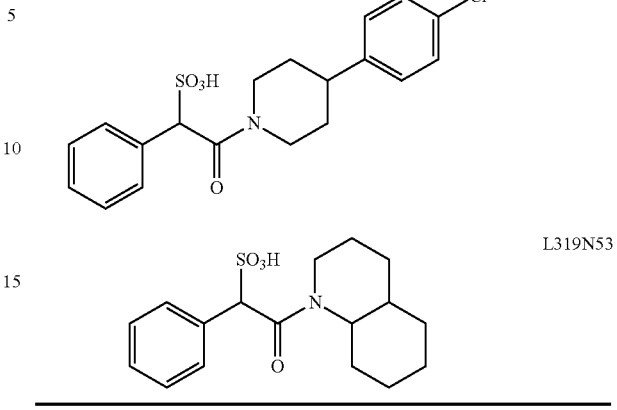
L319N53
TABLE 2
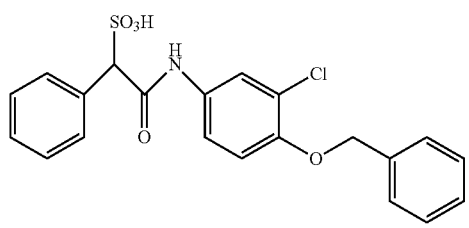 [SMILES: O=C(Nc1ccc(OCc2ccccc2)c(Cl)c1)C(c1ccccc1)S(=O)(=O)O]
L319M50
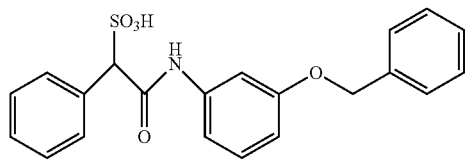 [SMILES: O=C(Nc1cccc(OCc2ccccc2)c1)C(c1ccccc1)S(=O)(=O)O]
L319M52
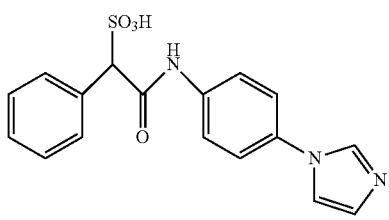 [SMILES: O=C(Nc1ccc(-n2ccnc2)cc1)C(c1ccccc1)S(=O)(=O)O]
L319M63
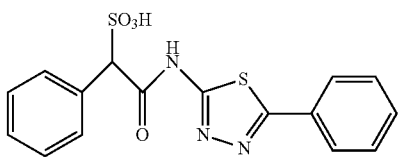 [SMILES: O=C(Nc1nnc(-c2ccccc2)s1)C(c1ccccc1)S(=O)(=O)O]
L319M73-2
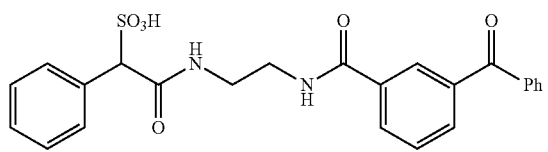 [SMILES: O=C(NCCNC(=O)C(c1ccccc1)S(=O)(=O)O)c1cccc(C(=O)c2ccccc2)c1]
L319-02-A60

TABLE 2-continued
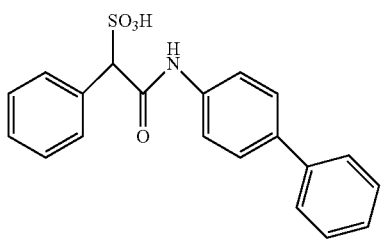 [SMILES: O=C(Nc1ccc(-c2ccccc2)cc1)C(c1ccccc1)S(=O)(=O)O]
L319N08
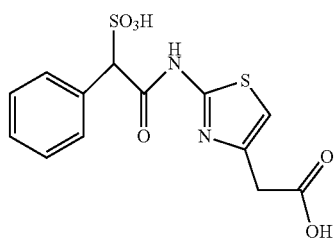 [SMILES: O=C(O)Cc1csc(NC(=O)C(c2ccccc2)S(=O)(=O)O)n1]
L319N72
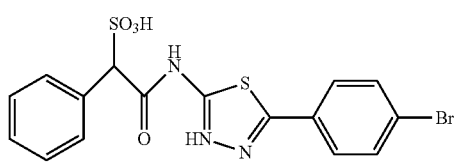 [SMILES: O=C(Nc1nnc(-c2ccc(Br)cc2)s1)C(c1ccccc1)S(=O)(=O)O]
L319M78
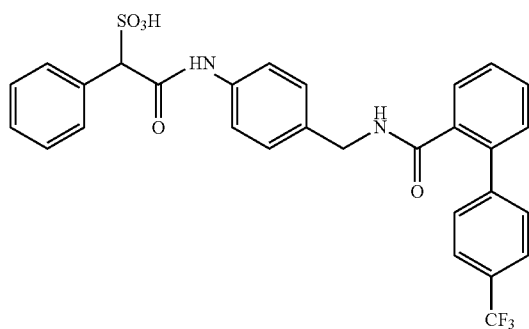 [SMILES: O=C(NCc1ccc(NC(=O)C(c2ccccc2)S(=O)(=O)O)cc1)c1ccccc1-c1ccc(C(F)(F)F)cc1]
L319-05-A64
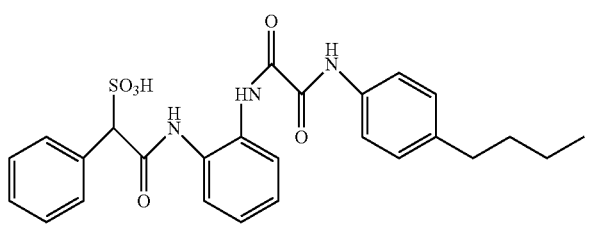 [SMILES: CCCCc1ccc(NC(=O)C(=O)Nc2ccccc2NC(=O)C(c2ccccc2)S(=O)(=O)O)cc1]
L319-21-M06
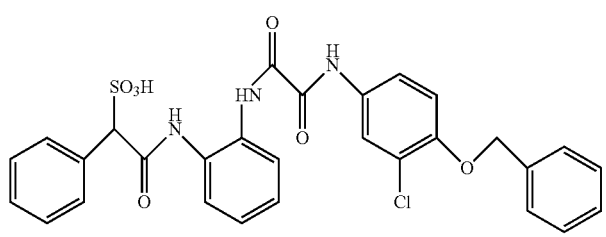 [SMILES: O=C(Nc1ccc(OCc2ccccc2)c(Cl)c1)C(=O)Nc1ccccc1NC(=O)C(c1ccccc1)S(=O)(=O)O]
L319-21-M50

TABLE 2-continued
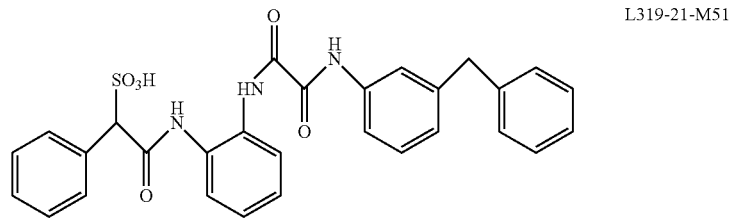
L319-21-M51
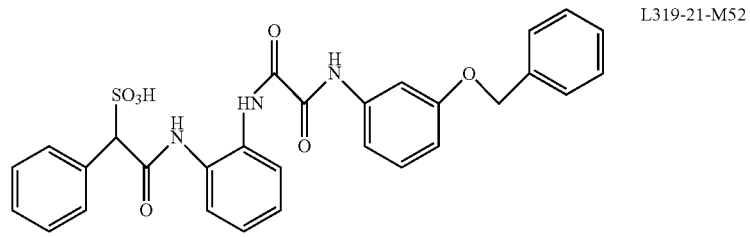
L319-21-M52
TABLE 3
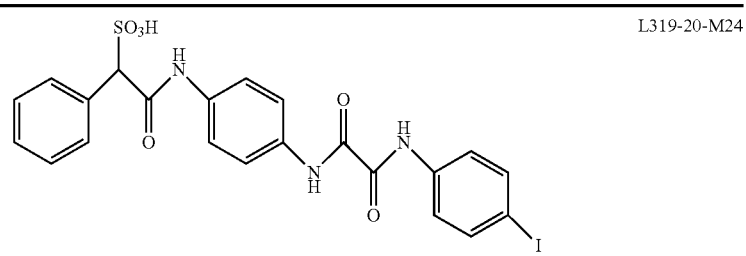
L319-20-M24
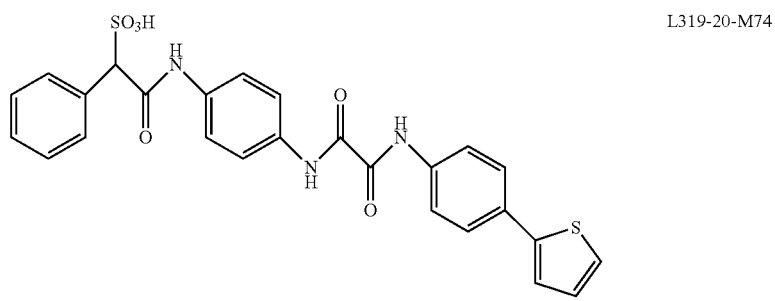
L319-20-M74
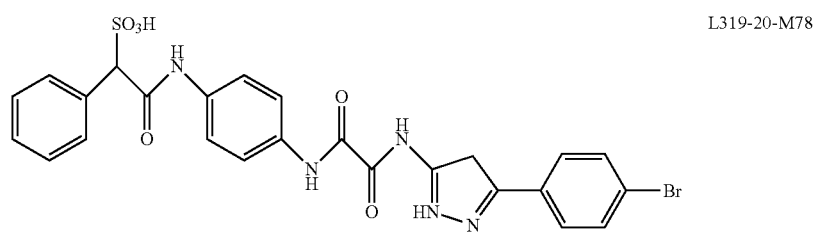
L319-20-M78
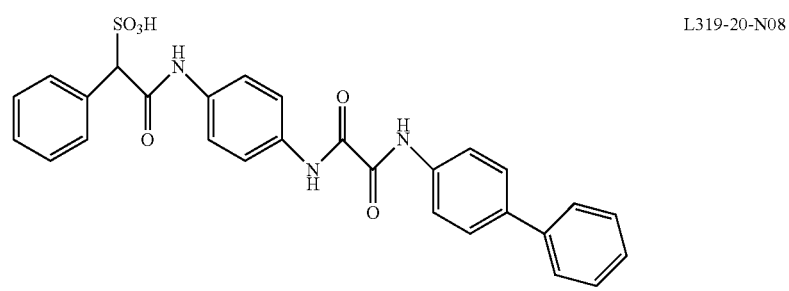
L319-20-N08

TABLE 3-continued
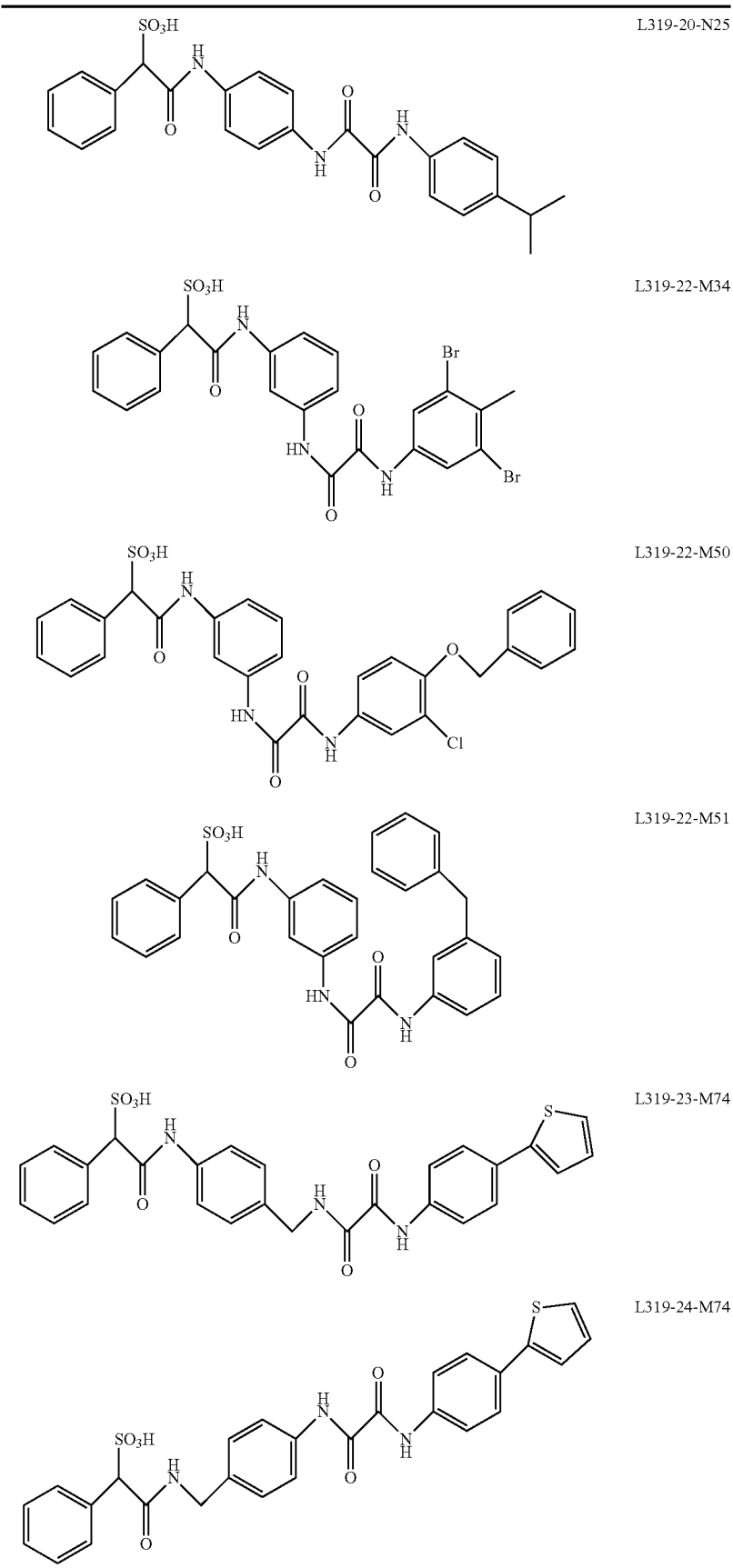
L319-20-N25
L319-22-M34
L319-22-M50
L319-22-M51
L319-23-M74
L319-24-M74

TABLE 3-continued

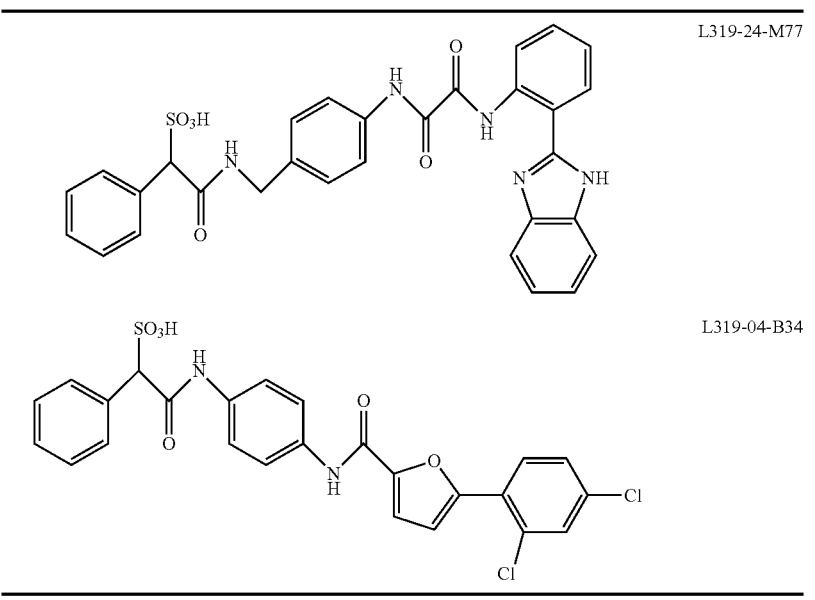

In other embodiments, compounds in which the α-phenyl is replaced by a hydrogen atom are also provided, such as L335N5-07 and L335M34 shown in Table 4. With respect to $R_3$ and $R_4$ of Formula, as shown in FIG. 3B, the hydrogen on the α-carbon of the α-sulfophenylacetyl moiety can be replaced by halogen (such as bromo), and the phenyl group can be replaced by other aromatic groups (such as naphthalenyl). In addition, the aromatic group on the α-carbon of the α-sulfophenylacetyl moiety can have substituents such as halogen, $C_1$-$C_4$ alkyl, phenyl, nitro, and $COCF_3$.

TABLE 4

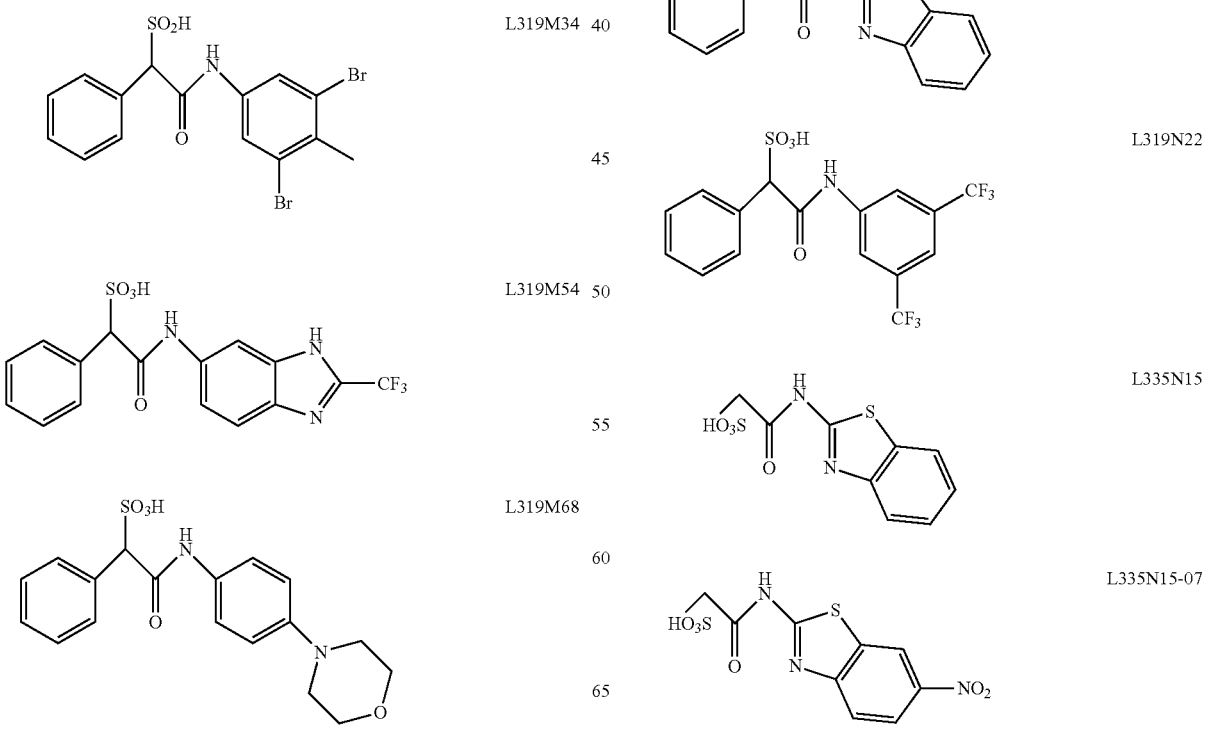

TABLE 4-continued

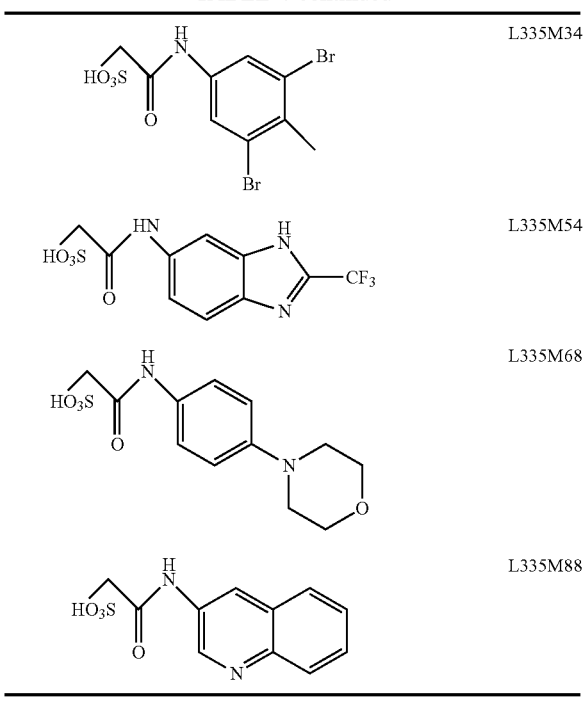

In yet another embodiment, R$_1$, R$_2$, and the N atom to which they are attached are joined together to form a monocyclic or bicyclic heterocycle, such as those shown in L319N46, L319N47, and L319N53 (Table 1). Preferably, R$_1$, R$_2$, and the N atom form a heterocycle selected from the group consisting of:

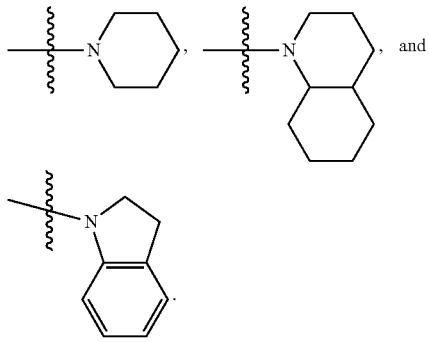

The present disclosure further provides a compound of Formula 2:

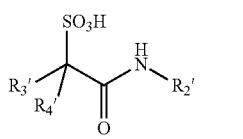

Formula 2 wherein R$_2$' is heterocycle, optionally substituted with one or more substituent selected from the group consisting of C$_1$-C$_4$ alkyl, C$_1$-C$_4$ alkoxy, C$_1$-C$_4$ alkoxy carbonyl, amino, aryl, benzyloxy (—OBn), —CF$_3$, carboxy, halogen, 1-imidazolyl, 4-morpholinyl, and nitro;

wherein R$_3$' is hydrogen or halogen; and
wherein R$_4$' is hydrogen or aryl, the aryl being optionally substituted with one or more substituent selected from the group consisting of halogen, C$_1$-C$_4$ alkyl, C$_1$-C$_4$ alkoxy, phenyl, nitro, cyano, and —COCF$_3$.

Other non-limiting examples of the novel α-sulfophenylacetic amide compounds are included in the present disclosure, as shown in the Examples and Tables 1-7.

TABLE 5

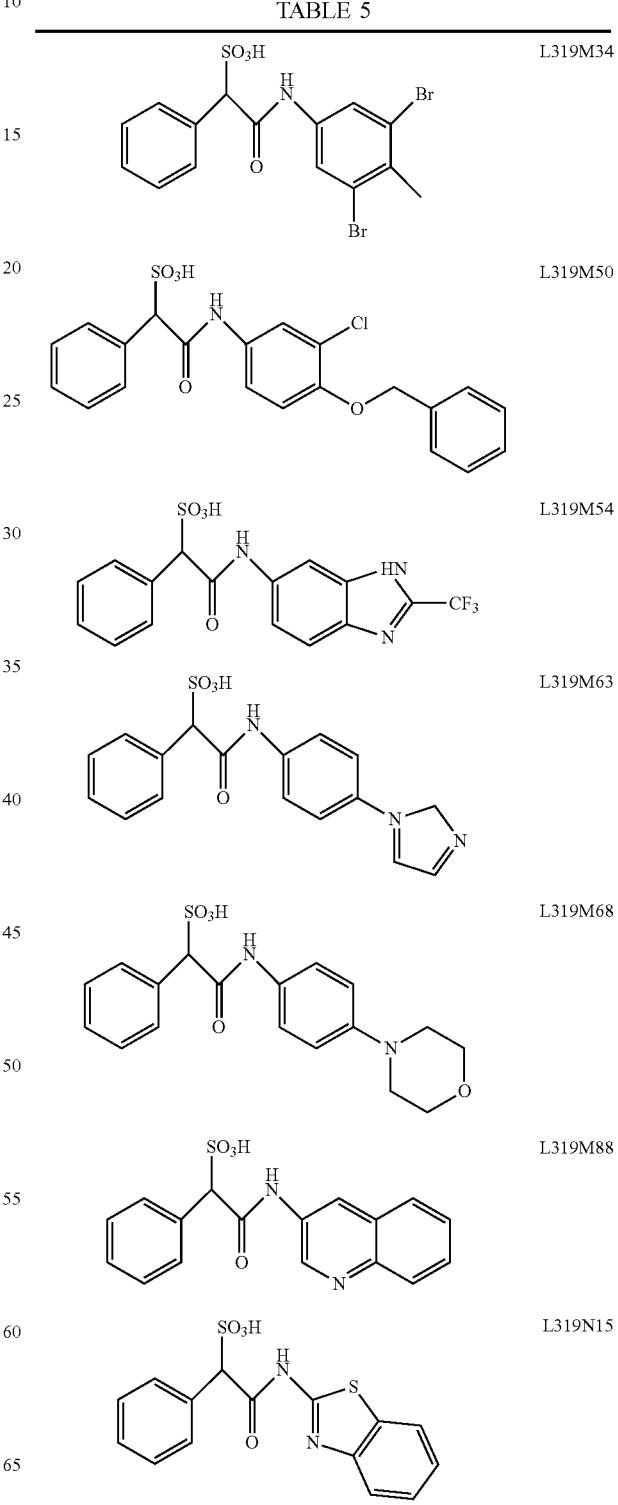

TABLE 5-continued
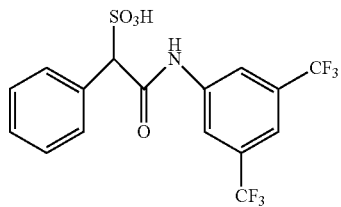 [SMILES: O=C(Nc1cc(C(F)(F)F)cc(C(F)(F)F)c1)C(c1ccccc1)S(=O)(=O)O] L319N22
TABLE 6
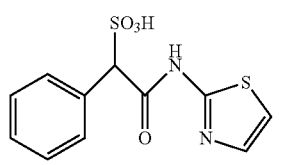 [SMILES: O=C(Nc1nccs1)C(c1ccccc1)S(=O)(=O)O] L319N13
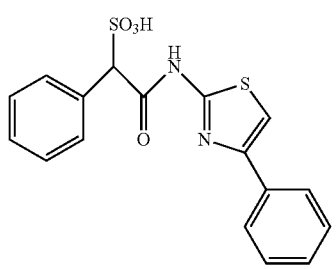 [SMILES: O=C(Nc1nc(-c2ccccc2)cs1)C(c1ccccc1)S(=O)(=O)O] L319N54
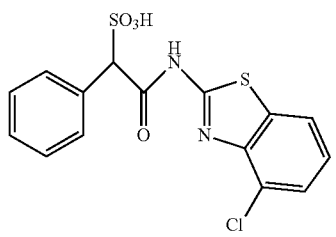 [SMILES: O=C(Nc1nc2c(Cl)cccc2s1)C(c1ccccc1)S(=O)(=O)O] L319N15-01
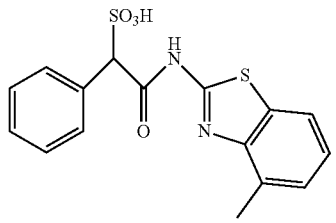 [SMILES: Cc1cccc2sc(NC(=O)C(c3ccccc3)S(=O)(=O)O)nc12] L319N15-02
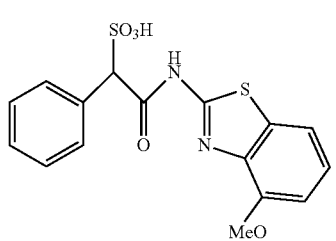 [SMILES: COc1cccc2sc(NC(=O)C(c3ccccc3)S(=O)(=O)O)nc12] L319N15-03
TABLE 6-continued
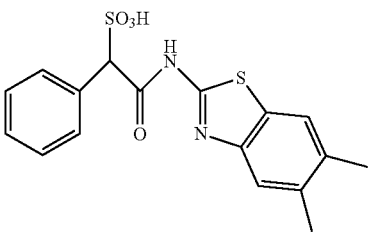 [SMILES: Cc1cc2nc(NC(=O)C(c3ccccc3)S(=O)(=O)O)sc2cc1C] L319N15-04
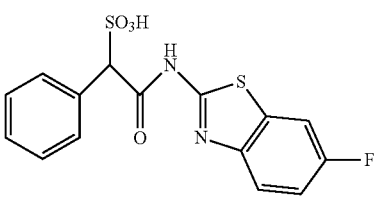 [SMILES: O=C(Nc1nc2ccc(F)cc2s1)C(c1ccccc1)S(=O)(=O)O] L319N15-05
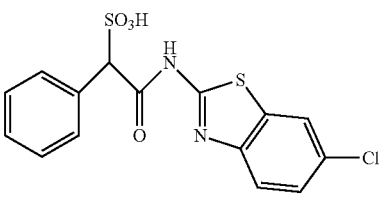 [SMILES: O=C(Nc1nc2ccc(Cl)cc2s1)C(c1ccccc1)S(=O)(=O)O] L319N15-06
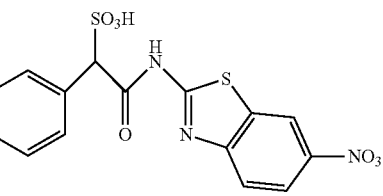 L319N15-07
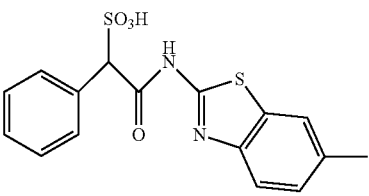 [SMILES: Cc1ccc2nc(NC(=O)C(c3ccccc3)S(=O)(=O)O)sc2c1] L319N15-08
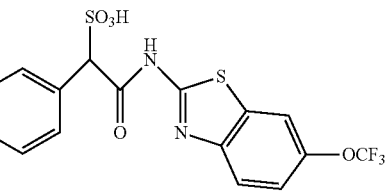 L319N15-09
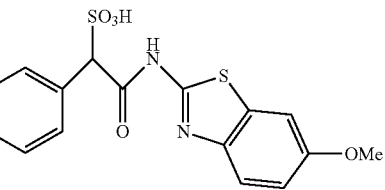 L3169N15-10
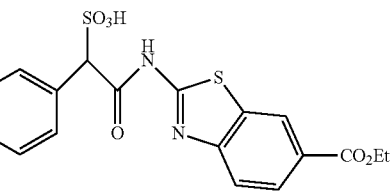 L319N15-11

TABLE 6-continued
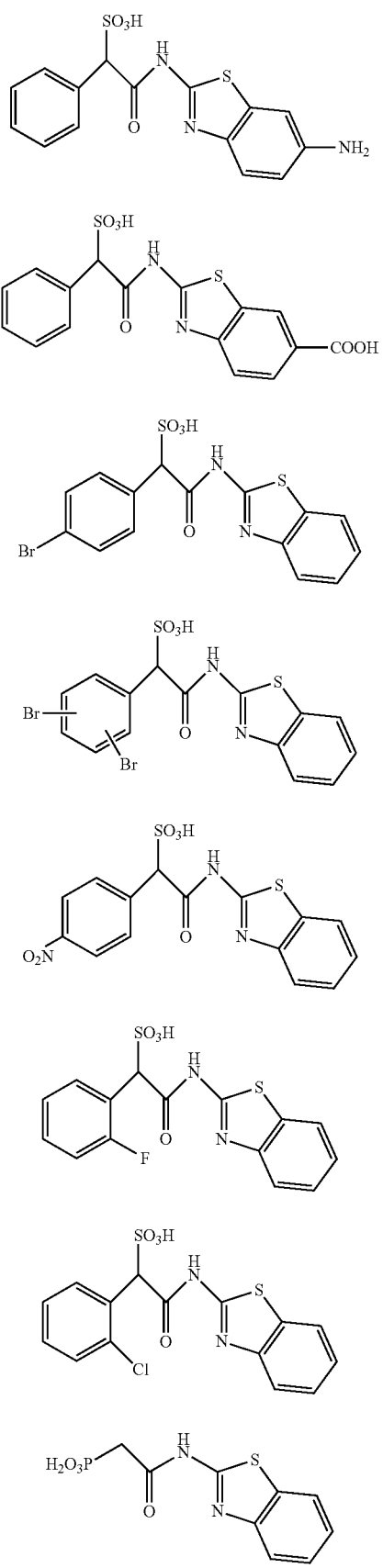
TABLE 6-continued
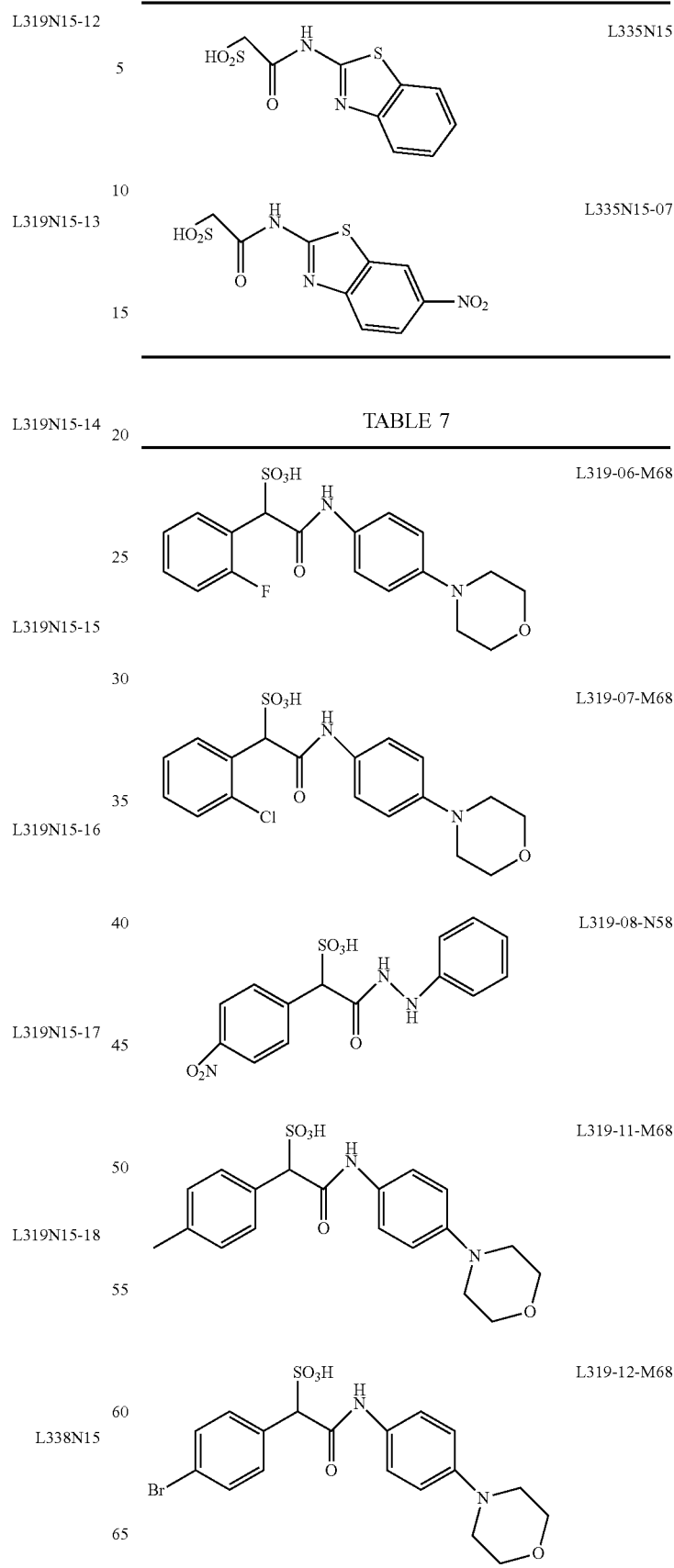
TABLE 7

TABLE 7-continued
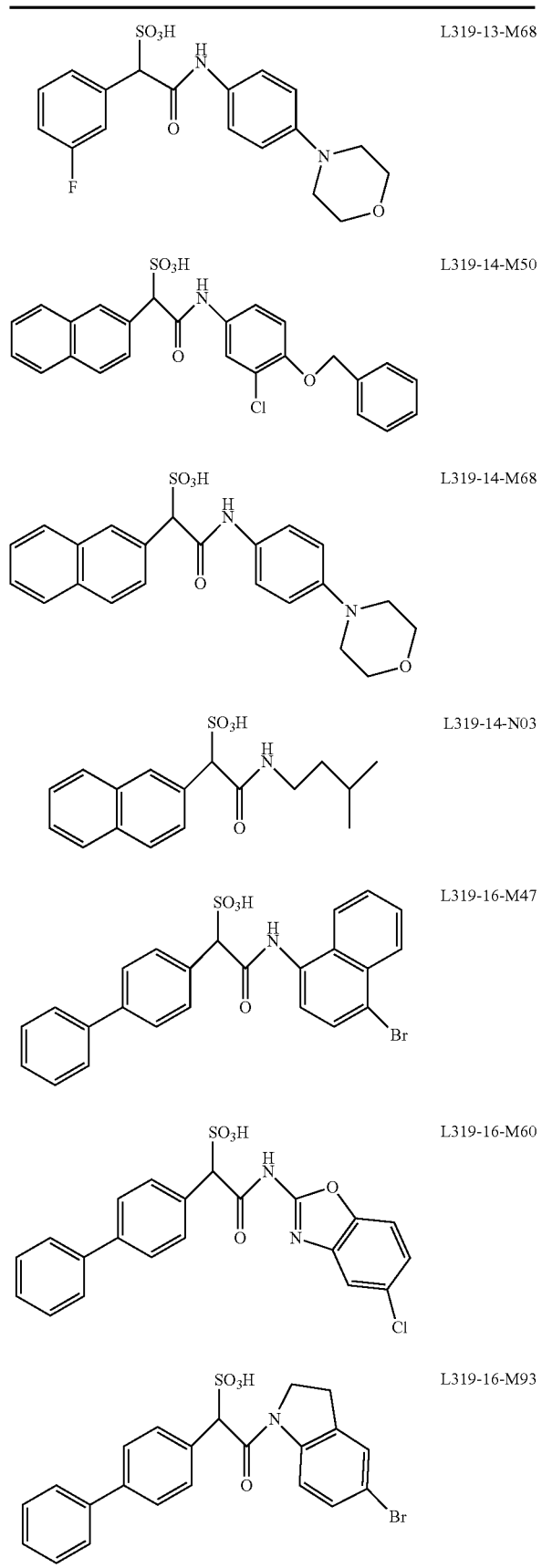
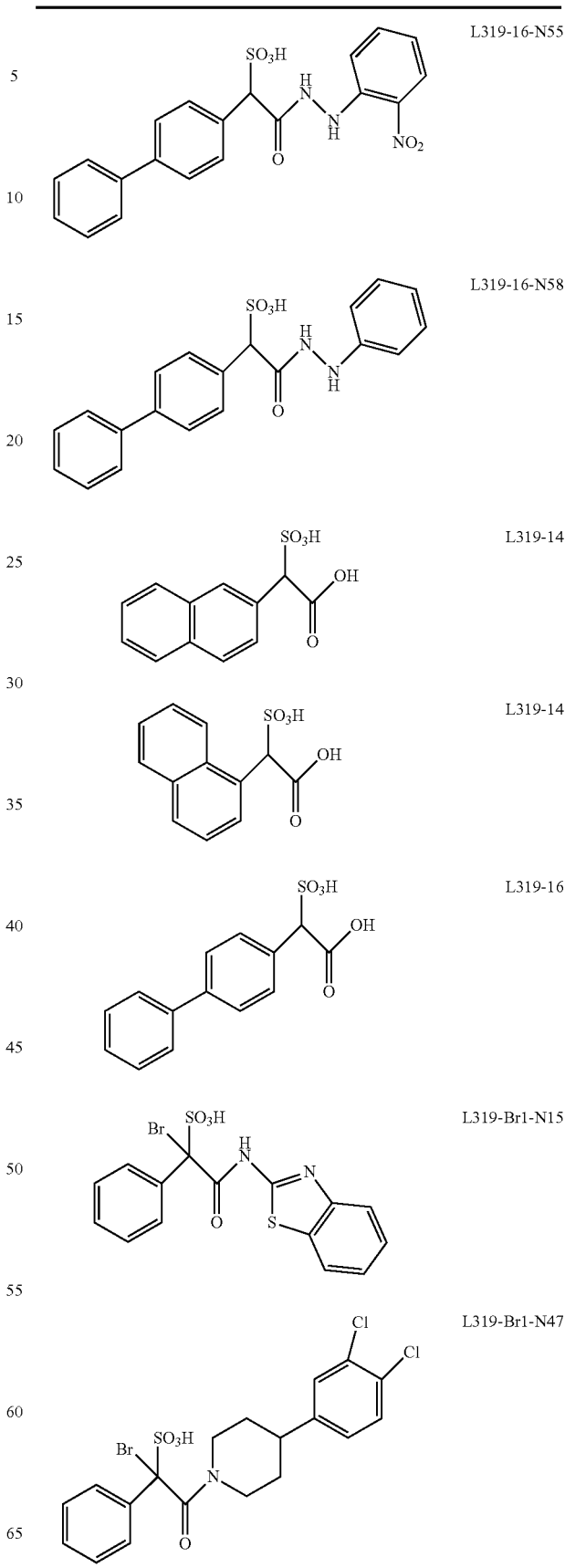

TABLE 7-continued

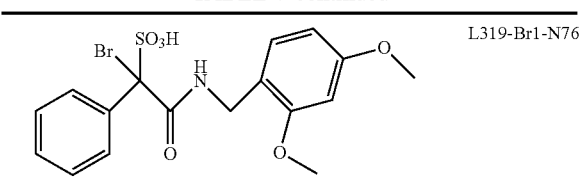

L319-Br1-N76

The present disclosure further provides a compound of Formula 3:

Formula 3

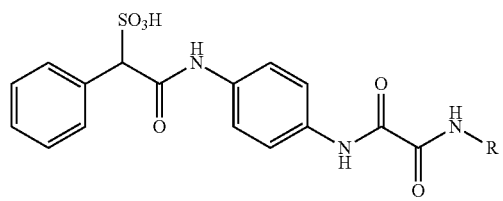

or a therapeutically suitable prodrug thereof or a therapeutically suitable salt thereof, wherein R is aryl or heteroaryl, optionally substituted with one or more substituent selected from the group consisting of $C_1$-$C_4$ alkyl, halogen, 1-imidazolyl, benzyl, and 2-thiophenyl. These compounds have been found to specifically inhibit SHP2 and can be administered to treat/control/mitigate diseases and conditions including cancer, diabetes, infectious and neurological diseases. Particularly, these inhibitors can be administered to treat/control/mitigate cancers such as breast cancer, lung cancer, colon cancer, prostate cancer, neuroblastoma, glioblastoma, melanoma, hepatocellular carcinoma, and leukemia.

Particularly suitable compounds of Formula 3 are shown in Table 8 below.

TABLE 8

| Compound | Structure |
|---|---|
| 2 | 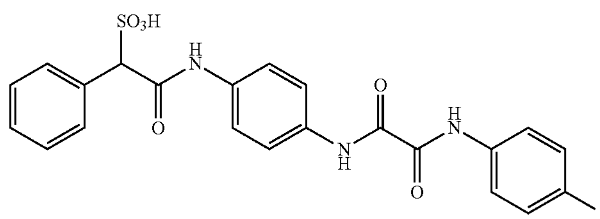 |
| 3 | 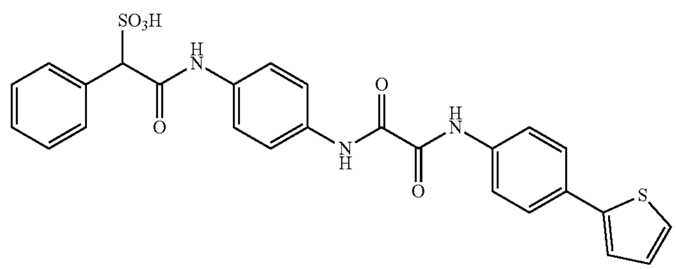 [SMILES: O=C(Nc1ccc(NC(=O)C(c2ccccc2)S(=O)(=O)O)cc1)C(=O)Nc1ccc(-c2cccs2)cc1] |
| 4 | 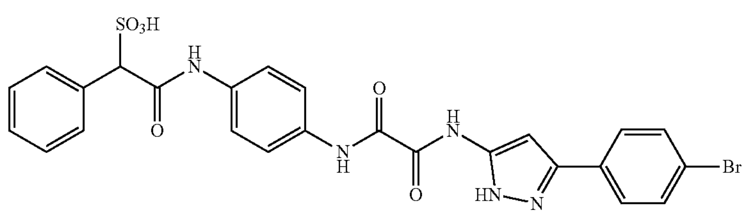 [SMILES: O=C(Nc1ccc(NC(=O)C(c2ccccc2)S(=O)(=O)O)cc1)C(=O)Nc1cc(-c2ccc(Br)cc2)n[nH]1] |
| 5 | 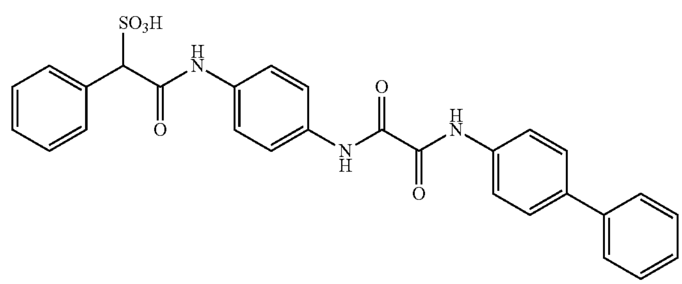 [SMILES: O=C(Nc1ccc(NC(=O)C(c2ccccc2)S(=O)(=O)O)cc1)C(=O)Nc1ccc(-c2ccccc2)cc1] |

TABLE 8-continued

| Compound | Structure |
|---|---|
| 6 | (structure: phenyl-CH(SO₃H)-C(=O)-NH-(p-phenylene)-NH-C(=O)-C(=O)-NH-(p-phenylene)-isopropyl) |
| 7 | (structure: phenyl-CH(SO₃H)-C(=O)-NH-(p-phenylene)-NH-C(=O)-C(=O)-NH-phenyl) |

As shown in the Examples, the SPAA based compounds of the present disclosure are effective inhibitors of various PTPs. In some embodiments, the compounds disclosed herein can be used to inhibit mPTPA, mPTPB, LMWPTP, and Laforin with unprecedented potency and specificity. These PTPs are targets for the treatment of diseases associated with abnormal protein tyrosine phosphatase activity (such as tuberculosis, cancer, Lafora disease, and type 2 diabetes). Accordingly, the present disclosure also provides the use of the compounds of Formula 1, a therapeutically suitable prodrug thereof, or a therapeutically suitable salt thereof, as well as the compounds of Formula 2 disclosed herein as PTP inhibitors for treating these diseases.

In one aspect, the present disclosure provides a method of inhibiting a protein tyrosine phosphatase (FTP) selected from the group consisting of mPTPA, mPTPB, low molecular weight PTP (LMWPTP), and Laforin in a subject in need thereof, the method comprising administering to the subject a therapeutically effective amount of the compound of Formula 1a, a therapeutically suitable prodrug thereof, or a therapeutically suitable salt thereof, or the compound of Formula 2.

In another aspect, the present disclosure provides a method of treating tuberculosis in a subject in need thereof, the method comprising administering to the subject a therapeutically effective amount of the compound of Formula 1a, a therapeutically suitable prodrug thereof, or a therapeutically suitable salt thereof, or the compound of Formula 2.

In another aspect, the present disclosure provides a method of treating a cancer in a subject in need thereof, the method comprising administering to the subject a therapeutically effective amount of the compound of Formula 1a, a therapeutically suitable prodrug thereof, or a therapeutically suitable salt thereof, or the compound of Formula 2. In some embodiments, the cancer can be one selected from the group consisting of breast cancer, colon cancer, bladder cancer, and kidney cancer.

In another aspect, the present disclosure provides a method of treating Lafora disease in a subject in need thereof, the method comprising administering to the subject a therapeutically effective amount of the compound of Formula 1a, a therapeutically suitable prodrug thereof, or a therapeutically suitable salt thereof, or the compound of Formula 2.

In another aspect, the present disclosure provides a method of treating type 2 diabetes in a subject in need thereof, the method comprising administering to the subject a therapeutically effective amount of the compound of Formula 1a, a therapeutically suitable prodrug thereof, or a therapeutically suitable salt thereof, or the compound of Formula 2.

In another aspect, the present disclosure provides a method of inhibiting SHP2 in a subject in need thereof, the method comprising administering to the subject a therapeutically effective amount of the compound of Formula 3, a therapeutically suitable prodrug thereof, or a therapeutically suitable salt thereof.

In another aspect, the present disclosure provides a method of treating cancer in a subject in need thereof, the method comprising administering to the subject a therapeutically effective amount of the compound of Formula 3, a therapeutically suitable prodrug thereof, or a therapeutically suitable salt thereof. In some embodiments, the cancer can be one selected from the group consisting of breast cancer, lung cancer, colon cancer, prostate cancer, neuroblastoma, glioblastoma, melanoma, hepatocellular carcinoma, and leukemia.

Some subjects that are in specific need of treatment for disease and conditions as discussed above (e.g., tuberculosis, cancer, Lafora disease, type 2 diabetes) may include subjects who are susceptible to, or at elevated risk of, experiencing tuberculosis, cancer (e.g., breast cancer, lung cancer, colon cancer, prostate cancer, neuroblastoma, glioblastoma, melanoma, hepatocellular carcinoma, and leukemia), Lafora disease, type 2 diabetes, and the like. Subjects may be susceptible to, or at elevated risk of, experiencing tuberculosis, cancer, Lafora disease, type 2 diabetes due to family history, age, environment, and/or lifestyle. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

In another aspect, the present disclosure provides a pharmaceutical composition comprising a compound of Formula 1a, a therapeutically suitable prodrug thereof, or a therapeutically suitable salt thereof, or the compound of Formula 2 and a pharmaceutically acceptable carrier.

In another aspect, the present disclosure provides a pharmaceutical composition comprising a compound of Formula 3, a therapeutically suitable prodrug thereof, or a therapeutically suitable salt thereof, and a pharmaceutically acceptable carrier.

Representative pharmaceutical formulations include those suitable for oral, parenteral (including subcutaneous, intradermal, intramuscular and intravenous) and rectal administration. The formulations may be presented in unit dosage form and may be prepared by any of the methods well known in the art of pharmacy. Usually, the formulations are prepared by uniformly and intimately bringing into association the active ingredient with a liquid carrier, or a finely divided solid carrier, or both, and then, if necessary, forming the associated mixture into the desired formulation.

As used herein, the phrase "pharmaceutically acceptable" refers to those ligands, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, formulation or vehicle, such as a liquid or solid filler, diluent, excipient, solvent or encapsulating material, involved in carrying or transporting the active compound from one organ or portion of the body, to another organ or portion of the body. Each carrier must be "acceptable" in the sense of being compatible with the other components of the formulation and not injurious to the subject. Lyophilized formulations, which may be reconstituted and administered, are also within the scope of the present disclosure.

Pharmaceutical formulations suitable for oral administration may be presented as discrete units, such as a capsule, cachet, tablet, or lozenge, each containing a predetermined amount of the active ingredient; as a powder or granules; as a solution or a suspension in an aqueous liquid or a non-aqueous liquid such as a syrup, elixir or a draught, or as an oil-in-water liquid emulsion or a water-in-oil liquid emulsion. The formulation may also be a bolus, electuary or paste.

A tablet may be made by compressing or molding a pharmaceutical compound with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating agent and/or a surface active agent. Molded tablets may be prepared by molding in a suitable machine a mixture of the powdered active ingredient moistened with an inert liquid diluent. The tablets may optionally be coated or scored and may be formulated so as to provide slow or controlled release of the active ingredient.

Formulations suitable for parenteral administration include aqueous and non-aqueous sterile injection solutions, and may also include an antioxidant, buffer, a bacteriostat and a solution which renders the composition isotonic with the blood of the recipient, and aqueous and non-aqueous sterile suspensions which may contain, for example, a suspending agent and a thickening agent. The formulations may be presented in single unit-dose or multi-dose containers, and may be stored in a lyophilized condition requiring the addition of a sterile liquid carrier prior to use.

The compounds are administered in a therapeutically effective amount to provide treatments of the above-described diseases and disorders. The phrase "therapeutically effective amount" of the compound of the disclosure means a sufficient amount of the compound to treat disorders, at a reasonable benefit/risk ratio applicable to any medical treatment. It can be understood, however, that the total daily usage of the compounds of the disclosure can be decided by the attending physician within the scope of sound medical judgment. The specific therapeutically effective dose level for any particular patient can depend upon a variety of factors including the disorder being treated and the severity of the disorder, activity of the specific compound employed; the specific pharmaceutical composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Actual dosage levels of compounds in the pharmaceutical compositions of this disclosure can be varied so as to obtain an amount of the compound(s) that is effective to achieve the desired therapeutic response for a particular patient, compositions and mode of administration. The selected dosage level can depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

Materials and General Procedures.

p-Nitrophenyl phosphate (pNPP) was purchased from Fluke Co. Dithiothreitol (DTT) was provided by Fisher (Fair Lawn, N.J.). For organic synthesis, reagents were used as purchased (Aldrich, Acros, Alfa Aesar, TCI) except where noted. $^1$H and $^{13}$C NMR spectra were obtained on a BrukerAvance II 500 MHz NMR spectrometer with TMS or residual solvent as standard. Mass spectra were obtained using an Agilent Technologies 6130 quadrupole LC/MS. HPLC purification was carried out on a Waters Delta 600 equipped with a Sunfire Prep C18 OBD column (30 mm, 150 mm, 5 μm) with methanol-water (both containing 0.1% TFA) as mobile phase (gradient: 50-100% methanol, flow 10 mL/min). The purity of all final tested compounds was established to be >95% Agilent Technologies 6130 quadrupole LC/MS by using methanol-water (both containing 0.1% TFA) as the mobile phase (gradient: 30-100% methanol, flow 1.0 mL/min), with UV monitoring at the fixed wavelength of 254 nm.

Representative Procedure for the Synthesis of Products.

To α-Sulfo α-phenyl acetyl chloride (0.234 g, 1 mmol) and DIEA (0.522 mL, 3 mmol) in DMF (2 mL) was added propyl amine (0.09 mL, 1.1 mmol), and the mixture was stirred at room temperature for 1 hour. After quenching with water, it was subjected to HPLC purification, and product 5 (L319N01) was obtained as colorless oil (93% yield, >95% purity). $^1$H NMR (500 MHz, CDCl3) δ 8.23 (s, 1H), 7.45-7.44 (m, 2H), 7.27-7.20 (m, 3H), 4.42 (s, 1H), 3.11-3.02 (m, 2H), 1.46-1.39 (m, 2H), 0.85 (t, J=7.4 Hz, 3H); $^{13}$C NMR (500 MHz, CDCl3) δ 167.3, 135.7, 129.6, 127.4, 126.8, 71.5, 40.4, 22.3, 11.4. ESI-MS cacld. for $C_{11}H_{16}NO_4S$ (M+H+): m/z 258.1; found 258.0.

Library Synthesis in 96-Well Plate.

To each well of a 96-well plate was added 4 (20 μL, 20 mM in DMF), HBTU (20 μL, 20 mM in DMF), HOBt (20 μL, 20 mM in DMF) and DIEA (20 μL, 75 mM in DMF). Five minutes later, various amines (1 μL, 500 mM in DMF) were added. The plate was allowed to stand at room temperature overnight to give products in stock solutions at 4 mM (assuming the product is obtained at 80% yield).

Protein Expression and Purification; Kinetic Parameters Determination; and Inhibition Study.

These procedures are carried out according to previously reported methods (Combs, J. Med. Chem. 2010, 53, 2333-2344; Thareja et al., Med. Res. Rev. 2011, early view).

Expression and Purification of Recombinant mPTPB:

pET28b-mPTPB (from Dr. Christoph Grunder, University of California, Berkeley) was used to transform into E. coli BL21/DE3 and grown in LB medium containing 50 μg/ml kanamycin at 37° C. to an OD600 of 0.5. Following the addition of IPTG to a final concentration of 20 μM, the culture was incubated at 20° C. with shaking for an additional 16 hours. The cells were harvested by centrifugation at 5000 rpm for 5 minutes at 4° C. The bacterial cell pellets were resuspended in 20 mM Tris, pH 7.9, 500 mM NaCl, 5 mM imidazole, and were lysed by passage through a French press cell at 1,200 p.s.i. twice. Cellular debris was removed by centrifugation at 16,000 rpm for 30 minutes at 4° C. The protein was purified from the supernatant using standard procedures of Ni-nitrilotriacetic acid-agarose (Qiagen) affinity purification. The protein eluted from Ni-NTA column was concentrated with an Amicon Ultra centrifugal filter device (Millipore), and the buffer was changed to 20 mM Tris, pH 7.5, 150 mM NaCl, 1 mM EDTA and 1 mM DTT. Protein concentration was determined using the Bradford dye binding assay (Bio-Rad) diluted according to the manufacturer's recommendations with bovine serum albumin as standard. The purified mPTPB were made to 20% glycerol and stored at −20° C.

Kinetic Characterization of mPTPB Inhibitors:

The inhibition assays were performed at 25° C. in 50 mM 3,3-dimethylglutarate buffer, pH 7.0, containing 1 mM EDTA with an ionic strength of 0.15M adjusted by NaCl. The salicylic acid based library was screened in a 96-well format at 1 μM compound concentration. The reaction was started by the addition of 5 μl of the enzyme to 195 μl of reaction mixture containing 2.5 mM (the Km value) of pNPP and various concentrations of the inhibitor. The reaction was quenched after 5 minutes by the addition of 50 μl of 5N NaOH, and then 200 μl of reaction mixture was transferred to a 96-well plate. The absorbance at 405 nm was detected by a Spectra MAX340 microplate spectrophotometer (Molecular Devices). $IC_{50}$ values were calculated by fitting the absorbance at 405 nm versus inhibitor concentration to the following equation:

$$A_I/A_0 = IC_{50}/(IC_{50}+[I])$$

where $A_I$ is the absorbance at 405 nm of the sample in the presence of inhibitor; $A_0$ is the absorbance at 405 nm in the absence of inhibitor, and [I] is the concentration of the inhibitor.

The inhibition constants (Ki) for the inhibitor for mPTPB were determined at pH 7.0 and 25° C. The mode of inhibition and Ki value were determined in the following manner. at various fixed concentrations of inhibitor (0-3 Ki), the initial rate at a series of pNPP concentrations was measured by following the production of p-nitrophenol as describe above, ranging from 0.2- to 5-fold the apparent Km values. The data were fitted SI-23 to appropriate equations using SigmaPlot-Enzyme Kinetics to obtain the inhibition constant and to assess the mode of inhibition. For selectivity studies, the PTPs, including mPTPA, YopH, CD45, FAP-1, HePTP, Lyp, PTP1B, SHP1, SHP2, and VHX were expressed and purified from E. coli. The inhibition assay for these PTPs were performed under the same conditions as mPTPB except using a different pNPP concentration corresponding to the $K_m$ of the PTP studied.

Cellular Studies:

Raw264.7 mouse macrophages were cultured in Dulbecco's modified Eagle's medium (DMEM) supplemented with 10% FBS (Invitrogen), penicillin (50 units/mL), and streptomycin (50 μg/mL) under a humidified atmosphere containing 5% $CO_2$ at 37° C. Transfected Raw264.7 cells (Vector, WT-mPTPB) were seeded in a 12-well plate at a density of $4 \times 10^4$ cells/well. The following day cells were treated with mPTPB inhibitor 11a for 1 hour, then stimulated with IFN-γ (200 U/ml) for 1 hour. Subsequently, the cells were washed with ice-cold phosphate buffered saline, and lysed with lysis buffer on ice for 30 minutes. Cell lysate was then cleared by centrifuging at 13,000 rpm for 15 minutes. The phosphorylation of ERK1/2 was detected by Western blotting.

Example 1

Construction of SPAA Based Focused Library.

Figure 2:
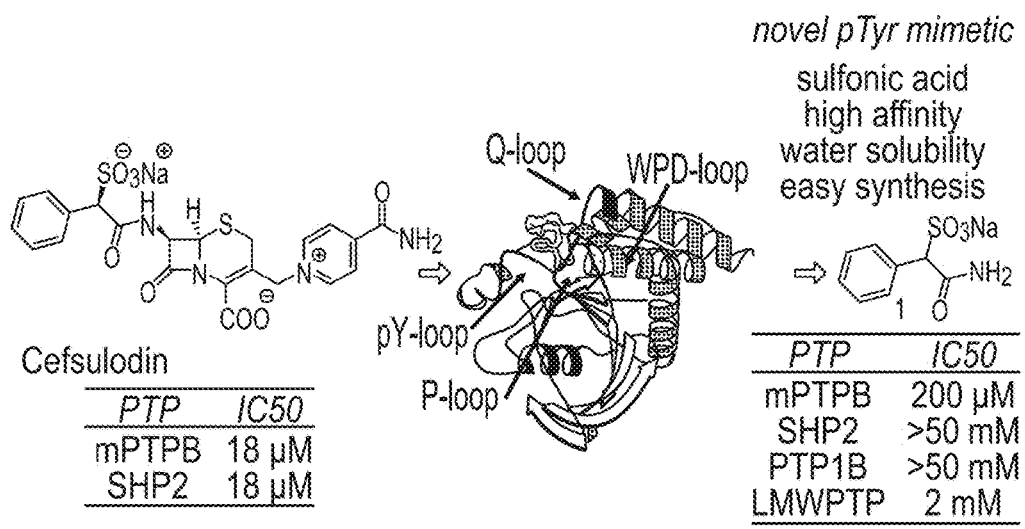
FIG. 2 depicts the crystal structure of SHP2-bound cefsulodin and α-sulfophenylacetic amide (SPAA) as a novel pTyr mimetic.

Previously, cefsulodin (a β-lactam antibiotics, structure shown in FIG. 2) was identified as an inhibitor of mPTPB. The crystal structure of SHP2-cefsulodin complex shows that sulfonic acid is in close proximity with the PTP signature motif, the α-phenyl group forms a π-π interaction with P loop residue Phe, indicating the nature of SPAA as pTyr mimetic (FIG. 2). Without being bound by any theory, it is believed that SPAA is completely different from conventional pTyr mimetics (such as F2PMP, salicylic acid, etc.), in which the acid group and additional fragment are located on opposite sides of the benzene ring (FIG. 1). For SPAA, however, the additional fragment needs to be extended from the same side of the benzene ring as the acid group. This would have been considered as a disruption to the binding due to the valley shape of the PTP active site, thus would have been avoided during the design of a conventional PTP inhibitor.

Surprisingly, it has been found that the amide group in cefsulodin does not disrupt the binding of sulfonic acid and PTP signature motif but instead extends out from the pocket and forms hydrogen bonds with active site entrance residues. In addition, SPAA, the sulfonic acid based pTyr mimetic, has been shown to have high affinity to mPTPB and LMWPTP ($IC_{50}$=200 μM, and 2 mM, respectively), good water solubility (>100 mg/mL), and it is commercially available and inexpensive.

PTPα, the dual specificity phosphatases MKP3, VHR, VHX, CDC14A, CDC25A, LMWPTP, bacterial PTPs mPTPA, and mPTPB, and SSU72. The screening concentrations were initially set at 10 μM for each PTP, and were reduced to 1 μM and 0.1 μM if the inhibition scores were high for certain PTPs. Top and selective hits were resynthesized by this method and purified by reversed phase HPLC to >95% pure. The $IC_{50}$ of these compounds against a panel of PTPs were measured, as is summarized in Table 9.

TABLE 9

$IC_{50}$ values of mPTPB inhibitors against a panel of PTPs

| $IC_{50}$ (μM) | L319M34 | L319M52 | L319M54 | L319N15 | L319N22 | L319N46 | L319N47 | L319N53 |
|---|---|---|---|---|---|---|---|---|
| mPTPB | 0.055 | 0.106 | 0.078 | 0.116 | 0.203 | 0.060 | 0.009 | 0.020 |
| mPTPA | 0.196 | 0.56 | 0.265 | 0.194 | 0.972 | >200 | 11.3 | >200 |
| LMWPTP | 5.29 | 72.27 | 7.96 | 7.33 | 6.39 | >200 | 115 | >200 |
| Laforin | 4.05 | 5.08 | 4.25 | 2.1 | 27 | >200 | 61 | >200 |
| YopH | >200 | >200 | >200 | >200 | >200 | >200 | 160 | >200 |
| TbPTP1 | >200 | 118 | >200 | >200 | >200 | >200 | 38 | >200 |
| PTP1B | >200 | >200 | >200 | >200 | >200 | >200 | 145 | >200 |
| TcPTP | >200 | 170 | >200 | >200 | >200 | >200 | 160 | >200 |
| LYP | >200 | >200 | >200 | >200 | >200 | >200 | 42 | >200 |
| PEST | 72.3 | 77 | >200 | 43.5 | 67 | >200 | 42 | >200 |
| SHP1 | >200 | >200 | >200 | >200 | >200 | >200 | 66 | >200 |
| SHP2 | >200 | >200 | >200 | >200 | >200 | >200 | 76 | >200 |
| HePTP | >200 | 130 | >200 | 50 | 94 | >200 | 77 | >200 |
| Meg2 | >200 | >200 | >200 | >200 | >200 | >200 | 147 | >200 |
| PTPH1 | >200 | >200 | >200 | >200 | >200 | >200 | 30 | >200 |
| FAP1 | >200 | 88 | 180 | 34 | 76 | >200 | 21 | 76 |
| CD45 | >200 | >200 | >200 | >200 | >200 | >200 | 140 | >200 |
| LAR | >200 | >200 | >200 | >200 | >200 | >200 | >200 | >200 |
| PTPα | >200 | >200 | >200 | >200 | >200 | >200 | >200 | >200 |
| PTPβ | >200 | >200 | >200 | >200 | >200 | >200 | 50 | >200 |
| PTPγ | >200 | >200 | >200 | >200 | >200 | >200 | 180 | >200 |
| PTPσ | >200 | >200 | >200 | >200 | >200 | >200 | >200 | >200 |
| PTPε | >200 | >200 | >200 | >200 | >200 | >200 | >200 | >200 |
| PTPμ | >200 | >200 | >200 | >200 | >200 | >200 | >200 | >200 |
| STEP | >200 | >200 | >200 | >200 | 140 | >200 | >200 | >200 |
| MKP3 | >200 | >200 | >200 | >200 | >200 | >200 | >200 | >200 |
| VHR | >200 | >200 | >200 | >200 | >200 | >200 | 99 | >200 |
| VHX | 92 | 170 | >200 | >200 | >200 | >200 | 150 | >200 |
| VHZ | >200 | >200 | >200 | >200 | >200 | >200 | 80 | >200 |
| CDC14A | >200 | >200 | >200 | >200 | >200 | >200 | >200 | >200 |
| PP5 | >200 | >200 | >200 | >200 | >200 | >200 | >200 | >200 |
| Ssu72 | >200 | 97.6 | >200 | 69 | 83 | >200 | >200 | >200 |

Figure 4:
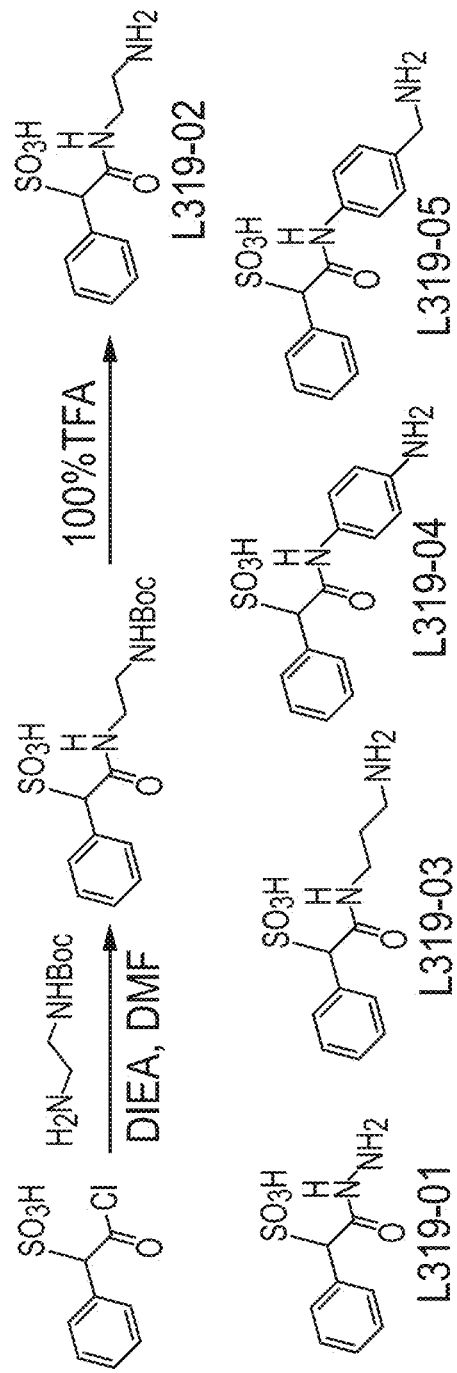
FIG. 4 is a scheme depicting the synthesis of precursors for construction of the library of FIG. 3A.
Figure 5:
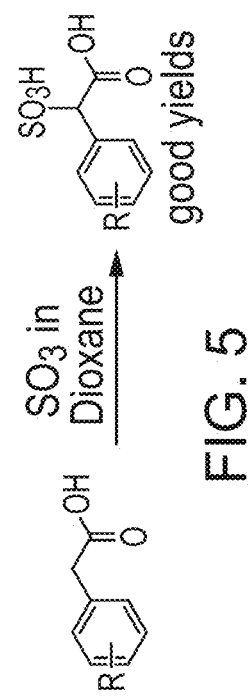
FIG. 5 is a scheme depicting the synthesis of precursors for construction of the library of FIG. 3B.
Figure 6:
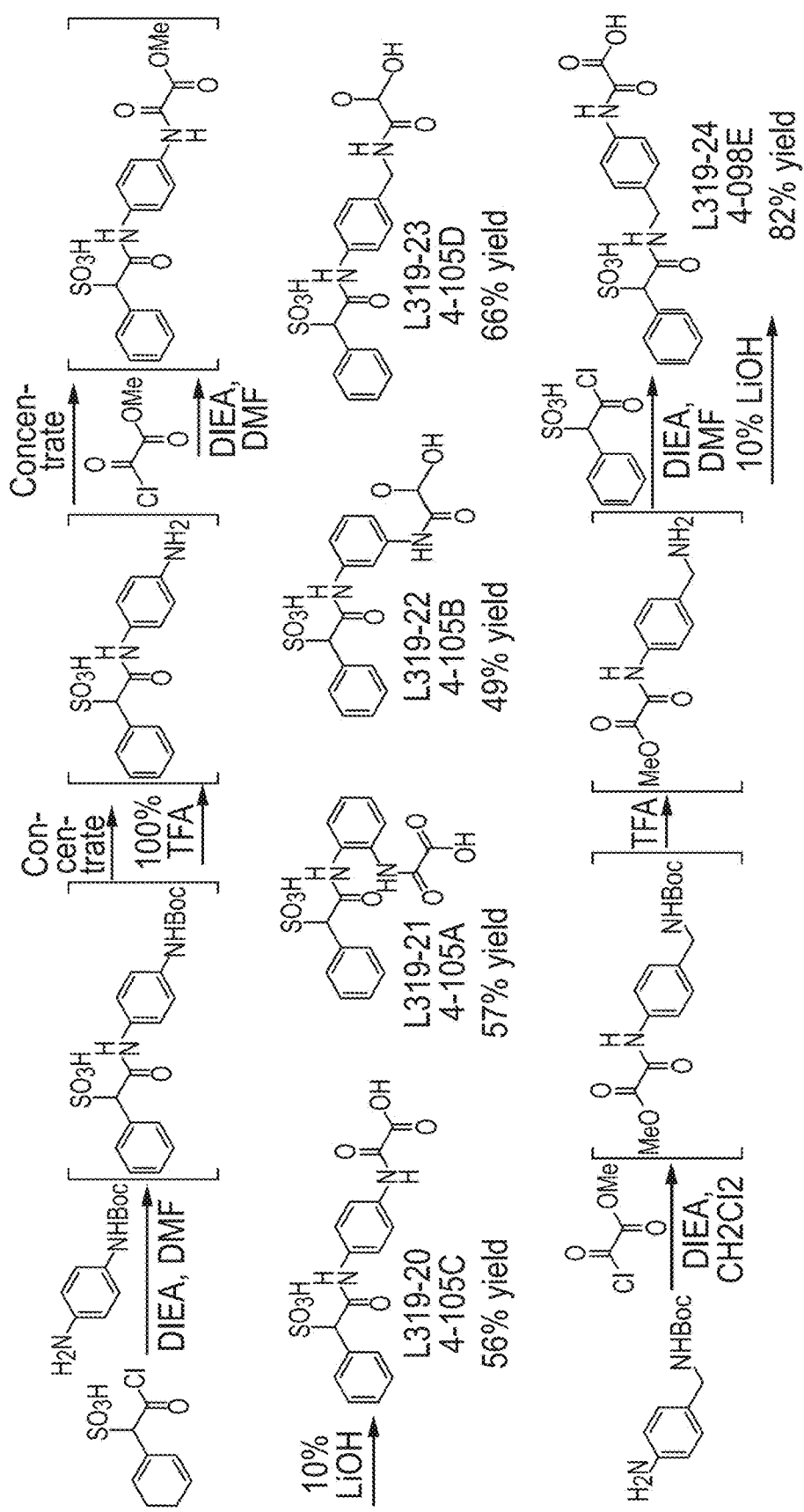
FIG. 6 is a scheme depicting the synthesis of precursors for construction of the library of FIG. 3C.

To demonstrate the utility of these novel pTyr mimetics as potent and selective PTP inhibitors, 3 libraries of compounds were designed to link SPAA with either a set of carboxylic acids or amines (FIGS. 3A-3C). The synthesis processes of the precursors for each library are shown in FIGS. 4-6, respectively.

Amide/peptide bond formation is an efficient and reliable method for library constructions; and it allows the use of the most common and commercially available amines and carboxylic acids as reactants. In practice, all carboxylic acid and amine building blocks of Sigma-Aldrich, and selected representative 192 carboxylic acids and 192 amines with low molecular weight covering almost all the chemo types from their collections were examined. The library was assembled directly on 96-well plates by standard HBTU peptide coupling conditions. The wells from each plate were monitored by LC-MS, which indicated the production of various compounds from the reactions. Thus, a total of 5184 pTyr mimetic compounds were obtained with molecular weights from 200 to 700. These compounds were immediately subjected to screening against a panel of PTP enzymes, including cytosolic PTPs, PTP1B, TC-TP, SHP2, LYP, HePTP, and FAP1, the receptor-like PTPs, CD45, LAR, and Example 2

Potent and Specific Inhibition of mPTPB.

SPAA based compounds from the libraries were studied as inhibitors against mPTPB, a virulence factor of Mtb strain and a novel drug target of tuberculosis (TB).

Compound L319N47 demonstrated an $IC_{50}$ of 9 nM against mPTPB, a 2000-fold increase in potency compared to SPAA, (Tables 1 and 9). L319N47 also demonstrated a 1000-fold preference for mPTPB over mPTPA ($IC_{50}$=11.3 μM) and a greater than 2000-fold preference for mPTPB over 30 other PTPs (e.g. LMWPTP, $IC_{50}$=115 μM), including cytosolic PTPs, PTP1B, TC-TP, SHP2, Lyp and FAP1, the receptor-like PTPs, CD45, LAR, and PTPα, the dual specificity phosphatases VHR, VHX, CDC14A, and the LMWPTP.

L319N46 and L319N53 ($IC_{50}$=60 and 20 nM, respectively) were slightly less active than L319N47. However, they demonstrated even higher specificity towards mPTPB. For example, L319N53 exhibited a greater than 10000-fold selectivity over any PTP tested. It is believed that any previously reported inhibitors of PTP, including mPTPB, possesses no more than 100-fold specificity (see, for example, Noren-Muller et al., Proc. Natl. Acad. Sci. USA 2006, 103, 10606-10611; Correa et al., Chem. Asian J. 2007, 2, 1109-1126; Noren-Muller et al., Angew. Chem. Int. Ed. 2008, 47, 5973-5977; Weide et al., Bioorg. Med. Chem. Lett. 2006, 16, 59-63; Soellner et al., J. Am. Chem. Soc. 2007, 129, 9613-9615; Grundner et al., Structure 2007, 15, 499-509; Tan et al., Org. Lett. 2009, 11, 5102-5105; Chen et al., ACS Med. Chem. Lett. 2010, 1, 355-359; Vintonyak et al., Angew. Chem. Int. Ed. 2010, 49, 5902-5905), suggesting that the potency and specificity of the compounds described herein are unprecedented.

Remarkably, L319N46, L319N47, and L319N53 share a common heterocyclic structure, which includes the nitrogen atom in the amide group, adjacent to the pTyr mimetic (i.e. the Ph-CH($SO_3$H)— group). For L319N46 and L319N47, the heterocyclic structure comprises a piperidine moiety; for L319N53, the heterocyclic structure comprises a decahydroquinoline moiety (Table 1). Without being bound by any theory, it is hypothesized that a structure-activity relationship underlies the exceptional potency and specificity of these three compounds. It is further hypothesized that the compact structures, low molecular weights (MW about 400), and watersolubility (>10 mg/mL) are among the factors that contribute to their drug-likeness. These results indicate that SPAA-based compounds L319N46, L319N47, and L319N53 are currently the most potent and specific inhibitors of mPTPB, allowing for the development of new tuberculosis (TB) agents targeting mPTPB.

Example 3

General Procedures for the Preparation of Inhibitors.

Reagents were used as purchased from Sigma-Aldrich and Fisher Scientific. $^1$H and $^{13}$C NMR spectra were obtained on a BrukerAvance II 500 MHz NMR spectrometer with tetrame-thylsilane or residual solvent as standard. Mass spectra were obtained using an Agilent Technologies 6130 quadrupole LC/MS. HPLC purification was carried out on a Waters Delta 600 equipped with a Sunfire Prep C18 OBD column (30 mm/150 mm, 5 μm) with methanol-water (both containing 0.1% TFA) as the mobile phase (gradient: 50-100% methanol, flow 10 mL/min). The purity of all final tested compounds was established to be >95% by Agilent Technologies 6130 quadrupole LC/MS by using methanol-water (both containing 0.1% TFA) as the mobile phase (gradient: 0-100% methanol, flow 1.0 mL/min), with UV monitoring at the fixed wavelength of 254 nm.

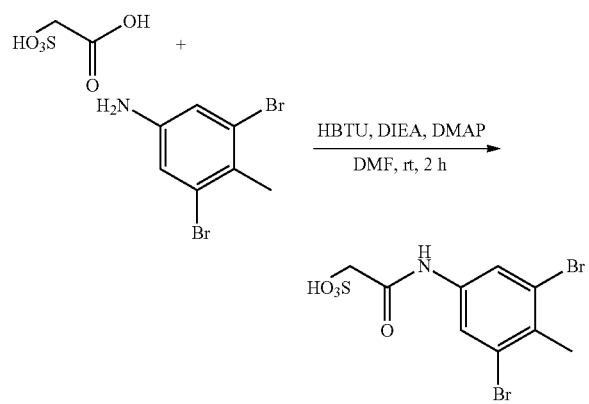

Synthesis of L335-M34 (mPTPA).

To a round-bottom flask were added sulfoacetic acid (0.14 g, 1.0 mmol), DMF (5 mL), HBTU (0.379 g, 1 mmol), 3,5-dibromo-4-methylaniline (0.265 g, 1 mmol), DIEA (0.52 mL, 3 mmol), and DMAP (0.012 g, 0.1 mmol). The mixture was stirred at room temperature for 2 hours, and then it was subjected to reversed-phase HPLC purification to give product L335-M34 as a white solid (0.385 g, 99% yield): 1H NMR (500 MHz, DMSO) δ 10.08 (s, 1H), 7.87 (s, 2H), 3.52 (s, 2H), 2.42 (s, 3H); $^{13}$C NMR (DMSO) δ 164.6, 138.9, 130.5, 124.1, 121.8, 59.1, 22.6; ESI-HRMS calcd for $C_9H_{10}Br_2NO_4S$ (M+H$^+$) 385.8692, found 385.8696.

Kinetic Analysis of mPTPA Inhibition.

The phosphatase activity of mPTPA was assayed using p-nitrophenyl phosphate (pNPP) as a substrate at 25° C. in 50 mM 3,3-dimethylglutarate buffer, pH 7.0, containing 1 mM EDTA with an ionic strength of 0.15 M adjusted by NaCl. The reaction was started by the addition of 50 L of the enzyme to 150 L of reaction mixture containing pNPP and various concentrations of the inhibitor in a 96-well plate. The final concentration for mPTPA was 5 nM. The final concentration for pNPP was 1 mM, which was the Km value for mPTPA. The reaction was quenched after 15 minutes by the addition of 50 L of 5 N NaOH, and then 200 L of reaction mixture was transferred to a 96-well plate. The non-enzymatic hydrolysis of pNPP was corrected by measuring the control without the addition of enzyme. The amount of product p-nitrophenol was determined from the absorbance at 405 nm detected by a SpectraMax 384PLUS microplate spectrophotometer (Molecular Devices) using a molar extinction coefficient of 18000 $M^{-1}$ $cm^{-1}$. $IC_{50}$ values were calculated by fitting the absorbance at 405 nm versus inhibitor concentration to the following equation:

$$A_I/A_0 = IC_{50}/(IC_{50}+[I])$$

where $A_I$ is the absorbance at 405 nm of the sample in the presence of inhibitor, $A_0$ is the absorbance at 405 nm in the absence of inhibitor, and [I] is the concentration of the inhibitor.

For selectivity studies, the PTPs, including mPTPB, PTP1B, TC-PTP, SHP1, SHP2, FAP1, Lyp, PTP-MEG2, HePTP, PTPa, LAR, CD45, PTPg, VHR, Laforin, VHX, Cdc14A, and the low molecular weight PTP, were expressed and purified from E. coli. The final concentration for all PTPs was 5 nM. The inhibition assay for these PTPs was performed under the same conditions as mPTPA except using a different pNPP concentration corresponding to the Km of the PTP studied. Inhibitor concentrations used for $IC_{50}$ measurements cover the range from 0.2 to 5× of the $IC_{50}$ value.

Mycobacterium Tuberculosis Strains.

The Johns Hopkins Center for Tuberculosis Research laboratory reference strain Mtb H37Rv was passaged twice through mice and frozen in aliquots at −80° C. before use. Aliquots were thawed and grown to logarithmic phase (optical density at 600 nm=0.6) in Middlebrook 7H9 broth (Difco Laboratories, Detroit, Mich.) supplemented with 10% OADC (Becton Dickinson), 0.05% Tween, and 0.1% glycerol prior to aerosol infection.

Animals.

Female guinea pigs (273±20.91 g) with and without jugular vein catheters were purchased from Charles River Laboratories (Wilmington, Mass.). The animals were maintained under specific pathogen-free conditions and fed water and chow ad libitum. All procedures followed protocols approved by the Institutional Animal Care and Use Committee at the Johns Hopkins University School of Medicine.

In Vitro Anti-Mtb Assays.

Alamar Blue Assay. A colorimetric, microplate-based Alamar Blue assay (MABA) method was used to determine the MICs of mPTPA/B against *M. tuberculosis* isolates. Briefly, cultures were incubated at 37° C. without shaking in 96-well plates. Alamar Blue reagent (Invitrogen) was added at 1:5 v/v prior to readout 24 hours later using a Fluostar Optima fluorescence plate reader (BMG Labtech), equipped with a 544 nm excitation filter and a 590 nm emission filter.

Macrophage Assays.

Inhibition of growth of *M. tuberculosis* (Erdman and H37Rv) in a macrophage cell culture was assessed as described in Zhou et al., Proc. Natl. Acad. Sci. U.S.A. 107, 4573-4578. Following activation with 50 U/mL IFN-γ (Sigma, 087k1288), J774 macrophages were infected with *M. tuberculosis* strain at a multiplicity of infection of 1:1 for 1 hour, washed, and incubated with 20 g/mL amikacin containing DMEM before adding the test compounds. Cells were washed and lysed, and different dilutions were plated on 7H11 agar plates. Colonies were counted after 3 weeks of incubation at 37° C.

Pharmacokinetics and Bioavailability Studies.

Separate groups of three catheterized guinea pigs each were given (i) a single dose of L01-Z08 at 20 mg/kg or L335-M34 at 50 mg/kg of body weight (structures shown in Table 11); (ii) L01-Z08 at 20 mg/kg and L335-M34 at 50 mg/kg were given together to test for possible drug-drug interactions that might alter the uptake and/or clearance of one or both of the compounds. All drugs were suspended in 1% DMSO, 0.5% DEA, 48.5% PEG 400, and 50% water. Blood was collected for analysis of these drugs in plasma pre-dose and at 1, 4, 8, 24, and 48 h post-dose. Plasma was separated and stored at −70° C. until analysis. Plasma drug concentrations were determined by liquid chromatography-mass spectrometry and liquid chromatography-tandem mass spectrometry over the concentration range of 0.005-1 mg/L with dilution to 10 mg/L. Pharmacokinetic variables were calculated from individual drug concentration-time data using non-compartmental methods as implemented in WinNonlin version 5.0 (Pharsight, Mountain View, Calif.) as described earlier.

Aerosol Infections.

Log-phase cultures of Mtb H37Rv were diluted 500-fold (to ~$10^5$ bacilli/mL) in 1×PBS for aerosol infection of guinea pigs. A total of 73 guinea pigs were aerosol-infected with a Madison chamber aerosol generation device (College of Engineering Shops, University of Wisconsin, Madison, Wis.) calibrated to deliver approximately $10^2$ bacilli into guinea pig lungs, as described in Ahmad et al., J. Antimicrob. Chemother. 65, 729-734.

Antibiotic Treatment.

Beginning 28 days after aerosol infection, guinea pigs were randomized to different treatment and control groups. Guinea pigs were treated 5 days per week for 6 weeks, as indicated in Table 10. Isoniazid (INH, H; Sigma), rifampicin (RIF, R; Sigma), and pyrazinamide (PZA, Z; Sigma) were dissolved in sterile distilled water. A cocktail solution of HRZ was prepared weekly and kept at 4° C. Aarden compounds (L01-Z08 and L335-M34) were suspended in formulation and stored at room temperature for up to 1 week.

TABLE 10

| Regimen | Number of guinea pigs to sacrifice by time-point<br>Week −4 | Day 0 | Week 2 | Week 4 | Week 6 | Total |
|---|---|---|---|---|---|---|
| Untreated | 4 | 4 | 4 | 4 | 5 | 21 |
| HRZ | | | 4 | 4 | 5 | 13 |
| L01Z08 + HRZ | | | 4 | 4 | 5 | 13 |
| L335M34 + HRZ | | | 4 | 4 | 5 | 13 |
| L01Z08 + L335M34 + HRZ | | | 4 | 4 | 5 | 13 |
| Total | 4 | 4 | 20 | 20 | 25 | 73 |

TABLE 10-continued

Drugs are to be given at the following dosages in (mg/kg): Isoniazid (H), 60; Rifampin (R), 1000; Pyrazinamide (Z), 300; L01-Z08, 20; L335M34, 50; all drugs given 5 times weekly.

All animals were treated with a formulation consisting of 20% pumpkin (w/v) (Libby's 100% pure pumpkin) mixture supplemented with Vitamin C (50 mg/kg mean body weight) and commercial *lactobacillus* (BD lactinex) (all purchased from Walmart, Towson, Md.) to improve palatability and help stabilize the cecal flora, thereby preventing gastrointestinal dysbacteriosis or antibiotic-associated enteritis. Drug doses were administered in a final volume of 0.5 mL and were delivered in the posterior oropharynx by an automatic pipet with a disposable tip.

Study End Points.

Guinea pigs were sacrificed on the day after aerosol infection (day 27), on the day of treatment initiation (day 0), and at the indicated time points after treatment to determine the numbers of CFU implanted in the lungs, pretreatment baseline CFU counts, and the post-treatment CFU counts, respectively.

Animal body weights were recorded on a weekly basis, and lung and spleen weights were recorded at the time of necropsy. The lungs of each animal were examined at necropsy for grossly visible lesions, and random samples from the left caudal lung lobe were dissected, placed into 10% buffered formaldehyde, and paraffin embedded for histopathological staining with hematoxylin and eosin (H&E). At least one entire H&E-stained cross section per animal lung (4 animals/group) was analyzed for degree of inflammation. The surface area occupied by granulomatous inflammation was determined by ImageJ software-based morphometry of digitized images of lung sections, and results are represented as percentage of lung surface area involved.

The remaining lungs were homogenized in 10 mL of PBS, and homogenates were plated on 7H11 plates containing cycloheximide (50 mg/L), carbenicillin (100 mg/L), polymyxin B (200000 U/L), and trimethoprim (20 mg/L) and incubated for 28 days at 37° C. for CFU enumeration.

Statistical Analysis.

CFU data were derived from 4-5 animals per group. Log-transformed CFU were used to calculate means and standard deviations. Comparisons of data among experimental groups were performed by Student's t test. Group means were compared by one-way analysis of variance (ANOVA) with Dunnett's post-test (DO or untreated controls vs treatment groups) or Bonferroni comparison (all treatment groups), using GraphPad Prism version 4 (GraphPad, San Diego, Calif.). Values of $p<0.05$ were considered to be statistically significant.

Results and Discussion

Development of Potent and Selective mPTPA and mPTPB Inhibitors.

Therapeutic targeting of PTPs has historically been stalled by difficulties in achieving inhibitor selectivity and bioavailability. The highly conserved PTP active site presents considerable challenges in obtaining compounds that can selectively inhibit the target of interest without adversely hitting other PTPs. In order to accommodate phospho-substrates, the PTP active site is positively charged, which favors negatively charged molecules in high-throughput screening campaigns that suffer from poor cell membrane permeability. To address the selectivity issue, a novel paradigm was developed for the acquisition of potent and selective PTP inhibitors by targeting both the PTP active site and unique pockets in the vicinity of the active site. To address the bioavailability issue, the existing natural product and FDA-approved drug space was explored for previously unknown PTP inhibitory activities since these molecules already possess acceptable pharmacological properties. Benzofuran salicylic acid was previously identified as a privileged pharmacophore for mPTPB. Using a fragment-based medicinal chemistry approach, the benzofuran salicylic acid core was transformed herein into a highly potent and selective mPTPB inhibitor (L01-Z08, Table 11) with excellent in vivo efficacy.

Figure 7:
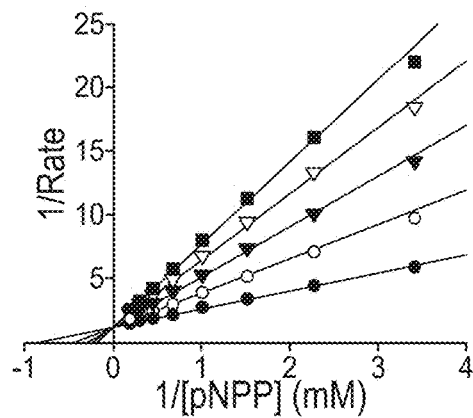
FIG. 7 depicts Compound L335-M34 as a reversible and competitive inhibitor of mPTPA with pNPP as a substrate. Lineweaver-Burk plot for L335-M34-mediated mPTPA inhibion. Compound L335-M34 concentrations were 0 (●), 50 (○), 100 (Δ), 150 (▼), and 200 nM (■). The $K_i$ value of 56±2.0 nM was determined from three independent measurements.

Kinetic analysis revealed that L335-M34 was a reversible and competitive inhibitor of mPTPA with a Ki of 56±2.0 nM (FIG. 7). To determine the specificity of L335-M34, its inhibitory activity toward mPTPB and a panel of mammalian PTPs was measured, including cytosolic PTPs, PTP1B, TC-PTP, SHP1, SHP2, FAP1, Lyp, PTP-Meg2, and HePTP, the receptor-like PTPs, PTPα, LAR, CD45, and PTPRG, the dual specificity phosphatases VHR, Laforin, VHX, and Cdc14A, and the low molecular weight PTP. As shown in Table 11, L335-M34 was highly selective for mPTPA, exhibiting greater than 20-fold selectivity over all PTPs examined. L335-M34 appears to represent the most potent and specific mPTPA inhibitor reported to date.

Cellular Activity of mPTPA and mPTPB Inhibitors L335-M34 and L01-Z08.

The mPTPA inhibitor L335-M34 was highly selective for its target, with an $IC_{50}$ of 160 nM against mPTPA, but no significant activity against mPTPB or a panel of human PTPs at concentrations below 3 μM. Because mPTPA is a secreted virulence factor that regulates host antibacterial responses rather than Mtb physiology, it was unsurprising that L335-M34 was devoid of activity in standard MIC assays; however, the compound was able to markedly

TABLE 11

Molecular and Cellular Properties of Lead mPTPA and mPTPB Inhibitors

| Structure | Name | Target | Biochemical potency against target ($Ic_{50}$, nM) mPTPA | mPTPB | Fold Selectivity vs. mPTPA/B | vs. PTP panel[a] | In vitro anti-Mtb activity (uM) MABA-MIC[b] H37Rv Erdman | Mtb-infected macrophages[c] |
|---|---|---|---|---|---|---|---|---|
| $HO_3S$-CH$_2$-C(=O)-NH-(3,5-dibromo-4-methylphenyl) | L335M34 | mPTPA | 160 | >3200 | >20 | >20 | >10 >10 | 1.38 |
| 2-phenyl-3-[(3-trifluoromethylphenyl)ethynyl]-benzofuran-5-carboxylic acid, 6-hydroxy | L01Z08 | mPTPB | 2500 | 38 | 66 | >37 | >10 >10 | <5 |

[a]Human PTP panel: PTP1B, TC-PTP, SHP1, SHP2, FAp1, Lyp, Meg2, HePTP, laforin, VHX, VHR, LMWPTP, Cdc14A, PTPα, LAR, CD45, PTPRG.
[b]MABA-MIC = microplate Alamar Blue assay for minimum inhibitory concentration.
[c]$IC_{90}$ in macrophages activated with interferon-γ.

More recently, it was discovered that cefsulodin, a third generation cephalosporin β-lactam antibiotic, exhibits inhibitory activity against a number of PTPs. Fragmentation analysis of cefsulodin identified α-sulfophenylacetic amide (SPAA) as an mPTP-inhibiting pharmacophore and a novel pTyr mimetic. Structure-guided and fragment-based optimization of SPAA led to compound L335-M34, which displayed an $IC_{50}$ value of 160 nM for mPTPA (Table 11).

decrease bacterial load in Mtb-infected macrophages at low micromolar concentrations (Table 11).

The L01 family comprises three highly active and selective mPTPB inhibitors. The selected lead compound from this series, L01-Z08, displayed a potency of 38 nM against mPTPB and was 66-fold less potent against mPTPA and at least 37-fold selective when screened against a panel of 17 human PTPs. Like the mPTPA inhibitor L335-M34, L01-

Z08 was inactive in the MIC assay but displayed potent anti-Mtb activity in J774A.1 macrophages (Table 11).

mPTPA and mPTPB Inhibitors are Bioavailable and Well-Tolerated in Guinea Pigs Following Oral Dosing.

Figure 8:
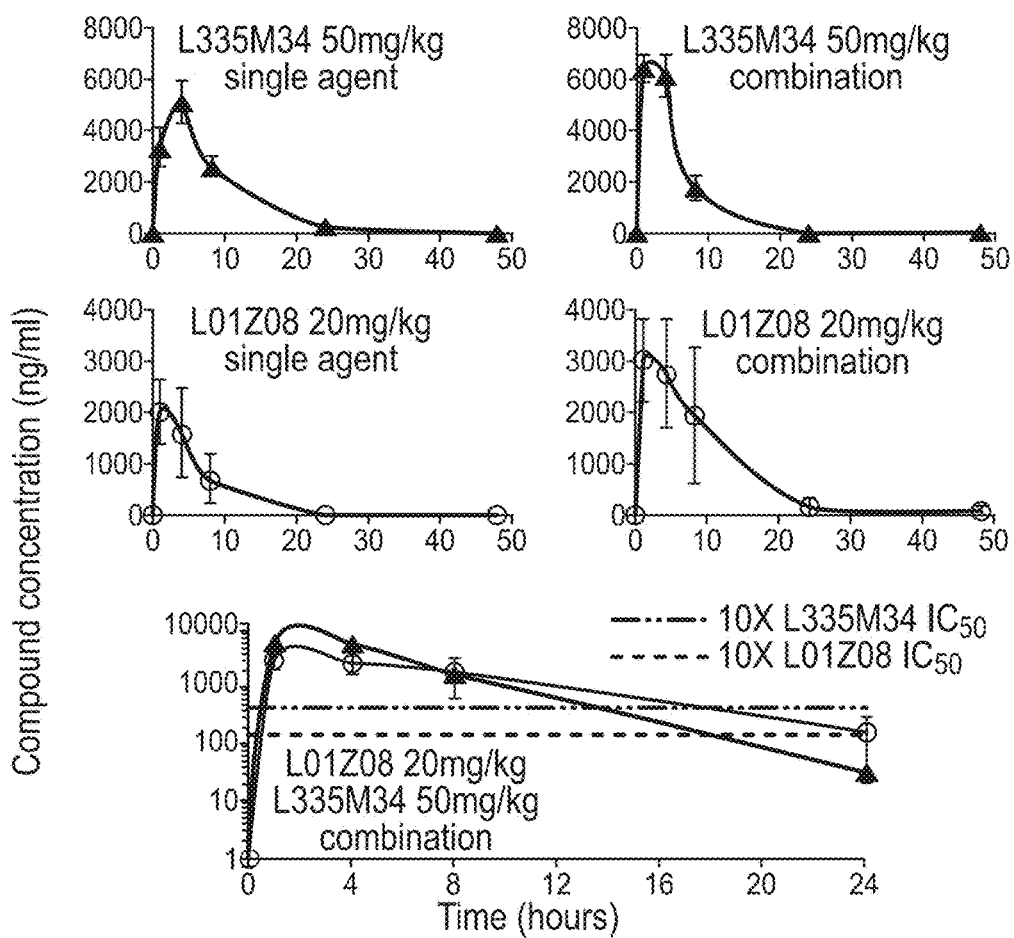
FIG. 8 depicts the pharmacokinetic profile of lead mPTP inhibitors in guinea pig plasma. Concentration of mPTP inhibitors in the plasma over time. L335-M34 (mPTPA) 50 mg/kg or L01-Z08 (mPTPB) 20 mg/kg was given orally once alone or in combination, and blood samples were collected at the indicated intervals relative to dosing. N=3 per time point; graph represents mean±SD values.

As shown in FIG. 8, L01-Z08 and L335-M34 showed good oral bioavailability and half-life in guinea pigs (Table 12). Both drugs were rapidly absorbed, reaching peak concentrations within a few hours with a typical biphasic plasma clearance curve. Because the drugs were to be co-formulated for oral delivery in the therapy study, a combination PK study was performed to confirm that they were amenable to co-administration. Co-formulating L01-Z08 with L335-M34 in a single dosing solution did not negatively affect uptake or clearance of either drug. In fact, the bioavailability of L335-M34 was affected only moderately; a slight increase in uptake rate led to a greater peak concentration, which was offset by somewhat more rapid clearance, so that the overall exposure ($AUC_{ALL}$) was essentially unchanged. By contrast, L01-Z08 exposure was enhanced by co-administration (both C, and beta-phase $T_{1/2}$ were elevated), but a reduction in the volume of distribution suggested that drug delivery to the tissues was probably not improved (Table 12). The PK study strongly indicated that the two compounds could be delivered with adequate efficiency in the guinea pig by the oral route. As shown in the bottom panel of FIG. 8, at the doses selected for use in the efficacy study, L335-M34 and L01-Z08 were detected at concentrations 10-fold in excess of their biochemical $IC_{50}$ values for 12-14 and 20-24 hours, respectively, suggesting that once daily oral dosing was an appropriate schedule for each drug. However, it should be noted that a higher degree of selectivity for these compounds was observed in the biochemical assays ($IC_{50}$) than in the whole-cell assays in macrophages (growth inhibition/$IC_{90}$), perhaps due to cell permeability issues.

−27, and the organisms multiplied to a peak burden of 6.11±0.15 $\log_{10}$ CFU (colony-forming units) on day 0 (time of treatment initiation). Thereafter, bacillary growth was controlled in the lungs of untreated guinea pigs, which had 5.82±0.17 $\log_{10}$ CFU in the lungs at the conclusion of this Example.

Figure 10A:
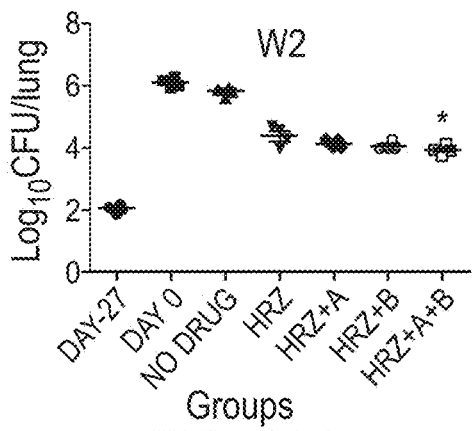
FIGS. 10A-10C depict the activity of adjunctive mPTPA and mPTPB inhibitors against chronic TB infection in guinea pigs. Animals were infected vi aerosol with ~$10^2$ CFU of $M.$ $tuberculosis$ H37Rv and were either left untreated or were treated with drugs beginning 4 weeks after infection. $Log_{10}$ CFU in the lungs are shown after 2 (FIG. 10A), 4 (FIG. 10B), and 6 (FIG. 10C) weeks of treatment. No drug=untreated, HRZ: isoniazid (H), 60/Rifampin (R), 100/pyrazinamide (Z), 300; mPTPA/A: L335M34, 50; mPTPB/B: L01-Z08, 20; numbers after each drug refer to doses (mg/kg); n=4 guinea pigs per time point; *p<0.05, p<0.01, *p<0.001, HRZ versus HRZ+A+B.

Following 2 weeks of treatment, all guinea pigs in the HRZ, HRZ+L335-M34 (A), HRZ+L01-Z08 (B), and HRZ+AB groups were able to contain Mtb multiplication in the lungs, resulting in mean bacillary burdens of 4.44±0.31, 4.07±0.15, 4.15±0.17, and 3.77±0.21 $\log_{10}$, respectively. After 2 weeks of treatment, lung CFU counts in animals treated with HRZ+AB were significantly (p<0.01) lower than those treated with HRZ (FIG. 10A). However, no significant differences were observed in lung CFU between HRZ+A, HRZ+B, and HRZ+AB.

Figure 10B:
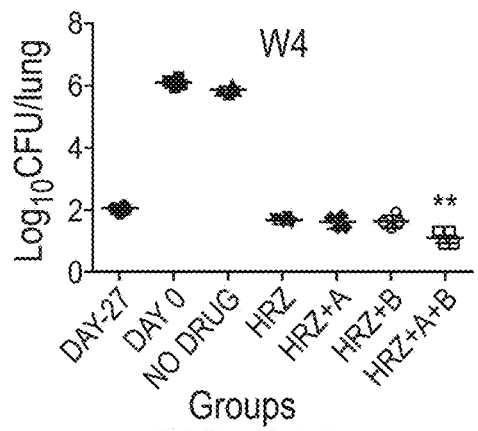

At 4 weeks post-treatment, a similar trend was seen and the hierarchy of bactericidal activities of the various regimens was HRZ+AB (1.15±0.17 $\log_{10}$ CFU)>HRZ+B (1.64±0.19 $\log_{10}$ CFU)>HRZ+A (1.65±0.2 $\log_{10}$ CFU)> HRZ (1.70±0.12 $\log_{10}$ CFU) (FIG. 10B). HRZ+AB was significantly more active than HRZ+B, HRZ+A, and HRZ alone (p<0.001).

Figure 10C:
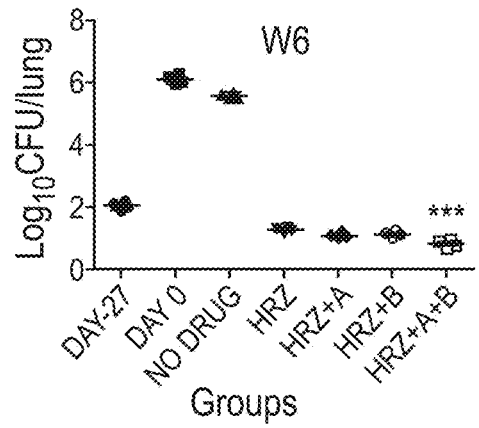

After 6 weeks of treatment, HRZ reduced mean lung CFU by 4.27 $\log_{10}$ compared to untreated controls (FIG. 8). The addition of L335-M34 (A) or L01-Z08 (B) to the standard regimen further reduced mean lung CFU by 0.14 $\log_{10}$ and 0.17 $\log_{10}$, respectively, and the combination (AB) lowered mean lung CFU by 0.45 $\log_{10}$ (p<0.0001) relative to HRZ (FIG. 10C).

Figure 11A:
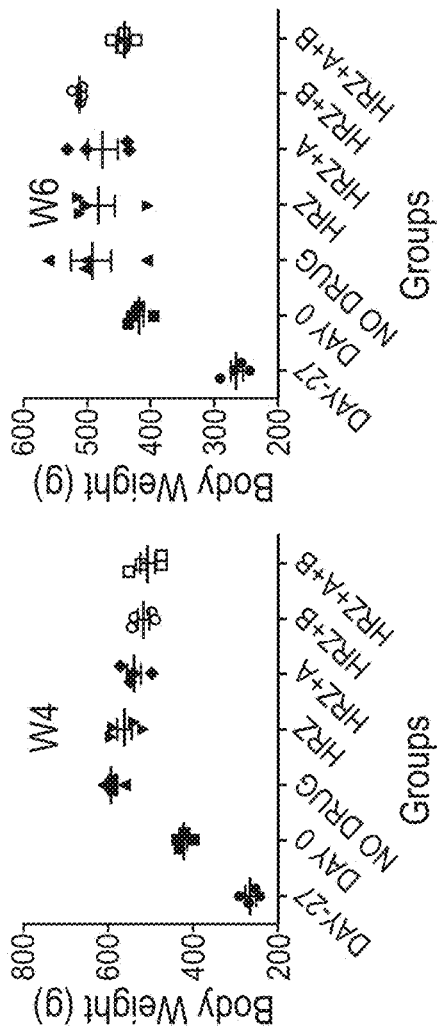
FIGS. 11A-11C depict the effects of drug treatment on body weight (FIG. 11A), lung weight (FIG. 11B), and spleen weight (FIG. 11C) in $M.$ $tuberculosis$-infected guinea pigs. No drug=untreated, HRZ: Isoniazid (H), 60/Rifampin (R), 100/Pyrazinaimde (Z), 300; A: L01-Z08, 20; B: L335M34, 50; n=4/5 per time point. Numbers after each drug refer to doses (mg/kg). n=4 per time point.
Figure 11A:
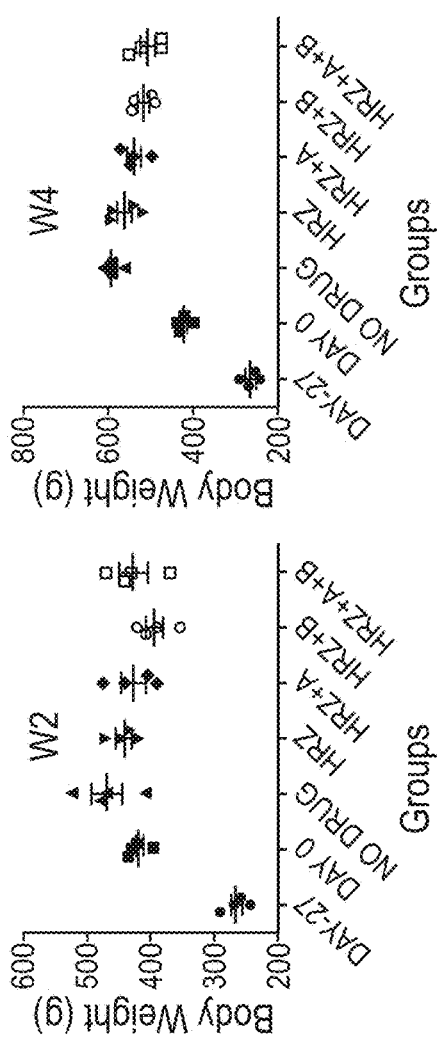
Figure 11B:
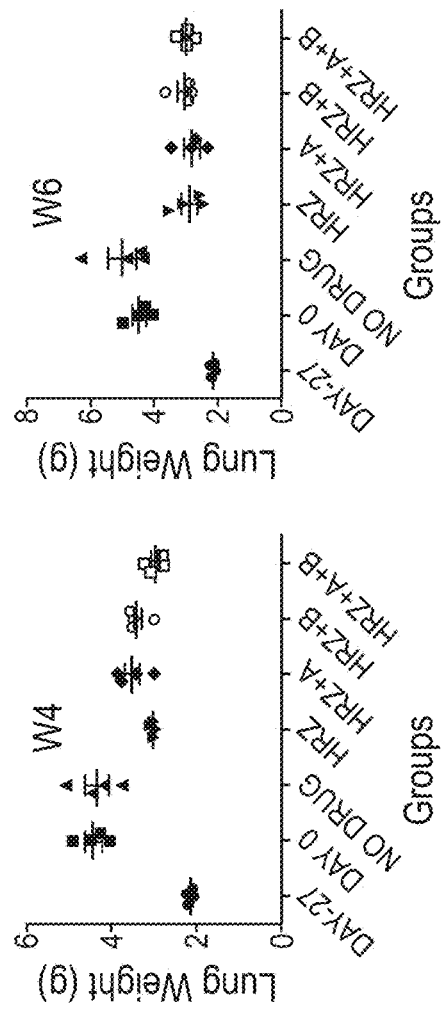
Figure 11B:
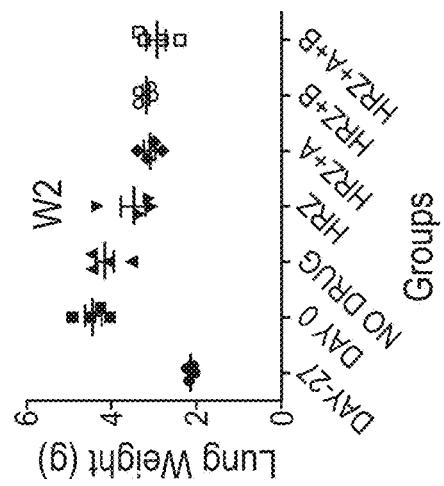
Figure 11C:
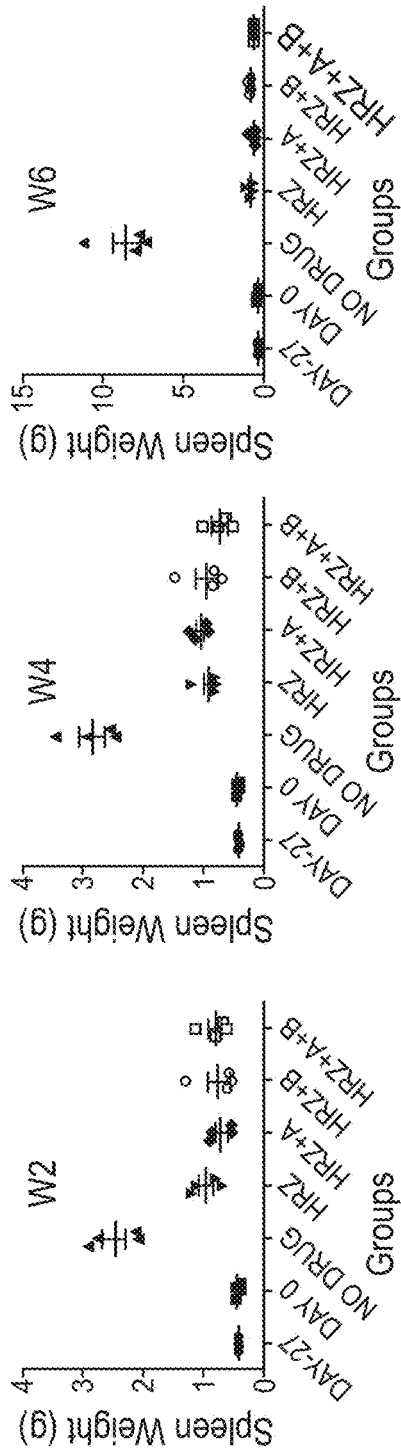

The gross pathology of guinea pig lungs (data not shown), as well as mean guinea pig lung and spleen weights (FIGS. 11A-1 IC), correlated with the efficacy of the various chemotherapy regimens. Interestingly, the mean lung surface area involved by inflammation after 6 weeks of treatment was significantly lower in the HRZ+AB (9.23%) group

TABLE 12

Pharmacokinetics of mPTPA and mPTPB Inhibitors in Guinea Pigs[a]

| Compound | Dose type | $AUC_{ALL}$ (h · ng/mL) | Clearance (mL/h/kg) | Cmax (ng/mL) $T_{max}^{b}$ (h) | $Tmax^{b}$ (h) | Half-life (h) | $V_D^{c}$ |
|---|---|---|---|---|---|---|---|
| L335M34 | Single | 54406.61 | 917.462 | 5142.47 | 2.5 | 5.197 | 6878.467 |
| L335M34 | Co-admin[d] | 52752.61 | 950.034 | 7064.956 | 2.5 | 4.16 | 5702.19 |
| L01Z08 | Single | 13166.89 | 1518.474 | 1870.43 | 1.587 | 5.512 | 12074.939 |
| L01Z08 | Co-admin[d] | 28161.76 | 701.564 | 3059.668 | 1.587 | 6.141 | 6215.132 |

[a]Data represent mean values for 2-3 animals.
[b]$T_{max}$ is the time required to achieve the maximal concentration ($C_{max}$).
[c]Volume of distribution.
[d]Both compounds L335M34 (50 mg/kg) and L01Z08 (20 mg/kg) were co-administered orally.

Figure 9:
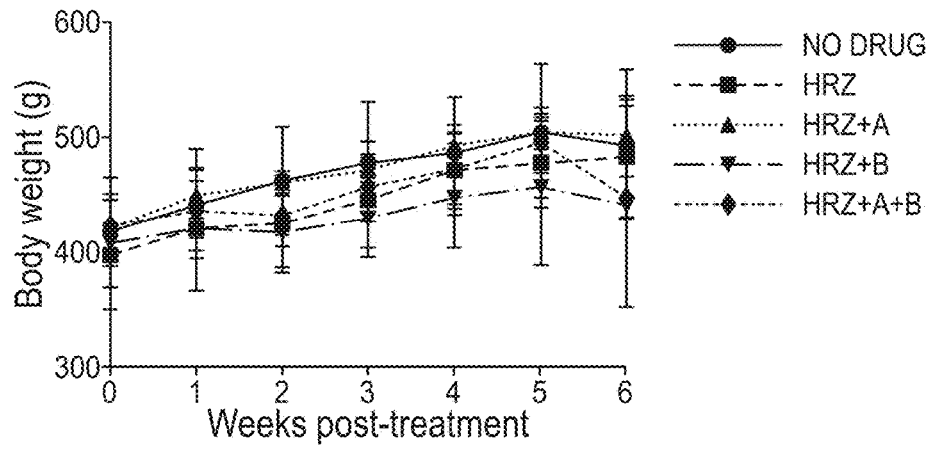
FIG. 9 depicts the average guinea pigs body weights during treatment. Numbers after each drug refer to doses (mg/kg). HRZ: Isoniazid (H), 60/Rifampin (R), 100/Pyrazinamide (Z), 300; mPTPA/A: L01-Zo8, 20; mPTPB/B: L335M34, 50; n=5 per time point; graph represents mean values±SD.

Guinea pigs receiving L01-Z08 20 mg/kg and L335-M34 50 mg/kg once daily alone or in combination for 6 weeks showed no overt signs of toxicity and displayed similar mean weight gain to those receiving HRZ (FIG. 9). All guinea pigs receiving L01-Z08 and L335-M34 survived and gained weight throughout the course of the efficacy study.

Dual Inhibition of mPTPA and mPTPB Significantly Reduces Guinea Pig Lung Bacillary Burden Relative to HRZ Alone.

Figure 12:
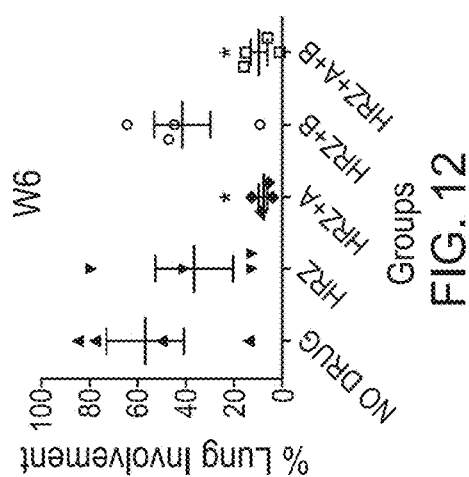
FIG. 12 depicts lung inflammation 6 weeks after initiation of treatment. Results are represented as percentage of lung surface area involved, calculated using ImageJ software. Compared to RHZ, RHZ+A/RHZ+A+B are more effective in reducing lung lesion size and number in $M.$ $tuberculosis$-infected guinea pigs at month 1.5 after treatment; *p<0.05, HRZ versus HRZ+A/HRZ+A+B.
Figure 13:
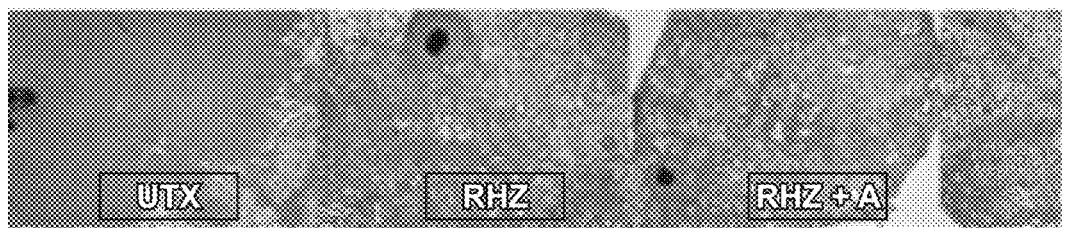
FIG. 13 depicts the combination regimes significantly reduce lung lesion size and number in $M.$ $tuberculosis$-infected guinea pigs at month 1.5 after treatment. Low-power (2× magnification) view of hematoxylin and eosin-stained sections of lungs from individual animals that best represents the mean values of 4 animals.

Since each mPTP modulates distinct Mtb clearance pathways in macrophages, it was hypothesized that dual inhibition of mPTPA and mPTPB would enhance the bactericidal activity of the standard anti-tubercular regimen in guinea pigs more than adjunctive therapy with either agent alone. Following aerosol infection of guinea pigs with Mtb H37Rv, 2.06±0.15 $\log_{10}$ bacilli were deposited in the lungs on day relative to the HRZ group (36.28%) (p=0.028). These results suggest that this effect on improved histopathology is primarily conferred by inhibition of mPTPA (HRZ+A vs HRZ+AB, p=0.68) (FIGS. 12 & 13).

The fragment-based lead optimization strategies have yielded two compounds, L01-Z08 and L335-M34, with potent activity against intracellular Mtb, as well as favorable PK and toxicity profiles. L01-Z08 and L335-M34 are inhibitors of the key secreted Mtb enzymes, mPTPB and mPTPA, respectively, and thus provide a novel mechanism of action for the treatment of TB. Both phosphatases are secreted by Mtb into the cytoplasm of the macrophage and are important for persistence of mycobacterial infection. In order to determine the potential for translation of these findings to the clinical arena, whether mPTP inhibitors could be beneficial as an adjunctive treatment when combined with the standard first-line regimen against drug-susceptible TB was evaluated in guinea pigs. The two mPTPA and mPTPB inhibitor lead compounds showed promising oral bioavailability and tolerability in this model. Although each inhibitor alone added little bactericidal activity to the standard regimen, dual inhibition of mPTPA and mPTPB significantly reduced the lung bacillary burden relative to HRZ at each time point studied.

PTKs are the molecular targets for a growing number of anticancer agents; however, there is a notable absence of drugs targeting the PTPs. Although many disease-relevant pathways are also controlled by PTPs, the latter have proven to be exceptionally challenging targets for the development of new therapeutic agents, due primarily to the poor bioavailability of existing PTP inhibitory compounds. The observed oral bioavailability and in vivo efficacy of L01-Z08 and L335-M34 are promising and further demonstrate that it is feasible to obtain PTP inhibitors that are sufficiently polar to bind the active site and yet still possess favorable pharmacological properties for therapeutic development.

Given the unique mechanisms of action of the mPTPA and mPTPB inhibitors, these compounds are expected to provide additive bactericidal activity to the standard regimen for drug-susceptible TB as well as to novel regimens for drug-resistant TB. Moreover, concomitant treatment with such inhibitors may reduce the risk for selection of strains resistant to currently available anti-TB drugs during treatment. Previous work has shown that small-molecule inhibitors of both mPTPA and mPTPB are capable of reducing intracellular mycobacteria in infected macrophages. It is interesting to note that adjunctive inhibition of mPTPA led to improved lung histopathology relative to standard treatment alone. A recent study showed that mPTPA dephosphorylates a second substrate, glycogen synthase kinase-α (GSK-α), causing its activation and the subsequent inhibition of the cell death program in infected macrophages. Based on available data, dual inhibition of mPTPA and mPTPB appears to undermine Mtb infection by (i) increasing intracellular destruction of bacteria, (ii) promoting host-beneficial apoptosis of infected macrophages, and (iii) increasing host immunologic awareness of, and responsiveness to, Mtb infection.

Previous studies have indicated that mPTPA is not essential for Mtb survival in mice, implying that the murine model fails to recapitulate the phenotypes reported in human macrophages. Although the mouse model has long been used to evaluate TB drugs, it has been increasingly recognized in the TB field that observations made in mice are not predictive of treatment outcomes in human clinical trials, nor is early "sterilization" a predictor of cure. In the current Example, the well-characterized guinea pig model of TB chemotherapy was used. Compared to mice, guinea pig TB granulomas more closely approximate their human counterparts with respect to cellular composition, granuloma architecture, and the presence of caseation necrosis. In addition, tissue hypoxia is present in guinea pig TB granulomas, but absent in mouse TB lung lesions. These histological and micro-environmental factors, which may be biological determinants of Mtb persistence, as well as concordance of treatment outcomes with those of recent human studies, make the guinea pig model an attractive one for testing the activity of novel anti-tubercular agents. However, the anti-tubercular activity of these agents could be further characterized in other clinically relevant models, such as the rabbit and non-human primate.

The data support the further development of the Mtb PTP inhibitor class of drugs. PTP inhibitors lack direct antimicrobial activity, but promote intracellular Mtb killing in vitro. These findings suggest a modest increase in killing by the standard regimen with dual mPTPA/B inhibition, as well as a favorable PK interaction between the agents. Significantly, the data suggest that PTP inhibitors may improve clinical outcomes by ameliorating lung pathology.

Example 4

Selective Inhibition of LMWPTP.

SPAA based compounds from the libraries were studied as inhibitors against a panel of PTPs, including LMWPTP and Laforin. In the library, 8 compounds exhibited a similar level of activity against human LMPTP and Laforin ($IC_{50}$ about 5-10 μM), generally with at least about 10-fold selectivity for LMPTP and Laforin over other PTPs (Tables 5 and 13).

TABLE 13

$IC_{50}$ values of LMWPTP inhibitors against a panel of PTPs

| $IC_{50}$ (μM) | LMWPTP | SHP2 | PTP1B | SHP1 | TcPTP | VHX | STEP | HePTP | TbPTP | FAP-1 | VHR | LYP | Ssu72 | PEST | Laforin |
|---|---|---|---|---|---|---|---|---|---|---|---|---|---|---|---|
| L319M34 | 5.3 | >100 | >200 | 55.5 | >100 | 92.0 | >200 | >100 | >100 | >100 | >200 | >200 | >100 | 72.3 | 4.05 |
| L319M50 | 12.1 | >200 | >200 | 53.2 | >100 | >100 | >200 | >100 | >100 | 73.0 | >200 | >200 | 66.6 | 69.9 | 2.06 |
| L319M54 | 5.6 | >200 | >200 | >200 | >200 | >200 | >200 | >200 | >200 | >100 | >200 | >200 | >200 | >200 | 4.25 |
| L319M63 | 7.7 | >100 | >100 | >200 | >100 | >200 | >100 | >100 | >100 | >100 | >100 | >100 | >100 | >100 | 2.65 |
| L319M68 | 8.1 | >200 | >200 | >200 | >200 | >200 | >200 | >200 | >200 | >200 | >200 | >200 | >200 | >200 | 7.47 |
| L319M88 | 7.3 | >100 | >100 | >200 | >100 | >200 | >100 | >100 | >100 | >100 | >100 | >100 | >100 | >100 | 8.51 |
| L319N15 | 7.1 | >100 | >200 | 59.6 | >200 | >100 | >100 | 50.0 | >200 | 34.0 | >200 | >200 | 69.0 | 43.5 | 2.1 |
| L319N22 | 6.4 | >200 | >200 | >200 | >200 | >200 | >100 | 94.0 | >200 | 76.0 | >200 | >200 | 83.0 | 66.9 | 27.0 |

To develop specific inhibitors of either LMPTP or Laforin, L319N15 (with a benzo[d]thiazol-2-yl moiety attached to the amide group, Table 5) was selected as a lead compound in a medicinal chemistry effort. As shown in Table 6, 22 analogues of L319N15 were synthesized, including L319N3 (with a thiazole-2-yl moiety), L319N4 (with a 4-phenylthiazole-2-yl moiety), L319N15-01 to L319N15-13 (with various substituents on the benzo[d]thiazol-2-yl moiety of L319N15), L319N15-14 to L319N15-18 (with various substituents on the a benzene ring), L335N15, L335N15-07, and L338N15 (with the deletion of a benzene ring). The $IC_{50}$ of these compounds were measured against LMPTP and Laforin (Table 14).

TABLE 14

$IC_{50}$ values of L319N15 analogues against LMWPTP and representative PTPs

| $IC_{50}$ (μM) | LMWPTP | SHP2 | PTP1B | LYP | CD45 | Laforin |
|---|---|---|---|---|---|---|
| L319N13 | 100 | >100 | >100 | >100 | >100 | 8 |
| L319N14 | 20 | 31 | 160 | 15 | 70 | 6 |
| L319N15 | 8.6 | 160 | >200 | 190 | 180 | 2.1 |

TABLE 14-continued

IC$_{50}$ values of L319N15 analogues against LMWPTP and representative PTPs

| IC$_{50}$ (μM) | LMWPTP | SHP2 | PTP1B | LYP | CD45 | Laforin |
|---|---|---|---|---|---|---|
| L319N15-01 | 4.6 | 41 | 70 | 22 | 100 | 2.2 |
| L319N15-02 | 9.6 | 129 | >200 | 110 | >200 | 4 |
| L319N15-03 | 7.6 | >200 | >200 | >200 | >200 | 1.2 |
| L319N15-04 | 4.8 | 112 | >200 | 90 | >200 | 1.1 |
| L319N15-05 | 4.2 | 173 | >200 | 150 | >200 | 1.7 |
| L319N15-06 | 5.6 | 30 | 80 | 23 | 130 | 2.3 |
| L319N15-07 | 2.1 | >200 | >200 | >100 | >200 | >200 |
| L319N15-08 | 8.2 | >200 | >200 | >200 | >200 | 2.0 |
| L319N15-09 | 5.3 | 47 | 160 | 20 | 80 | 3.2 |
| L319N15-10 | 5.8 | >200 | >200 | >200 | >200 | 2.1 |
| L319N15-11 | 3.03 | 55 | 200 | 28 | 70 | 1.7 |
| L319N15-12 | 14 | 190 | >200 | 166 | 160 | 3.3 |
| L319N15-13 | 70 | 83 | >200 | 31 | 90 | >200 |
| L319N15-14 | >200 | >200 | >200 | >200 | >200 | 19 |
| L319N15-15 | 21 | 2.6 | 31 | 5 | 30 | 4.3 |
| L319N15-16 | >200 | 135 | >200 | 180 | >200 | 66 |
| L319N15-17 | >100 | >100 | >100 | >100 | >100 | 14 |
| L319N15-18 | >100 | >100 | >100 | >100 | >100 | 32 |
| L335N15 | 2.1 | >100 | >100 | >100 | >100 | >100 |
| L335N15-07 | 0.3 | >100 | >100 | >100 | >100 | >100 |
| L338N15 | 30 | NA | NA | NA | NA | NA |

As shown in Table 14, most of the L319N15 analogues preferably inhibit Laforin (IC$_{50}$ about 1 to 10 μM). Remarkably, L319N15-07, L319N15-13, L335N15, and L335N15-07 showed specificity towards LMPTP, but not Laforin. For example, under the same assay conditions, L319N15-07 and L335N15-07 inhibited LMPTP at IC$_{50}$ values of 2.1 μM and 0.3 μM, respectively, while they showed no detectable inhibition against Laforin at 100 μM. Similarly, L319N15-13 showed an IC$_{50}$ value of 70 μM against LMPTP, did not inhibit Laforin at 200 μM.

Remarkably, these three compounds all have a polar substituent at position 3 on the benzene ring of the benzo[d]thiazol-2-yl moiety: a nitro group for L319N15-07 and L335N15-07, and a carboxy group for L319N15-13 (Table 6). Without being bound by any theory, it is hypothesized that the negative or partially negative charge (such as that in the nitro and the carboxy groups) in the amide substituent (such as the benzo[d]thiazole moiety of L319N15) causes these compounds to preferably inhibit LMWPTP over Laforin.

Surprisingly, L319N15-07 and L335N15-07 exhibited no detectable inhibition against any PTP in Table 8 (other than mPTPA and mPTPB) at up to 100 μM (see Table 10 for results of SHP2, PTP1B, LYP, and CD45). These data indicate that L319N15 analogs inhibit LMPTP more specifically over the other 30 PTPs tested. In particular, for L319N15-07 and L335N15-07, the inhibition is more than 100-fold selective for LMWPTP over other PTPs (Table 14). Thus, the SPAA based L319N15 analogs can be used to develop anti-cancer and anti-diabetes drugs targeting at LMWPTP.

Example 5

Potent and Specific Inhibition of mPTPA.

Several potent inhibitors against mPTPA have been identified in the libraries described herein (Table 4). Results of IC$_{50}$ measurements against mPTPA and other PTPs are shown in Table 15.

TABLE 15

IC$_{50}$ values of mPTPA inhibitors against a panel of PTPs

| IC$_{50}$ (μM) | L319M34 | L319M54 | L319M68 | L319M88 | L319N15 | L319N22 | L335N15 |
|---|---|---|---|---|---|---|---|
| mPTPA | 0.2 | 0.27 | 0.25 | 0.143 | 0.194 | 0.972 | 0.263 |
| mPTPB | 0.055 | 0.078 | 5.0 | 0.282 | 0.116 | 0.203 | 9.5 |
| LMWPTP | 4.5 | 5.0 | 20 | 6.1 | 7.1 | 6.39 | 2.1 |
| Laforin | 1.05 | 4.25 | 7.5 | 8.5 | 2.1 | 50 | >100 |
| YopH | >200 | >200 | >200 | >200 | >200 | >200 | >100 |
| TbPTP1 | >200 | >200 | >200 | >200 | >200 | >200 | >100 |
| PTP1B | >200 | >200 | >200 | >200 | >200 | >200 | >100 |
| TcPTP | >200 | >200 | >200 | >200 | >200 | >200 | >100 |
| LYP | >200 | >200 | >200 | >200 | >200 | >200 | >100 |
| PEST | 42.3 | >200 | >200 | >200 | 43.5 | 67 | >100 |
| SHP1 | >200 | >200 | >200 | >200 | >200 | >200 | >100 |
| SHP2 | >200 | >200 | >200 | >200 | >200 | >200 | >100 |
| HePTP | >200 | >200 | >200 | >200 | 50 | 94 | >100 |
| Meg2 | >200 | >200 | >200 | >200 | >200 | >200 | >100 |
| PTPH1 | >200 | >200 | >200 | >200 | >200 | >200 | >100 |
| FAP1 | >200 | 180 | >200 | >200 | 34 | 76 | >100 |
| CD45 | >200 | >200 | >200 | >200 | >200 | >200 | >100 |
| LAR | >200 | >200 | >200 | >200 | >200 | >200 | >100 |
| PTPα | >200 | >200 | >200 | >200 | >200 | >200 | >100 |
| PTPβ | >200 | >200 | >200 | >200 | >200 | >200 | >100 |
| PTPγ | >200 | >200 | >200 | >200 | >200 | >200 | >100 |
| PTPσ | >200 | >200 | >200 | >200 | >200 | >200 | >100 |
| PTPε | >200 | >200 | >200 | >200 | >200 | >200 | >100 |
| PTPμ | >200 | >200 | >200 | >200 | >200 | >200 | >100 |
| STEP | >200 | >200 | >200 | >200 | >200 | 140 | >100 |
| MKP3 | >200 | >200 | >200 | >200 | >200 | >200 | >100 |
| VHR | >200 | >200 | >200 | >200 | >200 | >200 | >100 |
| VHX | 92 | >200 | >200 | >200 | >200 | >200 | >100 |
| VHX | >200 | >200 | >200 | >200 | >200 | >200 | >100 |
| CDC14A | >200 | >200 | >200 | >200 | >200 | >200 | >100 |
| PP5 | >200 | >200 | >200 | >200 | >200 | >200 | >100 |
| Ssu72 | >200 | >200 | >200 | >200 | 69 | 83 | >100 |

TABLE 15-continued

| IC$_{50}$ values of mPTPA inhibitors against a panel of PTPs | | | | | |
|---|---|---|---|---|---|
| IC$_{50}$ (µM) | L335N15-07 | L335M34 | L335M54 | L335M68 | L335M88 |
| mPTPA | NA | 0.16 | 0.65 | 2.2 | 3.0 |
| mPTPB | NA | 3.1 | NA | NA | 55 |
| LMWPTP | 0.3 | 4.2 | 1.86 | 63 | 12 |
| Laforin | >100 | >100 | >100 | NA | >100 |
| YopH | >100 | >100 | >100 | NA | >100 |
| TbPTP1 | >100 | >100 | >100 | NA | >100 |
| PTP1B | >100 | >100 | >100 | NA | >100 |
| TcPTP | >100 | >100 | >100 | NA | >100 |
| LYP | >100 | >100 | >100 | NA | >100 |
| PEST | >100 | >100 | >100 | NA | >100 |
| SHP1 | >100 | >100 | >100 | NA | >100 |
| SHP2 | >100 | >100 | >100 | NA | >100 |
| HePTP | >100 | >100 | >100 | NA | >100 |
| Meg2 | >100 | >100 | >100 | NA | >100 |
| PTPH1 | >100 | >100 | >100 | NA | >100 |
| FAP1 | >100 | >100 | >100 | NA | >100 |
| CD45 | >100 | >100 | >100 | NA | >100 |
| LAR | >100 | >100 | >100 | NA | >100 |
| PTPα | >100 | >100 | >100 | NA | >100 |
| PTPβ | >100 | >100 | >100 | NA | >100 |
| PTPγ | >100 | >100 | >100 | NA | >100 |
| PTPσ | >100 | >100 | >100 | NA | >100 |
| PTPε | >100 | >100 | >100 | NA | >100 |
| PTPµ | >100 | >100 | >100 | NA | >100 |
| STEP | >100 | >100 | >100 | NA | >100 |
| MKP3 | >100 | >100 | >100 | NA | >100 |
| VHR | >100 | >100 | >100 | NA | >100 |
| VHX | >100 | >100 | >100 | NA | >100 |
| VHX | >100 | >100 | >100 | NA | >100 |
| CDC14A | >100 | >100 | >100 | NA | >100 |
| PP5 | >100 | >100 | >100 | NA | >100 |
| Ssu72 | >100 | >100 | >100 | NA | >100 |

Particularly, L319M68 was shown to inhibit mPTPA with IC$_{50}$ at 0.25 µM, a 20-fold selectivity over mPTPB, a 80-fold selectivity over human LMWPTP, a 30-fold selectivity over Laforin, and a >800-fold selectivity over all other human PTP tested. Kinetic studies show that L319M68 is a competitive inhibitor against mPTPA with Ki at 0.13 µM. In addition, L335M34 showed an IC50 at 0.16 µM, a 20-fold selectivity over mPTPB, a 30-fold selectivity over human LMWPTP, and a >1000-fold selectivity over all other human PTP including laforin. Hence, these compounds are potent and selective inhibitors of mPTPA, allowing for development of anti-TB agents targeting at mPTPA.

Example 6

SPAA Based mPTPA and mPTPB Dual Inhibitors.

Compounds inhibiting mPTPA and mPTPB are also desirable in developing anti-TB agents. The approach is particularly attractive, given that mPTPA and mPTPB are produced and secreted by the same Mtb strain.

Compounds L319M34, L319M54, and L319N15 described herein (Table 1) have been identified to inhibit both mPTPA and mPTPB (IC$_{50}$ approximately 0.05-0.2 µM), but not other PTPs (see Table 15). For example, L319M34 demonstrated an IC$_{50}$ of 0.2 and 0.055 µM to mPTPA and mPTPB, respectively, with a selectivity of at least 20-fold over any other mammalian PTPs, including its close analogue, human LMWPTP. These results indicate that SPAA based compounds can be used as dual inhibitors for both mPTPA and mPTPB, allowing for the development of anti-TB agents targeting at both PTPs.

Example 7

Potent and Specific Inhibition of Laforin.

From the SPAA based library of compounds described herein, several potent and specific Laforin inhibitors have been identified (Table 2). The IC$_{50}$ concentrations of these compounds range from low µM to nM scale (Table 16).

TABLE 16

| IC$_{50}$ values of Laforin inhibitors against a panel of PTPs | | | | | | | | | | | | | | | |
|---|---|---|---|---|---|---|---|---|---|---|---|---|---|---|---|
| IC$_{50}$ (µM) | Laforin | LMWPTP | SHP2 | PTPIB | SHP1 | TcPTP | VHX | STEP | HePTP | TbPTP-1 | FAP-1 | VHR | LYP | Ssu72 | PEST |
| L319M50 | 2.06 | 12.1 | >200 | >200 | 53.2 | >100 | >100 | >200 | >100 | >100 | 73.0 | >200 | >200 | 66.6 | 69.9 |
| L319M52 | 5.08 | 72.3 | >200 | >200 | 62.3 | >100 | >100 | >200 | >100 | >100 | 88.0 | >200 | >200 | 97.6 | 77.4 |
| L319M63 | 2.65 | 7.7 | >100 | >100 | >200 | >100 | >200 | >100 | >100 | >100 | >100 | >100 | >100 | >100 | >100 |
| L319M373-2 | 1.3 | 10.2 | NA | NA | NA | NA | NA | NA | NA | NA | NA | NA | NA | NA | >200 |
| L319M79 | 2.2 | 23.6 | NA | NA | NA | NA | NA | NA | NA | NA | NA | NA | NA | NA | 26.5 |
| L319N08 | 4.72 | 28.9 | >100 | >200 | 64.6 | >200 | >200 | >100 | 78.0 | >100 | 71.0 | >200 | >200 | 72.9 | 59.7 |
| L319N72 | 4.8 | 98.1 | NA | NA | NA | NA | NA | NA | NA | NA | NA | NA | NA | NA | >200 |
| L319-2-A60 | 9 | >200 | >200 | >200 | >200 | >200 | >200 | >200 | >200 | >200 | >200 | >200 | >200 | >200 | >200 |

TABLE 16-continued

IC$_{50}$ values of Laforin inhibitors against a panel of PTPs

| IC$_{50}$ (μM) | Laforin | LMWPTP | SHP2 | PTPIB | SHP1 | TcPTP | VHX | STEP | HePTP | TbPTP-1 | FAP-1 | VHR | LYP | Ssu72 | PEST |
|---|---|---|---|---|---|---|---|---|---|---|---|---|---|---|---|
| L319-05-A64 | 0.8 | 29 | 69 | 183 | 200 | 96 | 100 | >100 | 150 | 93 | 70 | 50 | 62 | 170 | 160 |
| L319-21-M06 | 0.14 | >50 | >50 | >50 | >50 | >50 | >50 | >50 | >50 | >50 | >50 | >50 | >50 | >50 | >50 |
| L319-21-M50 | 1.11 | >50 | 51 | >50 | >50 | >50 | >50 | >50 | >50 | >50 | 39 | >50 | >50 | >50 | >50 |
| L319-21-M51 | >0.1 | NA | NA | NA | NA | NA | NA | NA | NA | NA | NA | NA | NA | NA | NA |
| L319-21-M52 | 0.15 | >50 | >50 | >50 | >50 | >50 | >50 | >50 | >50 | >50 | >50 | >50 | >50 | >50 | >50 |

As shown in Table 16, L319M73-2 inhibited Laforin at an IC$_{50}$ value of 1.3 μM, with an 8-fold specificity for Laforin over LMPTP and a 100-fold specificity over 30 other human PTPs. In addition, L319-02-A60, L319-05-A64 (IC$_{50}$=9, 0.8 μM) are highly specific with >20-fold selectivity against any other PTPs, including LMWPTP.

Remarkably, L319-21 series compounds (L319-21-M06, -M50, -M51, and -M52) inhibited Laforin at IC$_{50}$ around 0.1 μM, with an over 500-fold selectivity over other PTPs. Thus, SPAA based compounds described herein are potent and specific PTP inhibitors, which can be used to study the molecular mechanisms of Lafora disease.

Example 8

Inhibition of SHP2.

Several compounds in the SPAA based library described herein (for example, L319-20-M24, L319-20-M74, L319-20-M78, L319-20-N08, L319-20-N25, L319-22-M34, L319-22-M50, L319-22-M51, L319-23-M74, L319-24-M74, L319-24-M77, and L319-04-B34) have been identified as effective inhibitors of SHP2 (Tables 3 and 17). The IC$_{50}$ of these compounds for SHP2 inhibition was shown to be approximately in the 1-10 μM range.

TABLE 17

IC$_{50}$ values of SHP2 inhibitors.

| Compound ID | SHP2 IC$_{50}$, μM |
|---|---|
| L319-20-M24 | 1.5 |
| L319-20-M74 | 0.9 |
| L319-20-M78 | 0.7 |
| L319-20-N08 | 1.4 |
| L319-20-N25 | 2.3 |
| L319-22-M34 | 5.7 |
| L319-22-M50 | 7.5 |
| L319-22-M51 | 10 |
| L319-23-M74 | 3.5 |
| L319-24-M74 | 1.34 |
| L319-24-M77 | 1.1 |
| L319-04-B34 | 7.9 |

Example 9

Experimental Section

Protein Expression and Purification.

The SHP2 catalytic domain (residues 224-528) used for kinetic studies was cloned into the pET-21a+ vector using NdeI and XhoI (NEB), and mutants E508A and R362A were generated using QuikChange mutagenesis Kit (Stratagene). These proteins were expressed in E. coli BL21(DE3) and purified with Ni-NTA resin (Qiagen). The SHP2 catalytic domain (residues 262-528) used for crystallization was expressed in E. coli BL21(DE3) and purified by Ni-NTA agarose (Qiagen) followed by sequential chromatography of HiPrep 26 desalting column (GE Healthcare), and cation exchange column packed with SP sepharose (GE Healthcare). Protein purity was determined to be greater than 95% by SDS-PAGE and Coomassie blue staining.

Enzyme Kinetics and Inhibition Studies.

The SHP2 phosphatase activity was assayed in 96-well plates using pNPP as a substrate at 25° C. in 50 mM 3,3-dimethylglutarate (DMG) buffer (pH=7.0), containing 1 mM EDTA with an ionic strength of 0.15 M adjusted by NaCl. The FDA-approved drug collection or the SPAA based libraries were screened in a 96-well format at two different compound concentrations (10 and 20 μM for FDA drugs and 10 and 1 μM for the SPAA libraries). The reaction was initiated by the addition of 50 μl of SHP2 to 150 μl of reaction mixture containing pNPP and the compound, the resulting 200 μl mixture has SHP2 at a final concentration of 20 nM, and pNPP at a final concentration of 3 mM (the K$_m$ for pNPP). The reaction was allowed to proceed for 10 minutes, and then quenched by addition of 50 μl of 5N NaOH. The amount of product, p-nitrophenol, was determined from the absorbance at 405 nm detected by a Spectra MAX340 microplate spectrophotometer (Molecular Devices) using a molar extinction coefficient of 18,000 M$^{-1}$cm$^{-1}$. The nonenzymatic hydrolysis of pNPP was corrected by measuring the control without enzyme. The Michaelis-Menten kinetic parameters k$_{cat}$ and K$_m$ were determined from a direct fit of the velocity versus substrate concentration data to Michaelis-Menten equation using SigmaPlot program. Inhibitor concentrations used for IC$_{50}$ measurements cover the range from 0.2 to 5× of the IC$_{50}$ value. IC$_{50}$ values for cefsulodin and compounds 2-7 were calculated by fitting the absorbance at 405 nm versus inhibitor concentration to the following equation:

$$A_I/A_0 = IC_{50}/(IC_{50}+[I])$$

where A$_I$ is the absorbance at 405 nm of the sample in the presence of inhibitor, A$_0$ is the absorbance at 405 nm in the absence of inhibitor, and [I] is the concentration of the inhibitor.

For inhibitor selectivity profiling studies, the PTPs, including cytosolic PTPs, SHP1, PTP1B, LYP, HePTP, and PTP-Meg2, the receptor-like PTPs, CD45, PTPβ, PTPε, PTPγ, PTPμ and LAR, the dual specificity phosphatases VHR and CDC14A, the low molecular weight (LMW) PTP, and the Ser/Thr protein phosphatase PP5, were expressed and purified from E. coli. The inhibition assays for these PTPs were performed under the same conditions as SHP2 except using a different pNPP concentration corresponding to the $K_m$ of the PTP studied.

Crystallography Studies.

The SHP2.cefsulodin co-crystals were grown at 20° C. in the hanging drops containing 1.5 µL protein solution (8 mg/ml SHP2 with 1 mM cefsulodin in 20 mM MES, pH 5.8, 300 mM NaCl, 2 mM DTT and 1 mM EDTA) and 1.5 µL reservoir solution (20% PEG3350, 33 mM citric acid, 67 mM BIS-TRIS propane, pH=7.4). The crystals were transferred into 2 µL of cryo-protectant buffer (150 mM NaCl, 1 mM cefsulodin, 30% PEG3350, 33 mM citric acid, 67 mM BIS-TRIS propane, pH=7.4), allowed to soak for 5 minutes and then flash-frozen by liquid nitrogen. Data were collected at the 19-BM beam line at the Advanced Photon Source (APS) and were processed with HKL3000. The data were collected to 1.6 Å resolution in the $P_{21}$ space group. The phase was determined by molecular replacement with Molrep (Vagin, A.; Teplyakov, A. J. Appl. Crystallogr. 1997, 30, 1022) using the coordinates of reported SHP2 structure (PDBID: 3B7O) as the search model. The SHP2.cefsulodin complex structure was refined using phenix.refine in the PHENIX software suite. The electron density maps were inspected and the model was tuned in Coot. The data collection and structure refinements statistics are summarized in Table 19.

Molecular Modeling of the Interaction of SHP2 with Cefsulodin.

AutoDock_Vina1.1.2 program (Trott, O.; Olson, A. J. J. Comput. Chem. 2010, 31, 455) was used to build the most likely binding modes for cefsulodin and SHP2. The 3D-structure of cefsulodin was modeled and energy-minimized in Chem3D program, and the coordinates of SHP2 catalytic domain (PDBID: 3B7O) were retrieved from the Protein Data Bank. Both ligand and the receptor structures were pre-processed in AutoDockTools1.5.4, such as merging non-polar hydrogens, adding Gasteiger charges, setting rotatable bonds for the ligand, adding solvation parameter for the receptor, and so on. A docking space of 21.0×21.0× 22.5 Å was visually set around the catalytic active site, the parameter of exhaustiveness, num_modes and energy_range was set to 20, 200 and 4 respectively, and the default values were used for the other parameters.

Characterization of Cefsulodin-Mediated SHP2 Inhibition by Q-TOF ESI-MS, LC-MS, and HPLC.

Agilent 6520 Accurate-Mass was used for the Q-TOF ESI-MS studies. Water and acetonitrile (both containing 0.1% formic acid) were used as eluent (80% water, flow 50 µL/min, run time 5 minutes). ESI positive mode was used with mass range from 300 to 1700, the gas temperature was 325° C., and vaporizer temperature was: 819° C. The sample was adjusted to have a concentration at 0.1 mg/mL, the injection volume of each sample was 1 µL. Mass hunter software was used for protein deconvolution data analysis to calculate the molecular weight of the protein.

Agilent Technologies 6130 quadrupole LC-MS instrument was used for the LC-MS studies. A C18 reserved phase column (phenomenex, 50×4.6 mm) was used as stationary phase, water and methanol (both containing 0.1% formic acid) were used as mobile phase (gradient: 0-100% methanol, flow 0.8 mL/min, run time 15 minutes), and UV absorbance at the fixed wavelength of 254 nm and positive and negative ESI-MS data were recorded. The sample was adjusted to have a concentration at 0.1 mg/mL, and the injection volume of each sample was 0.2 µL. The retention time and corresponding ESI-MS data were used as identity of molecules.

Waters 2545 preparative HPLC purification system was used for compound purification. A C18 reserved phase column (Sunfire, 50×150 mm) was used as stationary phase, water and methanol (both containing 0.1% trifluoroacetic acid) were used as mobile phase (gradient: 0-100% methanol, flow 50 mL/min, run time 60 minutes), and UV absorbance at the fixed wavelength of 254 nm was used for fraction collection. The compound identity was validated by LC-MS studies following HPLC purification.

Cell Proliferation and Immunoblot Analysis.

Human non-small cell lung carcinoma cell line H1975 was cultured at 37° C. and 5% $CO_2$ in RPMI-1640 (Corning) supplemented with 10% fetal bovine serum (HyClone). Human breast cancer cell line MDA-MB-231 was cultured in DMEM supplemented with 10% fetal bovine serum. For cell proliferation assay, $2\sim3\times10^3$ cells were seeded in each well of 96-well plates. After treating cells with compounds for 2 days, cells were incubated with 50 µg/ml MTT (3-(4,5-Dimethylthiazol-2-yl)-2,5-diphenyltetrazolium bromide) for ~3-4 hours. Then, the culture medium was removed, DMSO was added to dissolve the formazan crystals. Wells containing only media were used for background correction. The optical density was measured spectrophotometrically at 540 nm. For signaling analysis, cells were serum-starved overnight followed by treatment with vehicle or compounds for 3 hours, and then either left un-stimulated or stimulated with 5 µg/ml EGF or 10 nM PMA (Sigma) for indicated time. Cells were lysed and the lysates were electrophoresed on a 10% polyacrylamide gel, and then transferred to a nitrocellulose membrane, and probed with anti-phospho-ERK1/2 and anti-ERK1/2 (Cell Signaling) antibodies followed by incubation with horseradish peroxidase-conjugated secondary antibodies. The blots were developed by the enhanced chemiluminescence technique using the SuperSignal West Pico Chemiluminescent substrate (Pierce).

SHP2 Inhibitor 2 Effects on Cell Growth in Matrigel.

Approximately 300,000 SKBR3 cells were seeded into 150 µL of growth factor reduced Matrigel (BD) that was then covered with 2 mLs of media containing either 20 µL vehicle (DMSO) or the indicated concentrations of compound 2. Cells were then imaged at 24-hour intervals using a NIKON SMZ1500 stereomicroscope. After 5 days the cells were recovered from the Matrigel by the following method. Media was aspirated and cells were washed with 500 µL of cold PBS. 150 µL of RIPA lysis buffer supplemented with ProteCEASE-50. EDTA Free protease inhibitors (GBiosciences) was added to the Matrigel. Cells were scraped into a slurry and instantly frozen using dry ice for 5 minutes. After thawing tubes were spun down at 4° C. for 10 minutes at 14K rpm. Proteins were then resolved by SDS-PAGE and the relative levels of total and phospho-ERK1/2 were detected by immunoblot analysis.

Chemical Synthesis: Materials and General Procedures.

Cefsulodin and other antibiotics were used as purchased from Sigma-Aldrich, and all other reagents were from Fisher Scientific. $^1$H and $^{13}$C NMR spectra were obtained on a Bruker Avance II 500 MHz or a Bruker Fourier 300 MHz NMR spectrometer with TMS or residual solvent as standard. Accurate mass data was obtained using an Agilent 6520 Accurate-Mass instrument.

Synthesis of Lib-1, Lib-2, Lib-3, and Lib-4.

To α-sulfophenyl acetyl chloride (0.234 g, 1 mmol) and DIEA (0.522 mL, 3 mmol) in DMF (2 mL) was added N-Boc-p-phenylenediamine (0.208 g, 1.0 mmol). The reaction mixture was stirred at room temperature for 0.5 hours and then was concentrated by rotary evaporator. The resulting mixture was treated with 100% TFA at room temperature for 3 hours to remove the Boc protecting group. The mixture was concentrated again by rotary evaporator, and treated with methyl oxalyl chloride (0.135 g, 1.1 mmol) and DIEA (0.522 mL, 3 mmol) in DMF (2 mL) for 0.5 hours at room temperature. Finally, the mixture was hydrolyzed by 10% LiOH to furnish product 2-oxo-2-((4-(2-phenyl-2-sulfoacetamido)phenyl)amino)acetic acid (Lib-1). Subsequently, it was subjected to HPLC purification, and product Lib-1 was obtained as colorless oil with 56% overall yield and >95% purity. 2-oxo-2-((3-(2-phenyl-2-sulfoacetamido)phenyl)amino)acetic acid (Lib-2) and 2-oxo-2-((4-(2-phenyl-2-sulfoacetamido)benzyl)amino)acetic acid (Lib-3) were obtained in similar procedures by using N-Boc-m-phenylenediamine and 4-[(N-Boc)aminomethyl]aniline, respectively.

2-oxo-2-((4-(2-phenyl-2-sulfoacetamido)phenyl)amino)acetic acid (Lib-1): $^1$H NMR (500 MHz, DMSO-d6) δ 10.65 (s, 1H), 10.31 (s, 1H), 7.69 (d, J=9.1 Hz, 2H), 7.57-7.54 (m, 4H), 7.30-7.24 (m, 3H), 4.75 (s, 1H). $^{13}$C NMR (125 MHz, DMSO-d6) δ 165.8, 162.2, 156.6, 135.8, 135.3, 133.0, 129.9, 127.4, 127.0, 71.8. ESI-MS Cacld. for C16H13N2O7S (M–H$^+$): m/z 377.0449; found 377.0450.

2-oxo-2-((3-(2-phenyl-2-sulfoacetamido)phenyl)amino)acetic acid (Lib-2): $^1$H NMR (500 MHz, DMSO-d6) δ 10.68 (s, 1H), 10.36 (s, 1H), 8.03 (t, J=1.6 Hz, 1H), 7.57-7.55 (m, 2H), 7.44-7.38 (m, 2H), 7.30-7.24 (m, 4H), 4.78 (s, 1H). $^{13}$C NMR (125 MHz, DMSO-d6) δ 166.0, 162.2, 157.0, 139.4, 138.0, 135.2, 129.9, 129.0, 127.5, 127.0, 115.4, 115.3, 111.1, 71.8. ESI-MS Cacld. for C16H13N2O7S (M–H$^+$): m/z 377.0449; found 377.0445.

2-oxo-2-((4-(2-phenyl-2-sulfoacetamido)benzyl)amino)acetic acid (Lib-3): $^1$H NMR (500 MHz, DMSO-d6) δ 10.30 (s, 1H), 9.31 (t, J=6.2 Hz, 1H), 7.56-7.51 (m, 4H), 7.29-7.19 (m, 5H), 4.74 (s, 1H), 4.26 (d, J=6.3 Hz, 2H). $^{13}$C NMR (125 MHz, DMSO-d6) δ 165.9, 162.2, 158.4, 138.0, 135.3, 133.3, 129.9, 127.9, 127.5, 127.0, 118.9, 71.8, 30.7. ESI-MS Cacld. for C17H15N2O7S (M–H$^+$): m/z 391.0605; found 391.0609.

2-oxo-2-((4-((2-phenyl-2-sulfoacetamido)methyl)phenyl)amino)acetic acid (Lib-4) was synthesized using a slightly different procedure. 4-[(N-Boc)aminomethyl]aniline was treated with methyl oxalyl chloride (0.135 g, 1.1 mmol) and DIEA (0.522 mL, 3 mmol) in DMF (2 mL) for 0.5 hours at room temperature. The mixture was concentrated and then treated with 100% TFA at room temperature for 3 hours to remove the Boc protecting group. The crude mixture was concentrated by rotary evaporator and treated with α-sulfophenyl acetyl chloride (0.257 g, 1.1 mmol) and DIEA (0.522 mL, 3 mmol) in DMF (2 mL). The mixture was finally hydrolyzed by 10% LiOH and subjected to HPLC purification, and product 2-oxo-2-((4-((2-phenyl-2-sulfoacetamido)methyl)phenyl)amino)acetic acid (Lib-4) was obtained as colorless oil in 82% overall yield with >90% purity.

2-oxo-2-((4-((2-phenyl-2-sulfoacetamido)methyl)phenyl)amino)acetic acid (Lib-4): $^1$H NMR (500 MHz, DMSO-d6) δ 10.68 (s, 1H), 8.64 (t, J=5.9 Hz, 1H), 7.68 (d, J=8.6 Hz, 2H), 7.49-7.48 (m, 2H), 7.29-7.24 (m, 5H), 4.55 (s, 1H), 4.31 (dd, J=5.9, 11.1 Hz, 2H). $^{13}$C NMR (125 MHz, DMSO-d6) δ 167.5, 162.2, 156.7, 136.3, 135.6, 135.6, 129.7, 127.4, 127.3, 126.8, 120.2, 71.5, 30.7. ESI-MS Cacld. for C17H15N2O7S (M–H$^+$): m/z 391.0605; found 391.0599.

SPAA-Based Library Synthesis.

To all wells of 96-well plates were added 2-oxo-2-((4-(2-phenyl-2-sulfoacetamido)phenyl)amino)acetic acid (Lib-1) (20 μL, 20 mM in DMF), HBTU (20 μL, 20 mM in DMF), HOBt (20 μL, 20 mM in DMF), DIEA (20 μL, 60 mM in DMF), and corresponding 192 amines from storage plates (1.2 μL, 0.5 mM in DMF), the reaction plates were placed at room temperature for 1 day. Compounds from 2-oxo-2-((3-(2-phenyl-2-sulfoacetamido)phenyl)amino)acetic acid (Lib-2), 2-oxo-2-((4-(2-phenyl-2-sulfoacetamido)benzyl)amino)acetic acid (Lib-3) and 2-oxo-2-((4-((2-phenyl-2-sulfoacetamido)methyl)phenyl)amino)acetic acid (Lib-4) were synthesized by the same procedure. The reaction wells from aniline were monitored by LC-MS to show that reactions occurred well in great conversions. Thus, four libraries of 768 compounds were obtained with estimated concentration at 4 mM (assuming 80% product yield), which was screened against PTPs as described.

Synthesis of Compounds 2-7.

To 2-oxo-2-((4-(2-phenyl-2-sulfoacetamido)phenyl)amino)acetic acid (Lib-1) (0.0756 g, 0.2 mmol) in DMF (2 mL) was added HBTU (0.078 g, 0.2 mmol), HOBt (0.031 g, 0.2 mmol), DIEA (0.105 mL, 0.6 mmol), and 4-iodoaniline (0.053 g, 0.22 mmol) sequentially, and the reaction mixture was stirred at room temperature for 1 hour. The mixture was then subjected to HPLC purification, and product 2-((4-(2-((4-iodophenyl)amino)-2-oxoacetamido)phenyl)amino)-2-oxo-1-phenylethanesulfonic acid (2) was obtained as colorless oil (97% yield, >95% purity). Products 3 to 7 were obtained in the same manner.

2-((4-(2-((4-iodophenyl)amino)-2-oxoacetamido)phenyl)amino)-2-oxo-1-phenylethanesulfonic acid (2): $^1$H NMR (500 MHz, DMSO-d6) δ 10.91 (s, 1H), 10.77 (s, 1H), 10.33 (s, 1H), 7.78 (d, J=8.9 Hz, 2H), 7.73-7.68 (m, 4H), 7.60-7.58 (m, 4H), 7.30-7.25 (m, 3H), 4.78 (s, 1H). $^{13}$C NMR (125 MHz, DMSO-d6) δ 165.9, 158.9, 158.1, 137.6, 137.4, 135.8, 135.2, 132.8, 129.9, 127.4, 126.9, 122.6, 120.9, 119.1, 88.7, 71.8. ESI-MS Cacld. for C22H17IN3O6S (M–H$^+$): m/z 577.9888; found 577.9883.

2-oxo-2-((4-(2-oxo-2-((4-(thiophen-2-yl)phenyl)amino)acetamido)phenyl)amino)-1-phenylethanesulfonic acid (3): $^1$H NMR (300 MHz, DMSO-d6) δ 10.90 (s, 1H), 10.82 (s, 1H), 10.33 (s, 1H), 7.93-7.73 (m, 13H), 7.64-7.26 (m, 3H), 4.73 (s, 1H). ESI-MS Cacld. for C26H20N3O6S2 (M–H$^+$): m/z 534.0799; found 534.0799.

2-((4-(2-((3-(4-bromophenyl)-1H-pyrazol-5-yl)amino)-2-oxoacetamido)phenyl)amino)-2-oxo-1-phenylethanesulfonic acid (4): $^1$H NMR (300 MHz, DMSO-d6) δ 11.00 (s, 1H), 10.80 (s, 1H), 10.32 (s, 1H), 7.79-7.54 (m, 10H), 7.28-7.26 (m, 3H), 6.92 (s, 1H), 4.71 (s, 1H). ESI-MS Cacld. for C25H9BrN5O6S (M–H$^+$): m/z 596.0245; found 596.0253.

2-((4-(2-([1,1'-biphenyl]-4-ylamino)-2-oxoacetamido)phenyl)amino)-2-oxo-1-phenylethanesulfonic acid (5): $^1$H NMR (300 MHz, DMSO-d6) δ 10.92 (s, 1H), 10.81 (s, 1H), 10.31 (s, 1H), 7.96-7.26 (m, 18H), 4.72 (s, 1H). ESI-MS Cacld. for C28H22N3O6S (M–H$^+$): m/z 528.1235; found 528.1231.

2-((4-(2-((4-isopropylphenyl)amino)-2-oxoacetamido)phenyl)amino)-2-oxo-1-phenylethanesulfonic acid (6): $^1$H NMR (300 MHz, DMSO-d6) δ 10.78 (s, 1H), 10.74 (s, 1H), 10.33 (s, 1H), 7.80-7.73 (m, 4H), 7.59-7.56 (m, 4H), 7.25-7.22 (m, 5H), 4.73 (s, 1H), 2.91-2.82 (m, 1H), 1.19 (d, J=9.0 Hz, 6H). ESI-MS Cacld. for C25H24N3O6S (M–H$^+$): m/z 494.1391; found 494.1394.

2-oxo-2-((4-(2-oxo-2-(phenylamino)acetamido)phenyl)amino)-1-phenylethanesulfonic acid (7): $^1$H NMR (300 MHz, DMSO-d6) δ 10.80 (s, 2H), 10.34 (s, 1H), 7.87-7.78 (m, 4H), 7.60-7.56 (m, 4H), 7.40-7.27 (m, 6H), 4.78 (s, 1H). $^{13}$C NMR (75 MHz, DMSO-d6) δ 166.3, 159.2, 158.8, 138.1, 136.3, 135.6, 133.4, 130.3, 129.2, 127.9, 127.4, 125.1, 121.3, 120.9, 119.6, 72.1. ESI-MS Cacld. for C22H18N3O6S (M−H⁺): m/z 452.0922; found 452.0917.

Results and Discussion

Identification and Characterization of Cefsulodin as a SHP2 Inhibitor.

Figure 14:
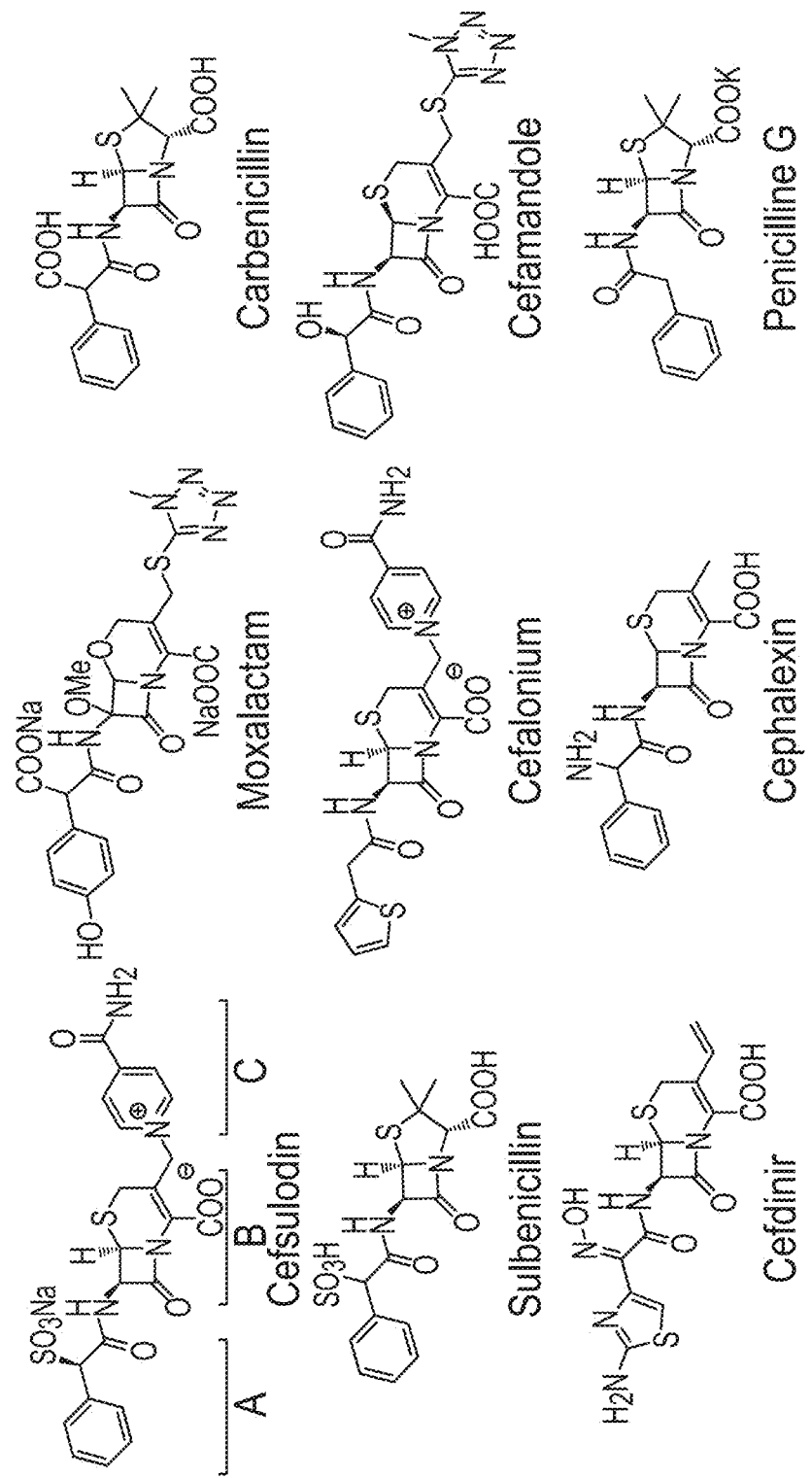
FIG. 14 depicts the chemical structures of cefsulodin and several related β-lactam antibiotics. Cefsulodin is composed by 3 parts: sulfonic acid head group A, β-lactam core B, and isonicotinamide tail C. Moxalactam is the only compound with all 3 parts, carbenicillin and sulbenicillin have A and B parts, cefalonium and cefamandole have parts B and C, while cefdinir, cephalexin and penicillin G just have part B, β-lactam core.
Figure 15:
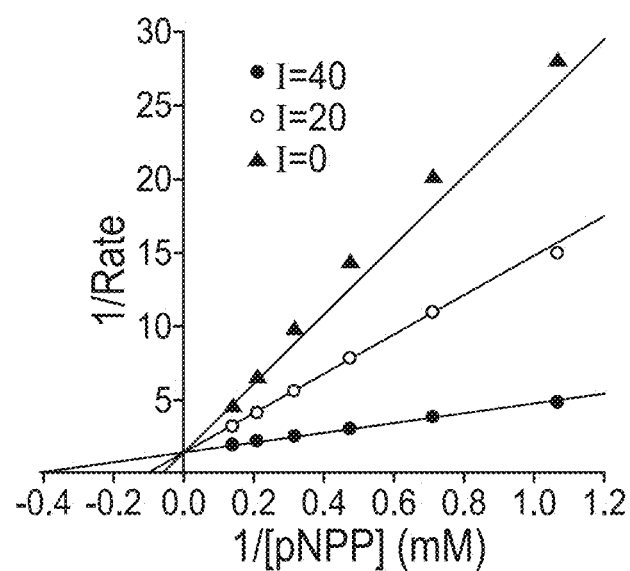
FIG. 15 depicts Lineweaver-Burk plot for cefsulodin-mediated SHP2 inhibition as analyzed in Example 9. Cefsulodin is a competitive inhibitor of SHP2 with Ki at 6.6 μM. Cefsulodin concentrations were 0 (Δ), 20 (○) and 40 (●) μM.

To identify SHP2 inhibitory agents with improved bioavailability, 1,850 FDA-approved clinical drugs from the Johns Hopkins Drug Library were screened against the catalytic domain of SHP2 using a phosphatase activity-based assay. The drugs were assayed at both 10 and 20 µM concentrations at 25° C. and pH 7.0 in a buffer containing 50 mM 3,3-dimethylglutarate and 1 mM EDTA with an ionic strength of 0.15 M adjusted by addition of NaCl. Positive hits were selected based on a decrease in absorbance that corresponds to a decline in the hydrolysis of the substrate para-nitrophenyl phosphate (pNPP). Cefsulodin (structure shown in FIG. 14), a third generation β-lactam cephalosporin antibiotic with a narrow spectrum restricted to *Pseudomonas Aeruginosa*, surfaced as a top hit against SHP2. Kinetic measurements with repurchased samples of cefsulodin confirmed its SHP2 inhibitory activity with an $IC_{50}$ value of 16.8±2.0 µM under the assay conditions described above. Lineweaver-Burk plot analysis revealed that the mode of SHP2 inhibition by cefsulodin is competitive with respect to the substrate pNPP with a $K_i$ of 6.6±0.2 µM (FIG. 15).

Figure 16A:
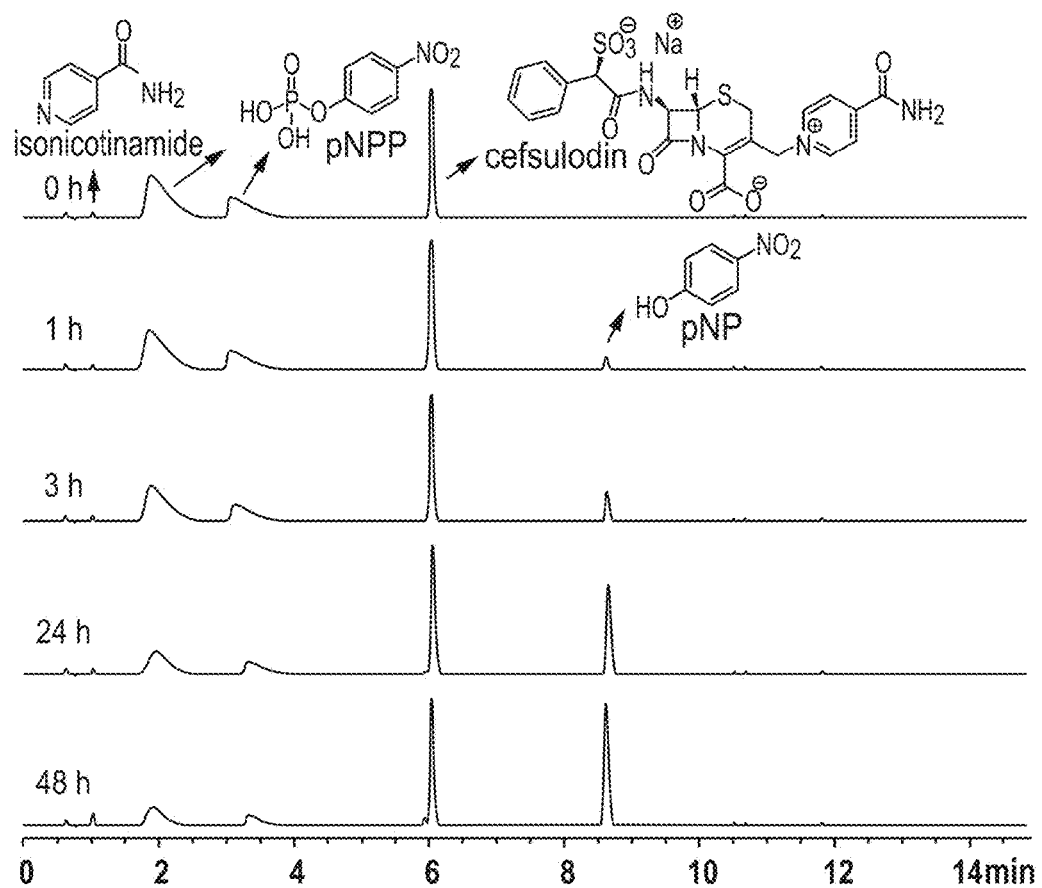
FIGS. 16A & 16B depict LC-MS characterization of SHP2 inhibition by cefsulodin as analyzed in Example 9. LC-MS showed that cefsulodin is not inhibiting SHP2 by covalent modification.
Figure 16B:
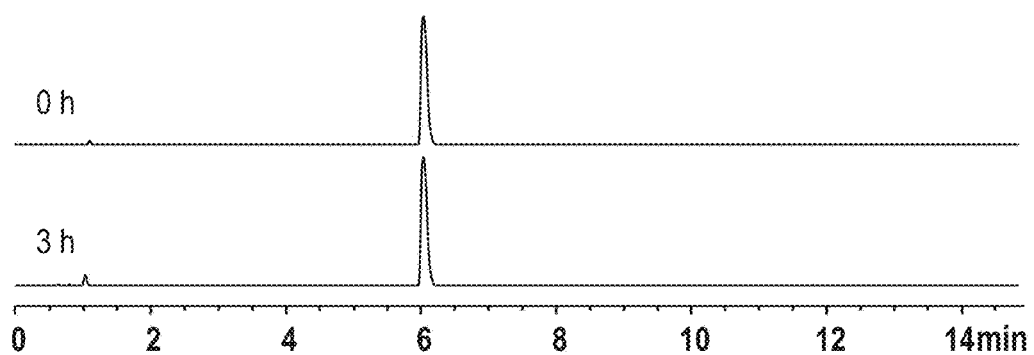

The reactivity of β-lactam ring is important for β-lactam antibiotics' therapeutic activity, but also makes them vulnerable to hydrolysis and attack by various nucleophiles. Since the PTP-catalyzed reaction employs nucleophic catalysis, it was determined whether cefsulodin acts as an irreversible inhibitor and inactivates SHP2 by a covalent mechanism. To this end, the $IC_{50}$ of cefsulodin against SHP2 was re-measured under the same assay conditions by either incubating cefsulodin with SHP2 for 30 minutes prior to the addition of pNPP, or incubating cefsulodin with pNPP for 30 minutes prior to the addition of SHP2. Reversible and fast-binding inhibitors are not expected to display time dependency, whereas irreversible or tight-binding inhibitors will exhibit significantly reduced $IC_{50}$ values when they are pre-incubated with the enzyme. Similar $IC_{50}$ values were obtained for cefsoludin under both conditions (cefsoludin pre-mixed with SHP2, $IC_{50}$=16.8±1.8 µM; cefsoludin pre-mixed with pNPP, $IC_{50}$=17.5±2.0 µM), suggesting that cefsulodin does not inactivate SHP2, at least not within the duration of the assay time. SHP2-catalyzed pNPP hydrolysis in the presence of cefsulodin was also monitored by LC-MS as a function of time at the same pH and temperature (FIGS. 16A & 16B). No evidence of SHP2 modification was observed and no change in cefsulodin concentration was evident.

Figure 17A:
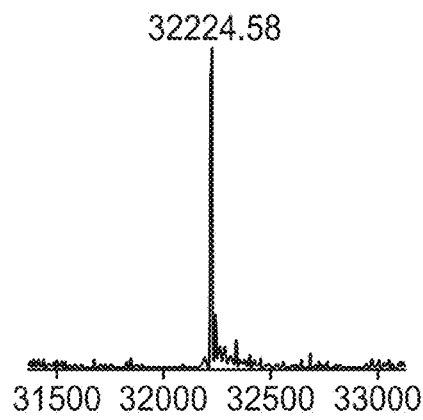
FIGS. 17A-17D depict QTOF-MS characterization of SHP2 inhibition by cefsulodin as analyzed in Example 9.
Figure 17B:
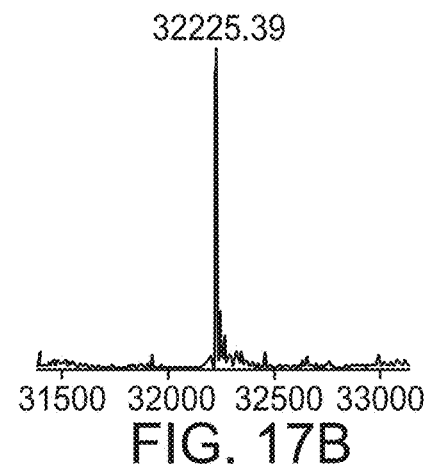
Figure 17C:
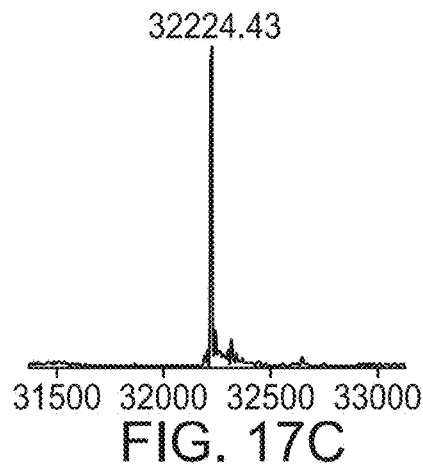
Figure 17D:
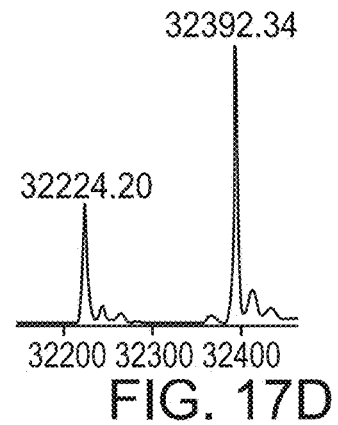

Finally, SHP2 (100 nM and 10 nM) was incubated with 100 µM cefsulodin for three hours and the mixtures were analyzed by QTOF ESI-MS (FIGS. 17A-17D). The results showed no covalent adduct formation between SHP2 and cefsulodin. As a positive control, phenyl vinyl sulfone, a known PTP activity-based probe that covalently modifies the catalytic cysteine, formed a covalent adduct with SHP2 within 10 minutes (FIG. 17D). Taken together, these studies indicated that cefsulodin is a competitive and reversible SHP2 inhibitor.

To assess the specificity of cefsulodin for SHP2, its inhibitory activity toward a panel of mammalian PTPs, including cytosolic PTPs, SHP1, PTP1B, LYP, HePTP, and PTP-Meg2, receptor-like PTPs, CD45, PTPα, PTPβ, PTPε, PTPγ, PTPµ and LAR, dual specificity phosphatases VHR and CDC14A, low molecular weight (LMW) PTP, and a protein Ser/Thr phosphatase PP5, were measured. As shown in Table 18, cefsulodin is quite selective for SHP2, displaying, with one exception, greater than 10-fold selectivity against all PTPs examined. The sole exception is SHP1, which exhibits high sequence identity to SHP2. Cefsulodin shows similar inhibitory activity toward SHP1 with an $IC_{50}$ of 21±3.0 µM.

TABLE 18

The IC50 values of cefsulodin and novel SHP2 inhibitors against a panel of PTPs. All measurements were made in a pH 7.0 buffer containing 50 mM 3,3-dimethylglutarate and 1 mM EDTA with an ionic strength of 0.15M adjusted by addition of NaCl, using pNPP as substrate.

| Enzyme | Cefsulodin | 2 | 3 | 4 | 5 | 6 |
|---|---|---|---|---|---|---|
| SHP2 | 16.8 ± 2.0 | 1.51 ± 0.06 | 0.90 ± 0.1 | 0.73 ± 0.02 | 1.36 ± 0.04 | 2.33 ± 0.04 |
| SHP1 | 21.0 ± 3.0 | 7.33 ± 1.3 | 2.6 ± 0.04 | 6.0 ± 0.02 | 4.8 ± 1.1 | 6.0 ± 0.02 |
| PTP1B | 190 ± 18 | 9.3 ± 2.0 | 4.2 ± 1.0 | 7 ± 1 | 3.0 ± 0.06 | 7 ± 1 |
| LYP | >200 | >10 | >10 | >10 | >10 | >10 |
| HePTP | 250 ± 20 | >10 | >10 | >10 | >10 | >10 |
| PTP-Meg2 | 350 ± 20 | >10 | >10 | >10 | >10 | >10 |
| CD45 | 390 ± 40 | 6.6 ± 2 | 2.5 ± 0.08 | 6.7 ± 2 | 3.8 ± 1.0 | 3.7 ± 0.08 |
| PTPα | >200 | >10 | >10 | >10 | >10 | >10 |
| PTPβ | >200 | >10 | >10 | >10 | >10 | >10 |
| PTPε | >200 | >10 | >10 | >10 | >10 | >10 |
| PTPγ | >200 | >10 | >10 | >10 | >10 | >10 |
| PTPµ | >200 | >10 | >10 | >10 | >10 | >10 |
| LAR | >200 | >10 | >10 | >10 | >10 | >10 |
| VHR | >200 | >10 | >10 | >10 | >10 | >10 |
| CDC14A | 300 ± 50 | >10 | >10 | >10 | >10 | >10 |
| LMWPTP | >200 | >10 | >10 | >10 | >10 | >10 |
| PP5 | >200 | >10 | >10 | >10 | >10 | >10 |

To understand the structure and activity relationship of cefsoludin-mediated SHP2 inhibition, several related β-lactam antibiotics, including moxalactam, carbenicillin, sulbenicillin, cefalonium, cefamandole, cefdinir, cephalexin, and penicillin G, were acquired. Cefsulodin was dissected into 3 parts: the sulfonic acid head group A, the fused β-lactam core B, and the isonicotinamide tail C (FIG. 14). Moxalactam is the only compound that possesses all three parts; carbenicillin and sulbenicillin contain parts A and B; cefalonium and cefamandole have parts B and C; and cefdinir, cephalexin and penicillin G have just part B, the β-lactam core. Interestingly, when measured at 200 µM compound concentration, moxalactam was the only one that exhibited modest inhibition against SHP1, with an $IC_{50}$ of 170 µM. None of the other β-lactam antibiotics displayed any inhibition against SHP2 at 200 µM, indicating that the structural integrity of cefsulodin is necessary for SHP2 inhibition.

X-Ray Crystal Structure of SHP2 in Complex with Cefsulodin and Identification of Sulfo Phenyl Acetic Amide (SPAA) as a Novel pTyr Mimetic.

Figure 18A:
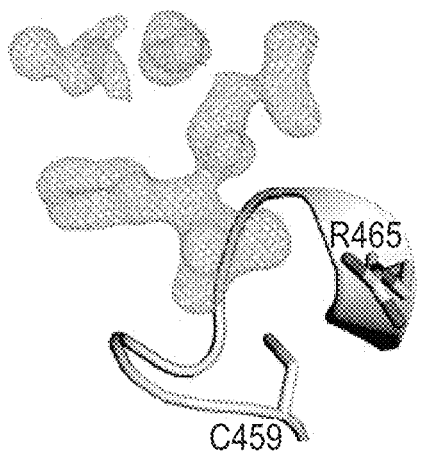
FIGS. 18A-18F depict the co-crystal structure of SHP2 with altered cefsulodin.
Figure 18B:
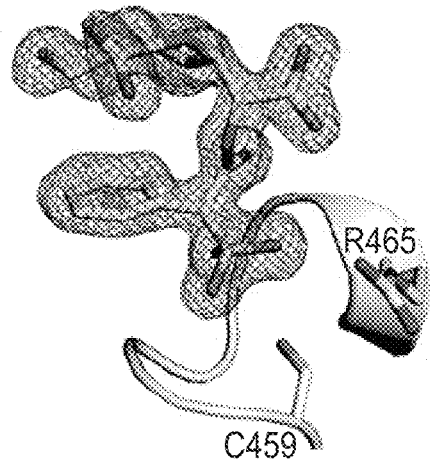

To define the molecular basis for SHP2 inhibition by cefsulodin and to guide the design of new cefsulodin-based SHP2 inhibitors with improved potency and selectivity, the crystal structure of SHP2 catalytic domain (residues 262-528) in complex with cefsulodin at 1.6 Å resolution was determined. Data collection and structure refinement statistics are summarized in Table 19. The structure was refined to $R_{work}/R_{free}$ of 17.6%/20.5%. The SHP2.cefsulodin complex crystallized in the $P2_1$ space group with one molecule per asymmetric unit. The overall structure is very similar to the reported apo-SHP2 structure (PDBID: 3B7O) used for molecular replacement, with an RMSD of 0.523 Å for 256 Cα atoms. The presence of a small molecule in SHP2 active site was unambiguously identified by the strong positive Fo-Fc electron density around the catalytic P-loop (FIG. 18A). The small molecule binding mode was iteratively built, refined, and confirmed by excellent 2Fo-Fc electron density contoured at 1.0σ (FIG. 18B).

TABLE 19

Data collection and structure refinement statistics SHP2•Cefsulodin

| Data Collection | |
|---|---|
| Space group | $P2_1$ |
| Cell dimensions | |
| a, b, c (Å) | 39.64, 75.27, 48.05 |
| α, β, γ (°) | 90.0, 99.1, 90.0 |
| Resolution (Å) | 1.60 (1.63-1.60) |
| $R_{merge}$ | 0.077 (0.666) |
| I/σI | 22.1 (1.5) |
| Completeness (%) | 97.3 (80.0) |
| Redundancy | 3.4 (2.7) |
| Refinement | |
| Resolution (Å) | 1.60 |
| No. reflections | 35,592 |
| $R_{work}/R_{free}$ | 0.176/0.205 |
| No. atoms | |
| Protein | 2,156 |
| Ligand | 29 |
| Water | 364 |
| R.m.s. deviations | |
| Bond lengths (Å) | 0.007 |
| Bond angles (°) | 1.183 |
| Ramachandran plot (%) | |
| Most favored regions | 90.3 |
| Additional allowed regions | 8.0 |
| Generously allowed regions | 1.7 |
| Disallowed regions | 0 |

The dataset was collected from a single crystal. Values in parentheses are for highest-resolution shell.

Figure 18C:
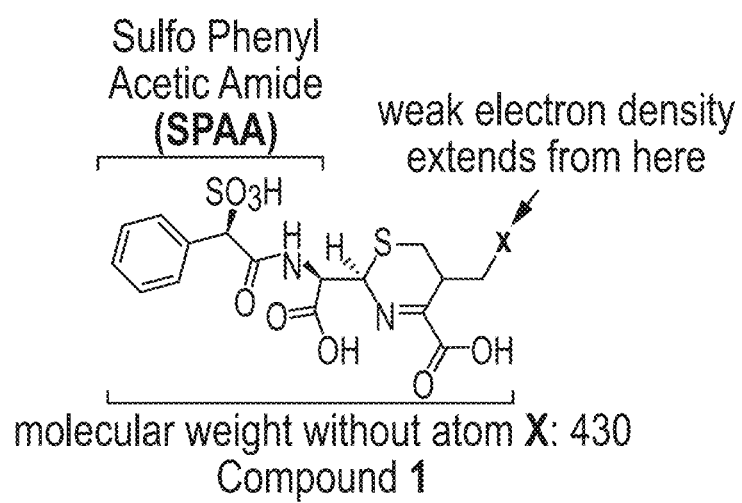
Figure 18F:
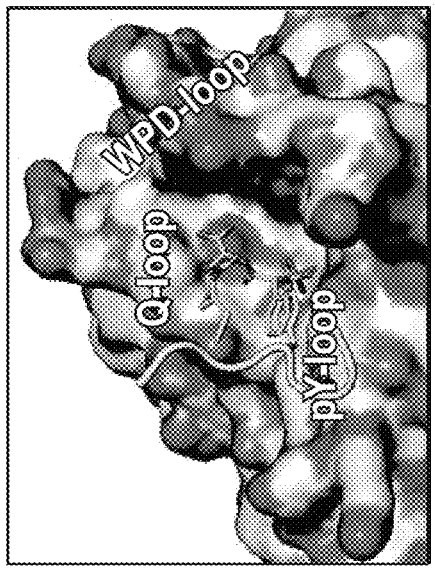
Figure 18E:
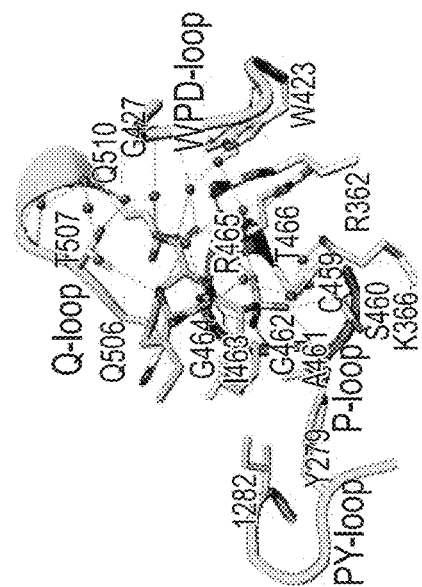
Figure 18D:
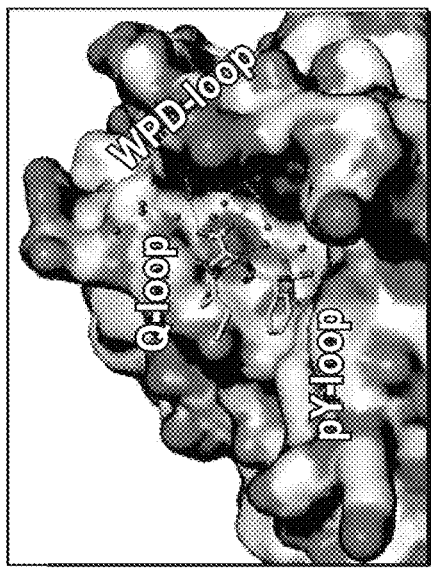

Unexpectedly, the small molecule observed in the SHP2 co-crystal structure is not the original cefsulodin but an altered form of the drug: the β-lactam core (part B) is opened, and the isonicotinamide moiety (part C) is not visible in the structure. This altered form (compound 1, FIG. 18C) is situated in the SHP2 active site with abundant interactions with the P-loop, pY recognition loop, Q-loop and WPD-loop (FIG. 18D). In detail (FIG. 18E), the sulfonic acid is in close proximity to the catalytic P-loop and forms multiple hydrogen bonds with the backbone amides of S460, A461, I463, G464 and R465, as well as two water-mediated hydrogen bonds with the R465 and K366 side chains. The a-benzene ring is located within a hydrophobic pocket constituted by A461, I463, I282 and Y279, which normally functions to recognize and stabilize the tyrosine ring of PTP substrates during catalysis. Superimposition of the SHP2.cefsulodin structure with a previously reported PTP1B.phosphopeptide structure (PDBID: 1EEN) revealed that the Sulfo Phenyl Acetic Amide (SPAA) motif overlaps very well with pTyr in the phosphopeptide (FIG. 18F). In addition, the newly formed carboxylic acid, as a result of β-lactam ring opening, makes multiple water bridged polar interactions with W423 and G427 in the WPD loop as well as T507 and Q510 in the Q-loop. This orientation also forces the 6-membered thiazine ring including the terminal carboxylic acid group to point out of the active site with no obvious interactions with SHP2 residues.

Figure 19A:
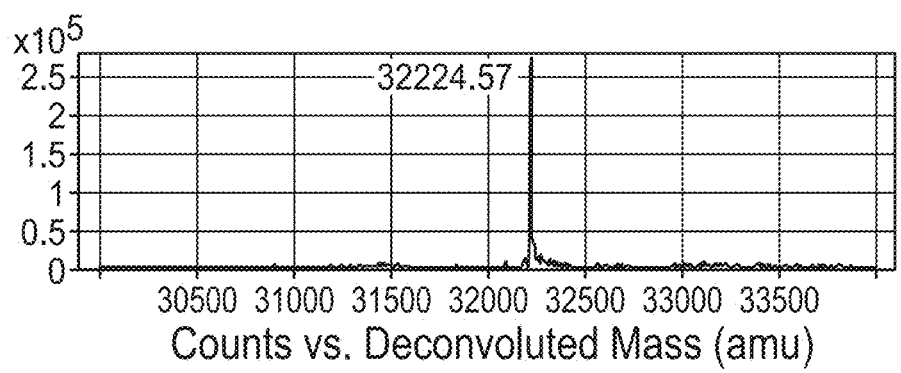
FIGS. 19A & 19B depict QTOF ESI-MS studies of re-dissolved crystals.
Figure 19B:
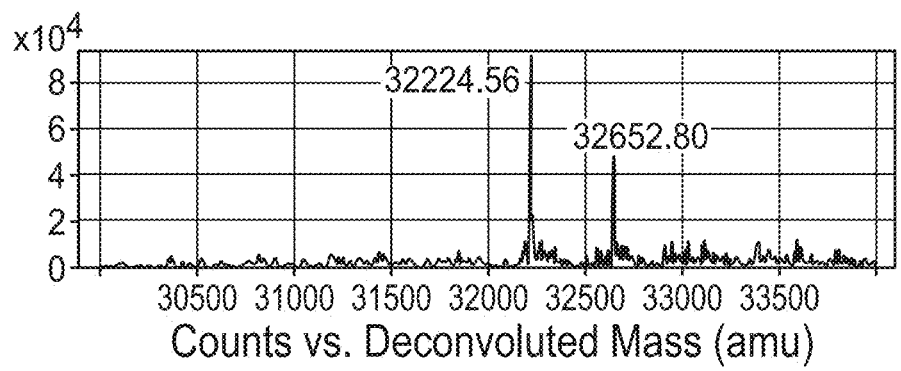
Figure 20A:
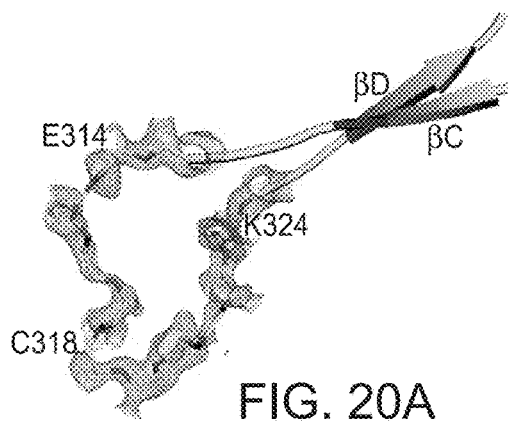
FIGS. 20A-20C depict structure refinement, which shows the existence of covalent bond between compound 1 and C318 residue of SHP2.
Figure 20B:
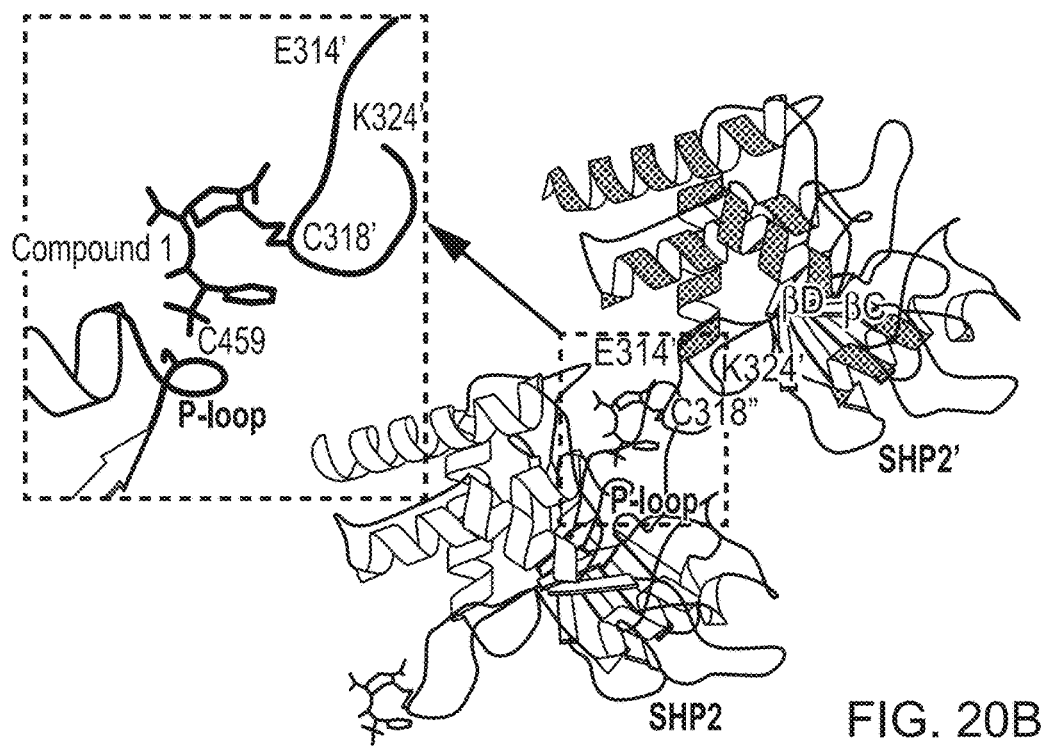
Figure 20C:
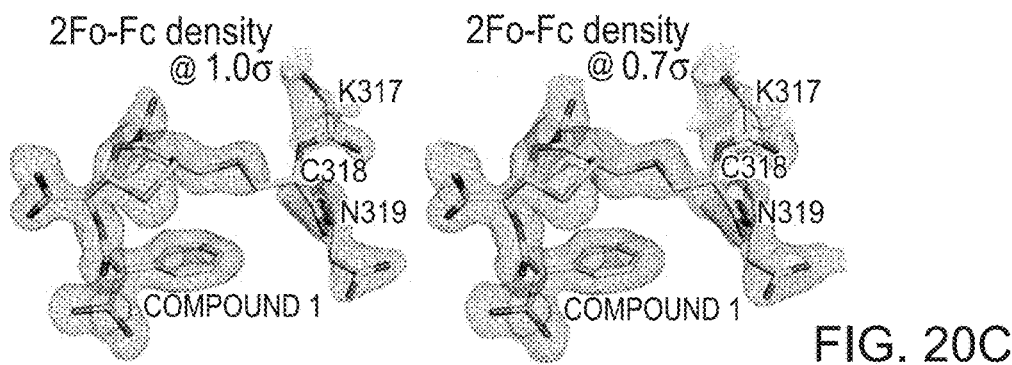

Further inspection of the 2Fo-Fc map at 0.76 revealed weak electron density extending from atom X (FIG. 18C) to a space where a flexible loop (residues 314 to 324), which has not been observed in previously reported SHP2 structures, from a symmetry-related SHP2 molecule. Whether a covalent bond was formed between compound 1 and SHP2 was then investigated. Thus, co-crystals of the SHP2.cefsulodin complex were collected, washed and re-dissolved in water, and the resulting solution was subjected to QTOF ESI-MS analysis. As a control, apo-SHP2 crystals were also processed and analyzed in the same way. As shown in FIG. 19A, the re-dissolved apo-SHP2 crystals show only one peak at 32224.57, which corresponds to the molecular mass of the SHP2 catalytic domain (residue 262-528). In contrast, the re-dissolved co-crystals of SHP2 and cefsulodin had an additional peak at 32652.80 (FIG. 19B), and the difference between these two peaks is 428.24, which corresponds to the molecular mass of compound 1 minus two hydrogen atoms, likely as a result of covalent bond formation with SHP2. To identify the residue covalently attached to compound 1, the missing loop (residue 314 to 324) was re-constructed based on the 2Fo-Fc electron density observed at 0.76 through iterative cycles of building and refinement (FIG. 20A). Through crystallographic symmetry operations, the atom X was found to overlap nicely with the sulfur atom in C318 from the flexible loop in a symmetry-related SHP2 molecule (FIG. 20B), and the 2Fo-Fc electron density at 0.76 adequately accounts for every atom of C318, supporting the existence of a covalent bond between the SHP2 active site bound compound 1 and a symmetry-related SHP2 molecule in the co-crystal (FIG. 20C).

One plausible explanation for the apparent contradictory findings that cefsulodin acts as a reversible and competitive SHP2 inhibitor in assay solution but forms a covalent adduct with SHP2 in the crystalline state may be that cefsulodin covalently modifies SHP2 during the crystallization process. Cefsulodin is most stable under pH 4-6 but readily degrades when the pH is over 7, a process which could be accelerated by the presence of strong nucleophiles. As mentioned above, there are two reactive sites in cefsulodin (β-lactam core and isonicotinamide), and the loss of isonicotinamide precedes β-lactam ring opening due to higher reactivity.

Figure 21A:
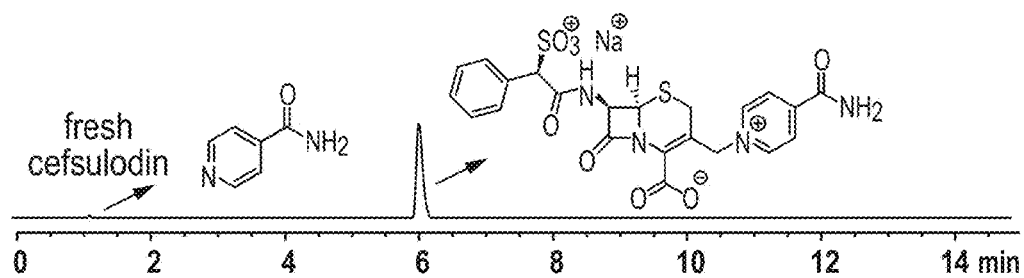
FIGS. 21A-21E depict cefsulodin stability under various conditions as analyzed in Example 9.
Figure 21B:
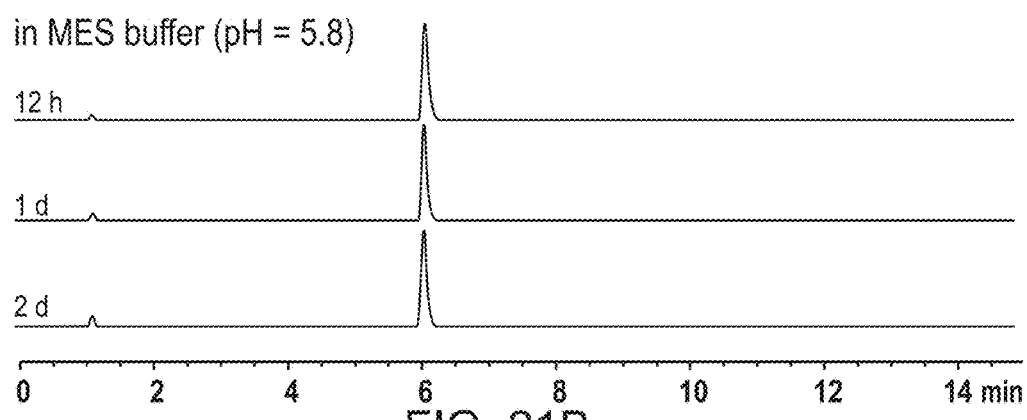
Figure 21C:
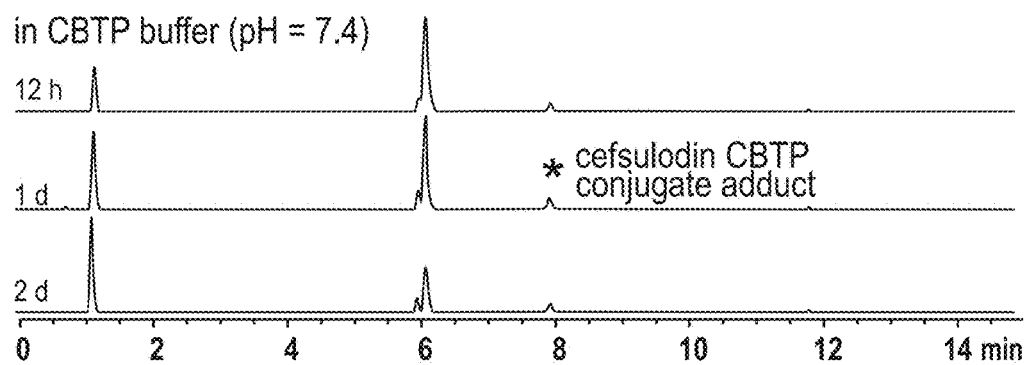
Figure 21D:
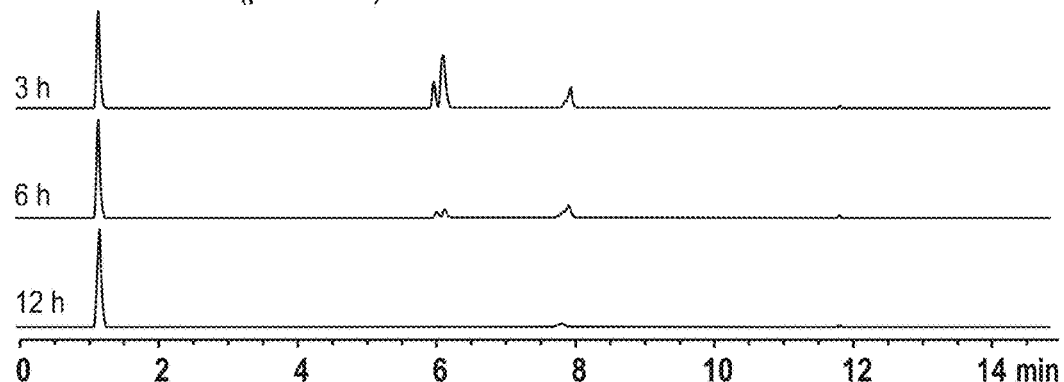

LC-MS was used to study cefsulodin stability in different buffer solutions (FIGS. 21A-21E). Consistent with previous reports that cefsulodin stability is highly pH dependent, degradation of cefsulodin was negligible when monitored in pH 5.8 MES buffer (20 mM MES, 250 mM NaCl, 1 mM EDTA) (FIG. 21B). In contrast, cefsulodin degradation was obvious in pH 7.4 CBTP buffer (33 mM Citric acid, 67 mM BIS-TRIS Propane) (FIG. 21C), and its degradation was further accelerated in CBTP buffer at pH 9.1 (FIG. 21D).

Figure 21E:
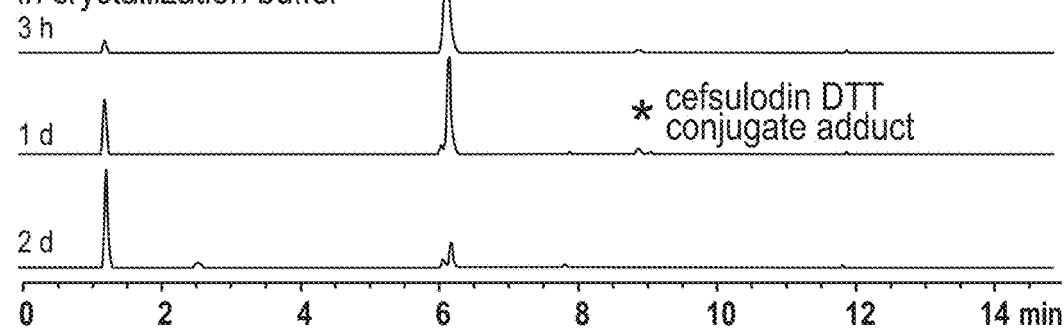

In the crystallization experiment, the MES (pH 5.8) buffer containing 0.2 mM SHP2, 1 mM cefsulodin and 2 mM DTT was mixed with an equal volume of the CBTP buffer (pH 7.4), and the resulting solution (final pH=7.1) was allowed to stand at 20° C. for several days. Under this condition, cefsulodin was found to be completely degraded within 2 days (FIG. 21E). In addition, conjugate adducts of cefsulodin with either CBTP or DTT (FIGS. 22A and 22B) could be detected in the cefsulodin samples stored in the pH 7.4 CBTP buffer (FIG. 22C) and under crystallization conditions (FIG. 21E). Given the similar nucleophilicity of the Cys side chain and DTT, and the proximity of C318 to the isonicotinamide group in the crystal, it is reasonable to speculate that upon cefsulodin binding to the SHP2 active site in the crystalline state, the isonicotinamide tail in cefsulodin is poised to be replaced by C318 from a nearby symmetry-related SHP2 molecule, and the β-lactam ring is subsequently opened by water to form the SHP2-compound 1 adduct as observed in the crystal structure (FIGS. 20A-20C).

Binding Mode Between Cefsulodin and SHP2.

Figure 23A:
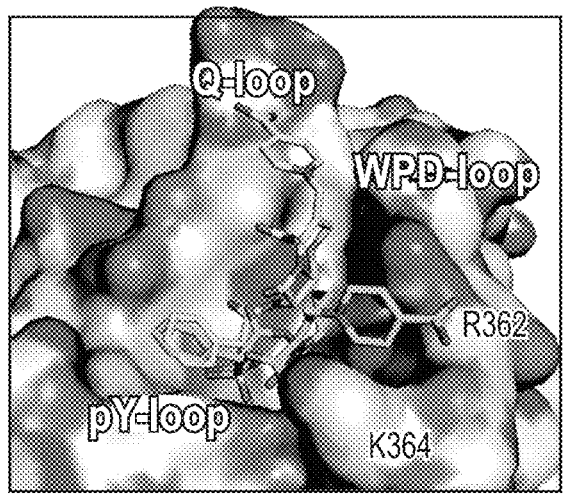
FIGS. 23A & 23B depict the predicted binding modes of intact cefsulodin in complex with SHP2.

Given the observations that cefsulodin acts as a reversible and competitive inhibitor for SHP2 under assay conditions, further insight into the binding mode between SHP2 and the intact cefsulodin molecule was obtained using molecular modeling to investigate the binding mode between the two molecules. To avoid bias introduced from the SHP2.compound 1 structure, a previously reported apo-SHP2 structure (PDB ID: 3B7O) was used for modeling. The top-two binding modes with indistinguishable calculated binding energies are shown in FIG. 23A. In both cases, cefsulodin binds SHP2 with the SPAA head group sticking into the active site, similar to what was observed in the SHP2.compound 1 structure. However, the rest of cefsulodin has a different binding mode in comparison to that of compound 1. This difference could be explained by the conformational restraints imposed by the intact β-lactam ring, which forces the thiazine pointing away from the SPAA head, making it impossible to form a sandwich-like intramolecular conformation as observed in the SHP2.compound 1 structure. Moreover, the orientation of the isonicotinamide tail in the two predicted binding modes are different (FIG. 23A): it either extends to the Q-loop and WPD-loop in mode I, and/or to the WPD-loop and residues 360 to 366 in mode I. Specifically, either residue E508 in mode I or R362 in mode II forms polar interactions with the terminal amide of cefsulodin, which serves as an anchor to control the orientation of isonicotinamide tail.

Figure 23B:
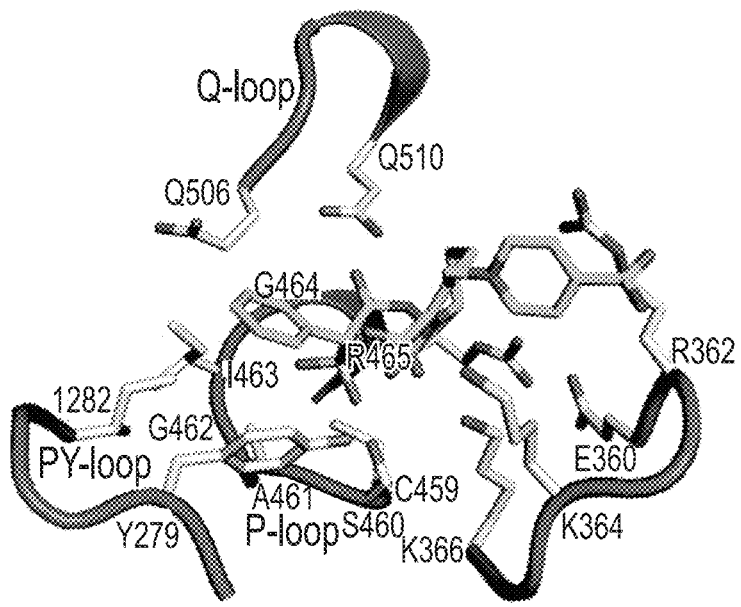

To differentiate and validate the predicted binding modes for cefsulodin, mutants, SHP2/E508A and SHP2/R362A, were generated and their kinetic parameters, including $k_{cat}$, $K_m$ for pNPP and $IC_{50}$ for cefsulodin, were determined. SHP2/E508A and SHP2/R362A displayed nearly identical $k_{cat}$ and $K_m$ to those of the wild-type enzyme, indicating that neither residue is essential for SHP2 folding and catalysis. Interestingly, point mutation to convert residue E508 to alanine did not affect inhibition by cefsulodin ($IC_{50}$ values for wild-type SHP2 and E508A are 16.7±2.0 μM and 19.0±1.0 μM, respectively), whereas replacement of R362 with alanine increased the $IC_{50}$ for cefsulodin (46.5±4.9 μM) by 3-fold. These results indicate that R362, not E508, likely participates in binding cefsulodin and suggest that mode II (FIG. 23B) may be the preferred SHP2 binding mode for cefsulodin. In this binding mode, the isonicotinamide tail is oriented by the rigid β-lactam ring and sandwiched by R362 and K364. The carboxylic acid on the β-lactam ring forms polar interactions with the side chains of K364 and K366. Similar to the observed interactions between SPAA and the active site in the SHP2.compound 1 structure, the sulfonic acid in cefsulodin is tightly anchored by the P-loop through numerous H-bonds with the backbone amides, and the α-benzene ring is situated within a hydrophobic pocket formed by residues Y279, I282, A461 and I463. Collectively, the interaction profiles between SHP2 and compound 1/cefsulodin, as well as structural comparison with the PTP1B.phosphopeptide complex, identify SPAA as a unique pTyr mimetic, which could be used for the design and development of novel sulfonic acid based PTP inhibitors.

A Structure-Guided SPAA Fragment-Based Approach for SHP2 Inhibitor Development.

Figure 24A:
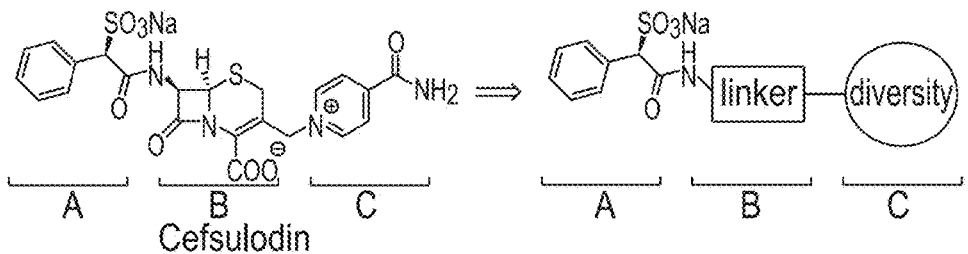
FIGS. 24A-24C depict the design and synthesis of SPAA based novel SHP2 inhibitors.
Figure 24B:
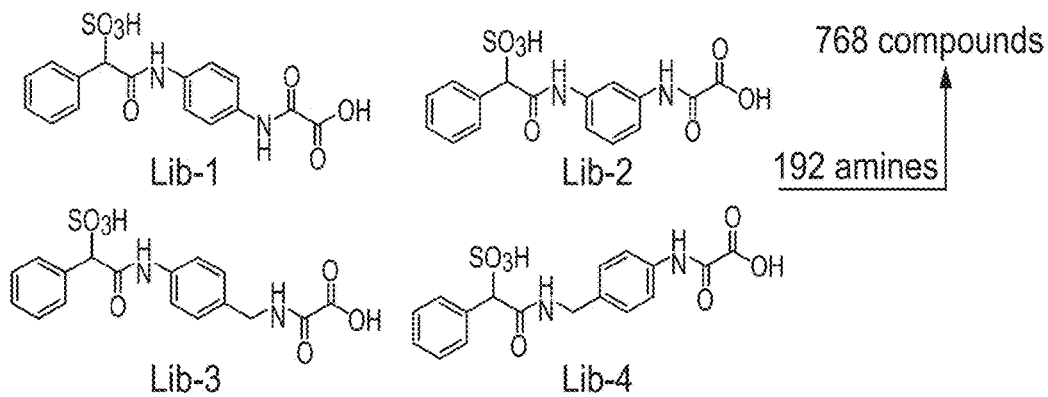
Figure 24C:
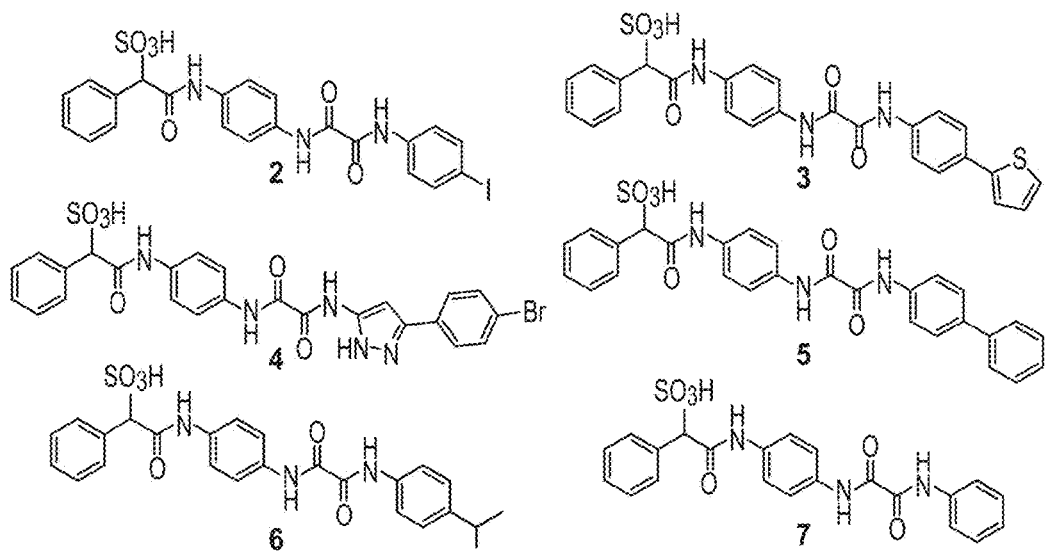

Given cefsulodin's chemical reactivity and its modest potency and selectivity for SHP2 (especially vs SHP1), SHP2 inhibitors with improved chemical stability and inhibitory activity were designed and synthesized based on the structural insights obtained above. As shown in FIGS. 24A-24C, cefsulodin consists of three parts: part A (SPAA) is essential for SHP2 inhibitory activity as it binds the active site; part B functions as a linker to connect part C; and part C interacts with residues 362-365 in the $\beta_5$-$\beta_6$ loop. To target both SHP2 active site and adjacent less-conserved pockets, SPAA-based compound libraries were prepared using appropriately functionalized linkers to replace the chemically reactive part B and to introduce structural diversity (FIG. 24A).

Figure 25A:
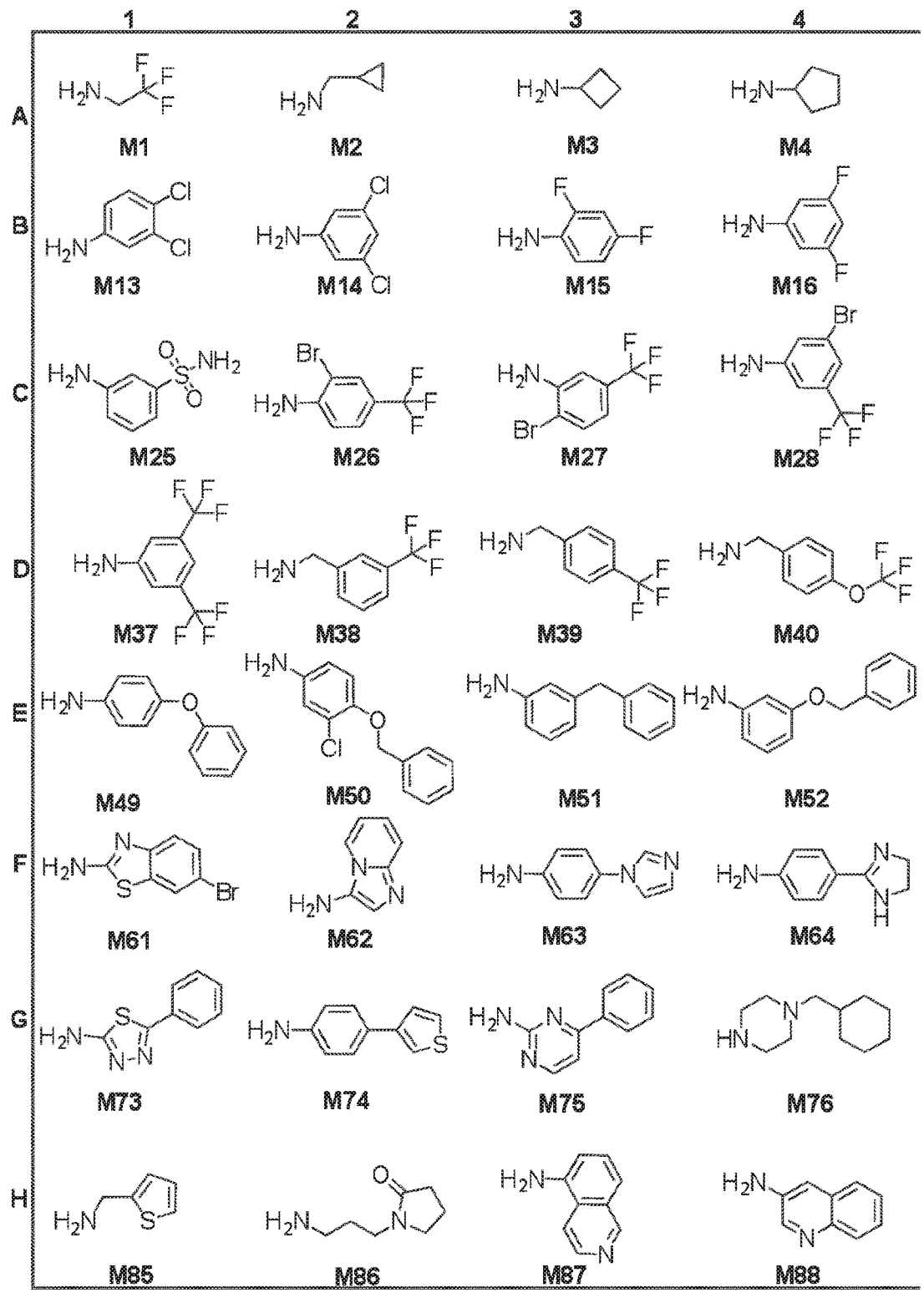
FIGS. 25A & 25B depict chemical structures of a set of 192 amines.
Figure 25A:
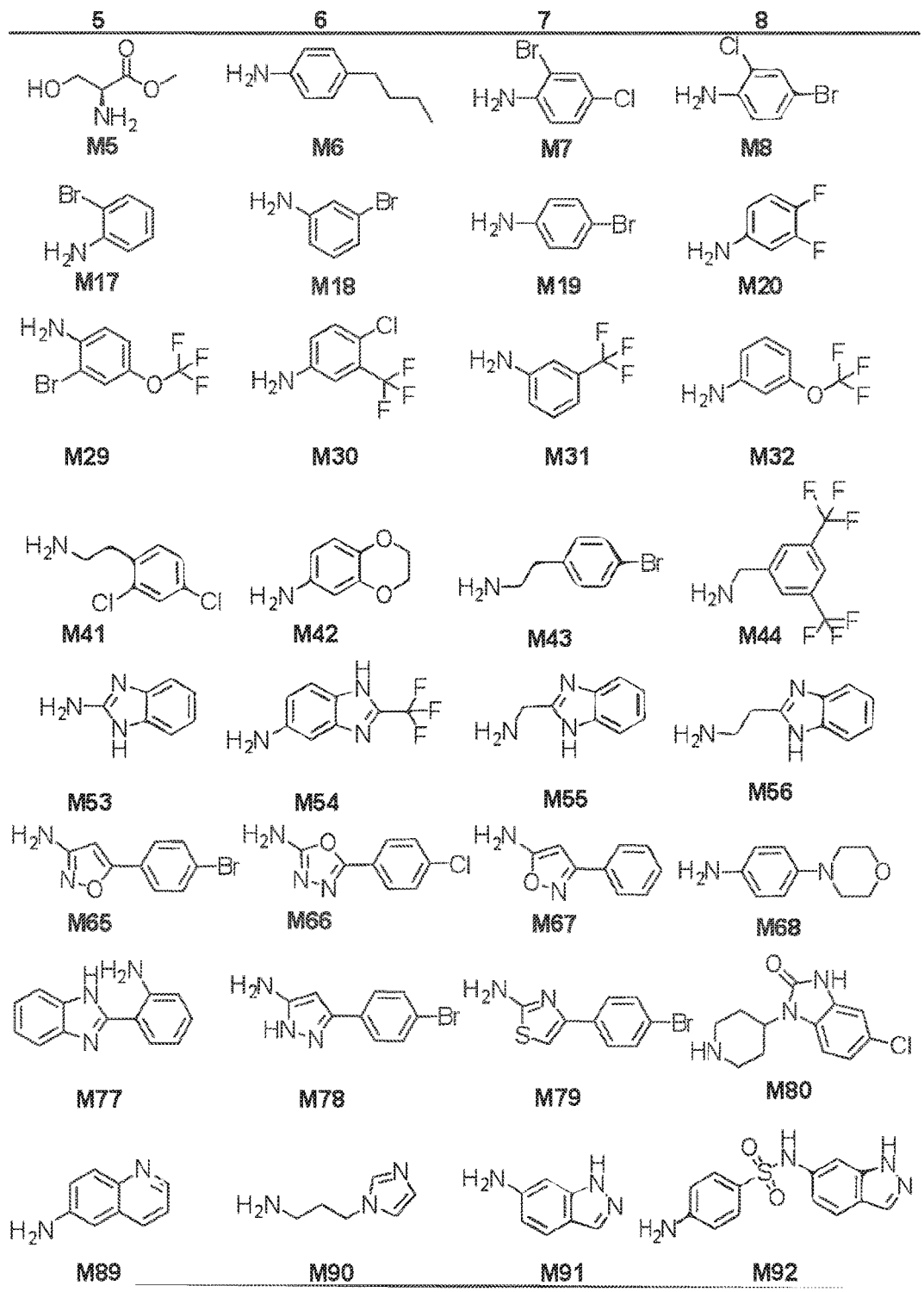
Figure 25A:
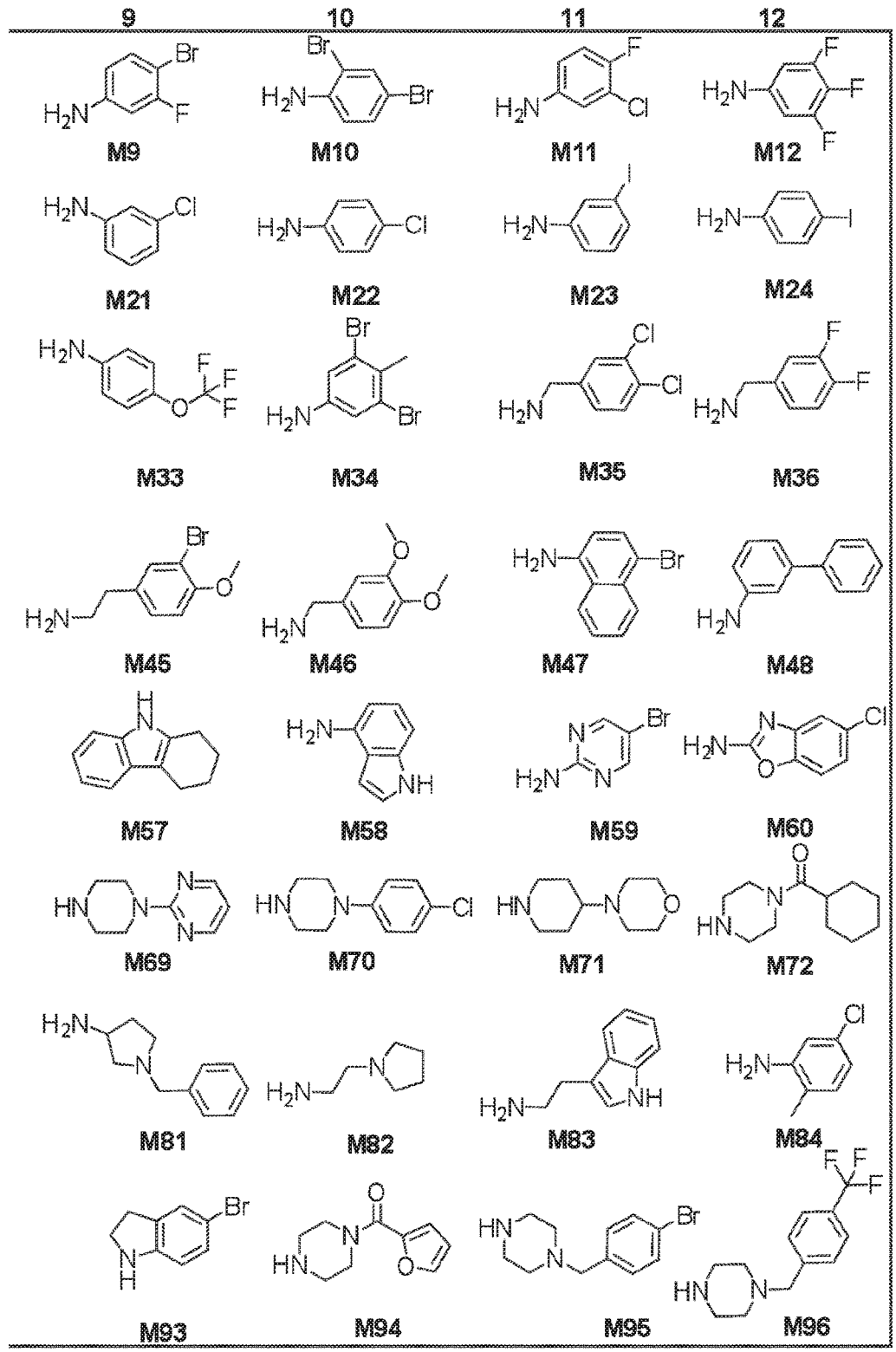
Figure 25B:
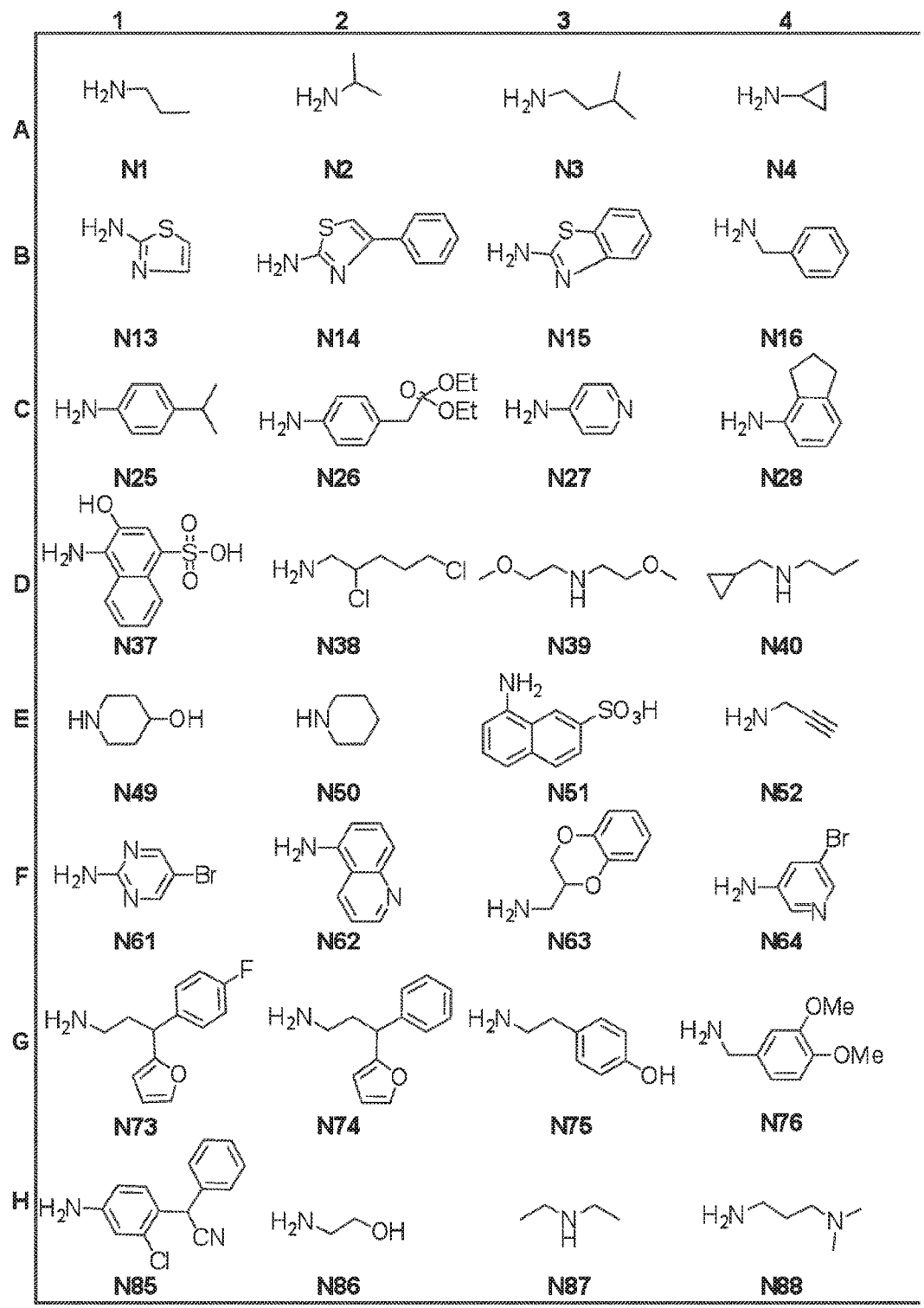
Figure 25B:
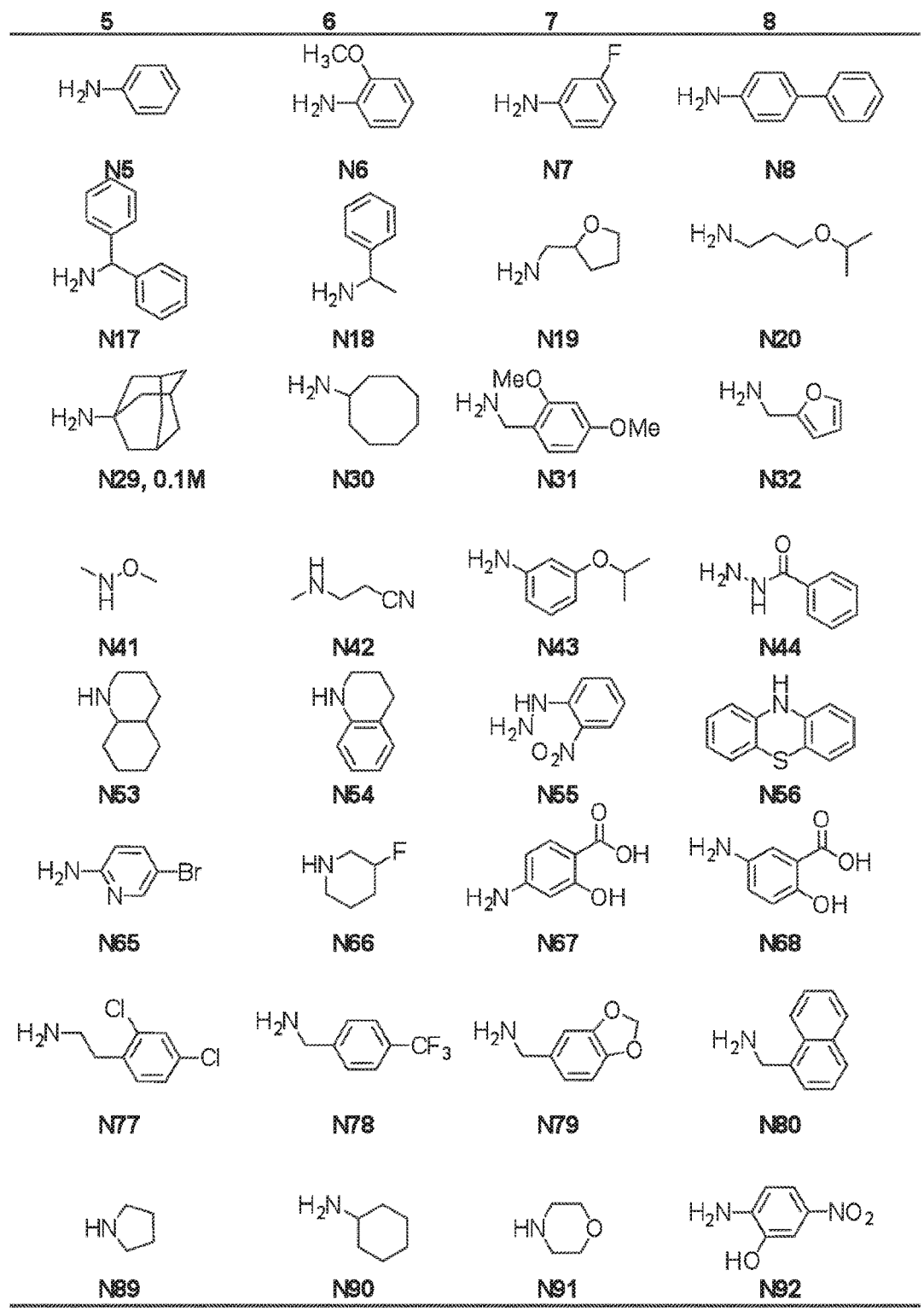
Figure 25B:
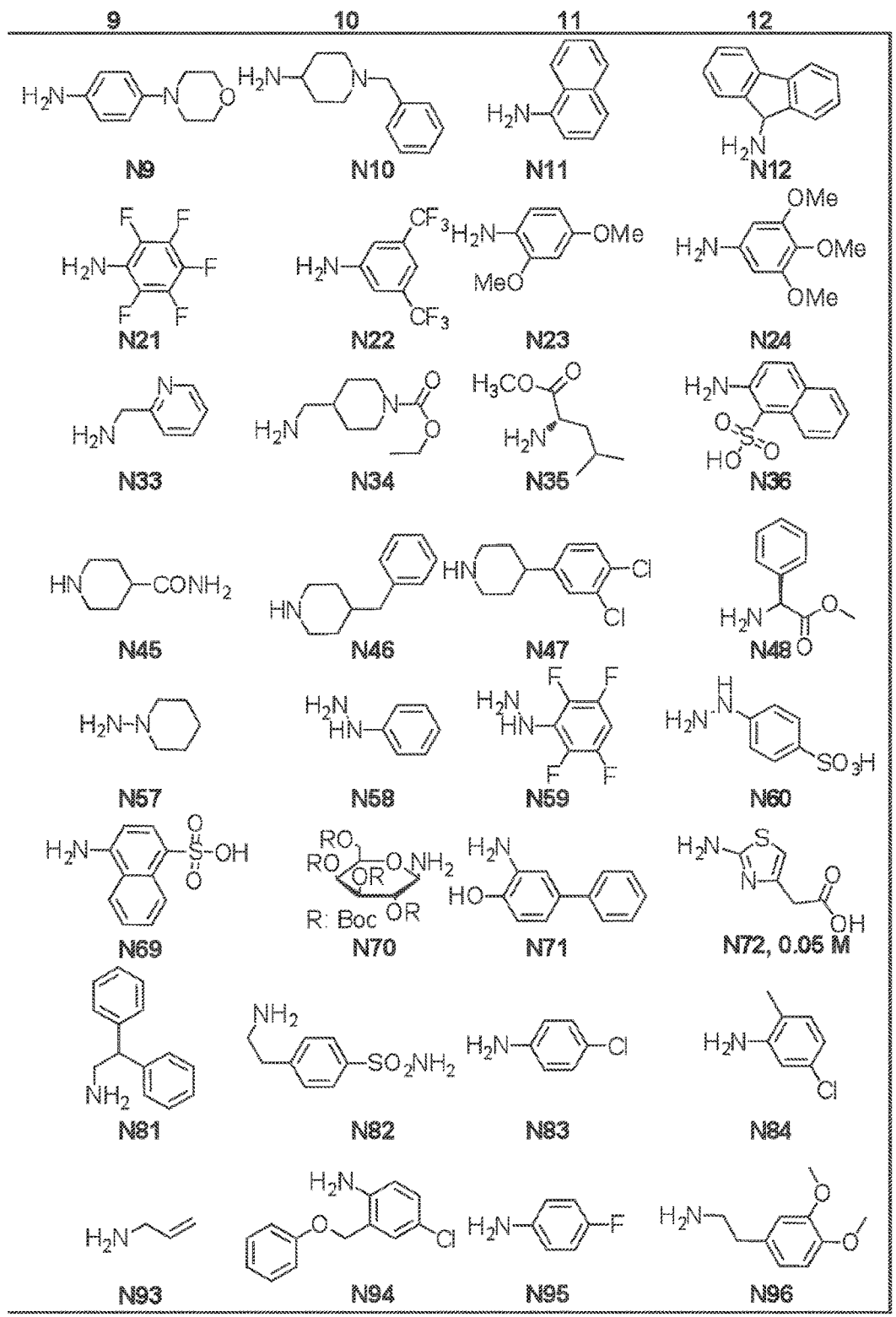

As a proof-of-concept, 4 focused libraries were designed, in which a benzene ring was chosen as the linker, and amide bond formation served as a vehicle for structural diversification (FIG. 24B). In practice, Lib-1 to Lib-4 were synthesized by coupling the available carboxylic acids on the oxalyl moiety (FIG. 24B) with a set of 192 amines that differ in size, charge, lipophilicity, polarity, solubility, and drug-like properties (FIGS. 25A & 25B). Lib-1 and Lib-2 differed at which position on the benzene ring the oxalic acid is attached to, while Lib-3 and Lib-4 were designed to explore flexibility on either side of the benzene linker. The libraries were assembled directly on 96-well plates by standard HBTU amide coupling chemistry. The quality of the libraries was ensured by randomly analyzing multiple wells from each plate by LC-MS, indicating that the reactions went equally well to afford products in excellent yields (70-80%). Thus, a total of 768 compounds incorporating the novel pTyr mimetic SPAA were obtained with molecular weights ranging from 400 to 700. The libraries were screened at both ~10 and ~1 μM against SHP2 in order to shorten the list of actives.

The top 5 hits (compounds 2 to 6, FIG. 24C) identified from the screen were re-synthesized, purified, and their $IC_{50}$ values for SHP2 were determined. As shown in Table 20, although precursors Lib-1 to Lib-4 showed no inhibitory activity against SHP2 at 50 μM, compounds 2 to 6 exhibited $IC_{50}$ in the range of 0.73-2.33 μM, which are 7-23 fold more potent than that of cefsulodin. The marked improvement could be explained by the fact that Lib-1 to Lib-4 lack part C, the terminal diversity element, which likely interact with residues in the vicinity of the active site. This large difference is also consistent with the finding that sulbenicillin exhibits no activity against SHP2 (FIG. 14), likely due to the absence of part C as compared to cefsulodin. Interestingly, compounds 2 to 6 are all from Lib-1, with the oxalic acid handle located at the para position of the benzene linker. In addition, compounds 2 to 6 have either biaryl or single aryl group with bulky substituents at the terminal position, indicating a clear preference for hydrophobic moieties in part C. This conclusion is supported by the substantial loss of activity when one of the aromatic rings is removed from compound 5 (see compound 7 in FIG. 24C and Table 20). Selectivity profiling against the same panel of protein phosphatases showed that compounds 2 and 4 are at least 4- and 8-fold more effective in inhibiting SHP2 against all PTPs tested (Table 18). Furthermore, compounds 2 to 6 also exhibited much greater aqueous stability than cefsulodin (data not shown).

TABLE 20

Inhibitory activities of SPAA-based compounds against SHP2

| $IC_{50}$ (μM) | SHP2 |
|---|---|
| Lib-1 | >50 |
| Lib-2 | >50 |
| Lib-3 | >50 |
| Lib-4 | >50 |
| 2 | 1.51 ± 0.06 |
| 3 | 0.90 ± 0.10 |
| 4 | 0.73 ± 0.02 |
| 5 | 1.36 ± 0.04 |
| 6 | 2.33 ± 0.04 |
| 7 | >50 |

SPAA-Based SHP2 Inhibitors Block Cancer Cell Growth and SHP2-Mediated Signaling.

Figure 26A:
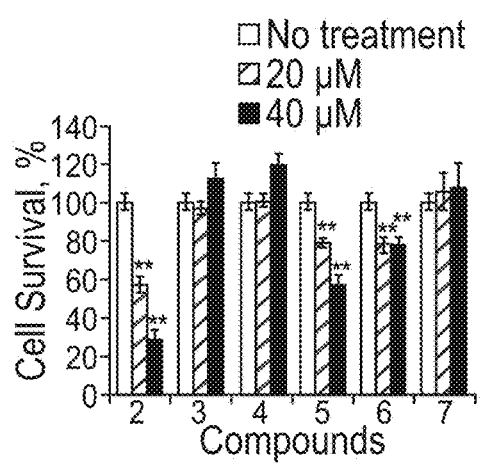
FIGS. 26A-26E depict cellular activity of SPAA-based SHP2 inhibitors.
Figure 26B:
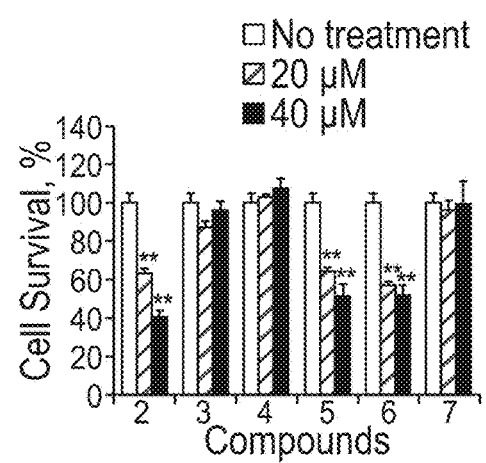

SHP2 has been recognized as a proto-oncogene, thus small molecule SHP2 inhibitors have potential to become new anti-cancer agents. It was previously shown that SHP2 is required for the growth of non-small cell lung cancer (NSCLC) cell line H1975, which is resistant to EGF receptor inhibitor treatment and harbors secondary gatekeeper mutations in the EGF receptor. Knockdown or pharmacological inhibition of SHP2 blocked H1975 cell proliferation by attenuation of EGF induced ERK1/2 activation. Hence, the cellular efficacy of the SPAA-based SHP2 inhibitors in this system were evaluated. As shown in FIG. 26A, compound 2, 5, 6 were able to reduce H1975 cell proliferation in a dose dependent manner, while compound 7 was ineffective as expected, given that it has no inhibition against SHP2 at 50 μM. In contrast, compounds 3 and 4 had no significant effect on H1975 cell proliferation, likely due to inefficient cell penetration. Similar phenomenon was also observed with human breast cancer cell line MDA-MB-231 (FIG. 26B). Thus, compound 2 appeared to be the most efficacious among this series, and it was selected for further mechanistic study.

Figure 26C:
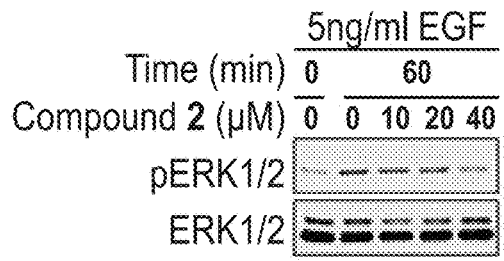
Figure 26D:
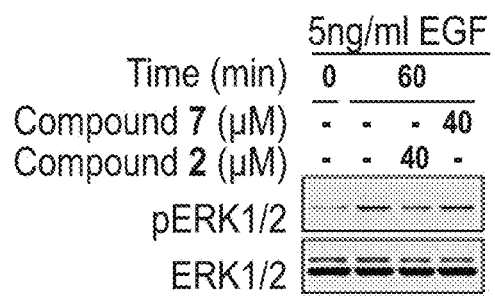

Given the requirement of SHP2 activity for EGF induced Ras-ERK1/2 pathway activation, the cellular effect of compound 2 was assessed on EGF-induced ERK1/2 activation in H1975 cells. Treatment of H1975 cells with compound 2 reduced EGF-mediated ERK1/2 phosphorylation in a dose-dependent manner, while a structurally related inactive compound 7 ($IC_{50}$>50 μM for SHP2) had no appreciable effect on ERK1/2 phosphorylation (FIGS. 26C & 26D). These results are consistent with the observations from the MTT assay that compound 2 dose dependently inhibited H1975 and MDA-MB-231 cell growth while compound 7 did not (FIGS. 26A & 26B).

Figure 26E:

To provide further evidence that compound 2 blocks cell signaling through SHP2 inhibition, compound 2 was analyzed to see if it had any effect on PMA (phorbol 12-myristate 13-acetate)-induced ERK1/2 activation, which does not require SHP2, but instead involves activation of protein kinase C and Raf in a Ras-independent manner. Thus, in this Example, SHP2 inhibitors are not expected to impact PMA-induced ERK1/2 phosphorylation. Indeed, compound 2 had no effect on PMA-induced ERK1/2 phosphorylation (FIG. 26E).

Figure 27A:
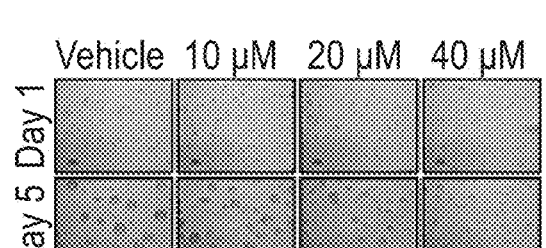
FIGS. 27A & 27B depict the effect of compound 2 on inhibiting ERK1/2 activation and growth of ErbB2+ breast cancer cells in a 3D Matrigel environment.
Figure 27B:
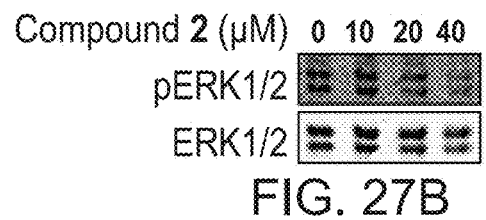

Finally, the effect of SHP2 inhibition by compound 2 was evaluated on the growth of SKBR3 cells in Matrigel. SKBR3 cells are an ERB2 positive breast cancer cell line that when grown in Matrigel more accurately reflect the features of human tumors than when grown on plastic. These cells through upregulation of ERB2 strongly activate Ras, which promotes ERK1/2 signaling when grown in Matrigel. As shown in FIGS. 27A & 27B, treatment with 20 μM of compound 2 resulted in a partial inhibition of ERK1/2 and cell growth, while at 40 μM of compound 2, ERK1/2 activity was barely detectable and cell growth was almost completely absent. Taken together, the results showed that compound 2 can specifically inhibit EGF mediated ERK1/2 activation and the growth of H1975 lung cancer cells, MDA-MB-231 and ErbB2 positive SKBR3 breast cancer cells.

CONCLUSION

Despite considerable drug discovery efforts devoted to the PTP target class, the task of obtaining selective and cell permeable PTP inhibitors remains highly challenging. As a result, few PTP inhibitors have progressed to the clinic. In the present disclosure, a novel drug repurposing strategy for the discovery of PTP inhibitors with more drug-like properties is disclosed. In contrast to the prevailing approach to drug repurposing, which entails identifying new uses for existing drugs, the present disclosure illustrates another path for drug repurposing, namely by identifying a successful pharmacophore from an existing drug for further refinement and design. Since drugs used in the clinic already possess established pharmacokinetic properties and clinical efficacies, the present disclosure identified useful scaffolds from known drugs as starting points for the design of SHP2 inhibitors with improved pharmacological properties. By screening a large FDA-approved drug collection, cefsulodin, a third generation D-lactam cephalosporin antibiotic, was found to exhibit SHP2 inhibitory activity. Structural and molecular modeling analyses identify SPAA as a novel nonhydrolyzable pTyr mimetic, which anchors cefsulodin to SHP2 active site, while interactions of the isonicotinamide tail with residues in the $\beta_5$-$\beta_6$ loop enhances cefsulodin's SHP2 binding potency and selectivity. To remove the chemical liability associated with cefsulodin and to transform cefsulodin into more potent and selective SHP2 inhibitors, a structure-guided and SPAA fragment-based approach that targets both the SHP2 active site as well as its surrounding peripheral pockets was employed. This led to the identification of several SPAA-based SHP2 inhibitors with $IC_{50}$ in the low to sub-micromolar range and several-fold of selectivity against a large panel of mammalian PTPs. Importantly, these SHP2 inhibitors block EGF stimulated ERK1/2 activation and exhibit excellent anti-proliferative activity in H1975 non-small cell lung cancer, as well as MDA-MB-231 and SKBR3 breast cancer cells, demonstrating the utility of drug repurposing for the development of PTP inhibitors with more favorable pharmacological properties. Given the obligatory role of SHP2 in growth factor receptor mediated signaling, inhibitors of SHP2 will most likely have widespread utility in cancer treatment.

Example 10

Inhibition of HePTP and LYP.

Several compounds in the SPAA based library described herein (for example, L319-11-M68, L319-13-M68, and L319-16) have been identified as effective inhibitors of HePTP and LYP (Tables 7 and 21).

TABLE 21

$IC_{50}$ values of HePTP and LYP inhibitors against a panel of PTPs.

| $IC_{50}$, µM | HePTP | LYP | LMWPTP | SHP2 |
|---|---|---|---|---|
| L319-06-M68 | 22 | >100 | >100 | >100 |
| L319-07-M68 | 11 | >100 | >100 | >100 |
| L319-08-N58 | 16 | 9.9 | 11 | 7.28 |
| L319-11-M68 | 3.2 | 7.6 | >100 | >100 |
| L319-12-M68 | 3.9 | 7.43 | 21 | >100 |
| L319-13-M68 | 4.3 | 10 | 27 | >100 |
| L319-14-M50 | 25 | 23 | 28.8 | 24 |
| L319-14-M68 | 4.5 | 8.3 | >100 | >100 |
| L319-14-N03 | 24 | 11.6 | >100 | 74 |
| L319-16-M47 | 21 | 22 | 37 | 24 |
| L319-16-M60 | 13 | 15 | 18 | 12 |
| L319-16-M93 | 7.6 | 16 | 24 | 16 |
| L319-16-N55 | 43 | 35 | 90 | 82 |
| L319-16-N58 | 20 | 20 | 32 | 22 |
| L319-14 | 25 | 11.48 | >100 | 79 |
| L319-15 | 21 | 7.36 | >100 | 70 |
| L319-16 | 11 | 5.19 | >100 | 25 |
| L319-Br1-N15 | 0.2 | NA | NA | 13.2 |
| L319-Br1-N47 | 26.0 | NA | NA | 22.8 |
| L319-Br1-N76 | 21.7 | NA | NA | 9.9 |

Example 11

Cellular Studies of mPTPB Inhibitor L319N53.

Figure 28:
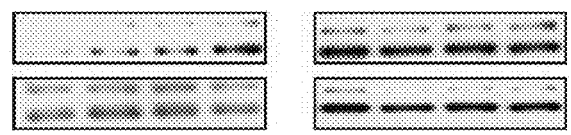
FIG. 28 is a Western Blot showing the in vivo efficiency of L319N53 in blocking mPTPB activity as analyzed in Example 11.

L319N53 was evaluated in cells for its in vivo efficacy in mPTPB inhibition. Previously, mPTPB has been shown to block IFN-γ induced Erk1/2 activation in macrophage cells, while mPTPB inhibitors can rescue this process (Zhou et al, Proc. Natl. Acad. Sci. USA 2010, 107, 4573-4578). As shown in FIG. 28, L319N53 increased Erk1/2 phosphorylation in mPTPB transfected Raw264.7 cells at concentrations of 8 nM, 16 nM, and 32 nM in a dose dependent manner. In contrast, L319N53 has no effect on Erk1/2 phosphorylation in vector cells. These results indicate an in vivo activity and specificity of L319N53 to inhibit mPTPB.

Example 12

Cellular Studies of LMWPTP Inhibitor L335N15.

L335N15 was tested for its efficacy in blocking LMWPTP's activity in vivo. LMWPTP is a negative regulator of insulin-mediated mitogenic and metabolic signaling (for example, the IR-PI3K-Akt pathway), although its precise role in regulating insulin action remains unknown. ASO-targeting LMWPTP in hepatocyte and liver cells was able to enhance the phosphorylation and activity of key insulin signaling intermediates, including insulin receptor subunit and Akt in response to insulin stimulation.

Figure 29A:
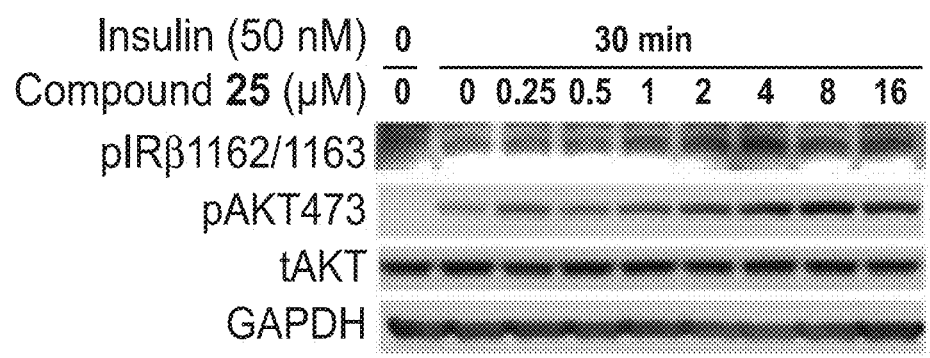
FIGS. 29A-29C show the in vivo efficiency of L335N15 in sensitizing the insulin signaling pathway in HepG2 cells as analyzed in Example 12.
Figure 29B:
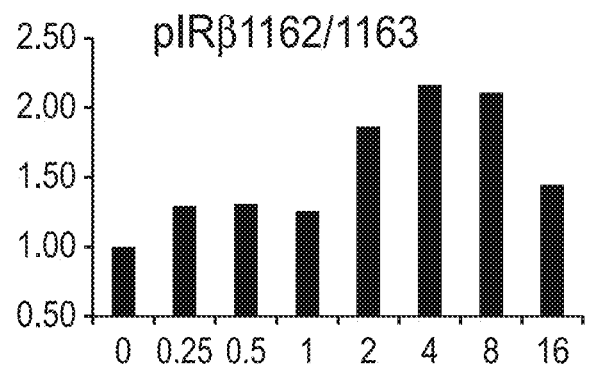
Figure 29C:
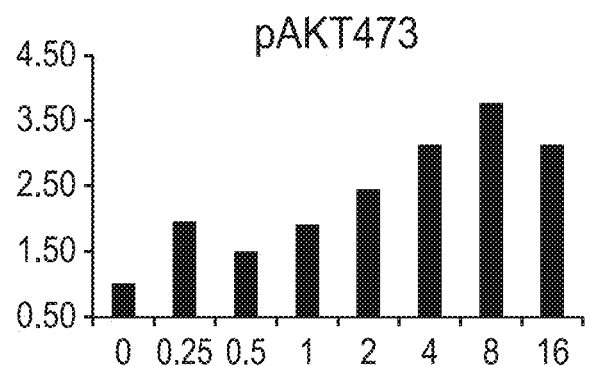

To assess the effects of L335N15 in insulin signaling pathway, HepG2 cells were pretreated with L335N15 for 1 hour and were subsequently stimulated with 5 nM insulin for 5 minutes. As shown in FIGS. 29A-29C, L335N15 enhanced IR Tyr1162/1163 phosphorylation in a dose-dependent fashion relative to the vehicle DMSO. Consistent with IR activation, downstream Akt phosphorylation (Ser473) was increased. These results, coupled with the observation that L335N15 at 100 µM did not inhibit 24 other PTPs, especially those involved in insulin signaling (PTP1B, TcPTP, Meg2, SHP2, PTPα, PTPε, LAR), suggests that the enhanced insulin signaling is likely due to the specific, in vivo inhibition of LMWPTP by L335N15. Accordingly, LMWPTP inhibitors such as L335N15 described herein can be used to develop agents for the treatment of type 2 diabetes and insulin resistance.

In conclusion, novel sulfonic acid based pTyr mimetic compounds identified in the present disclosure are effective inhibitors of several distinct PTPs, including mpPTPA, mPTPB, LMWPTP, Laforin, SHP2, HePTP, LYP, with unprecedented potency and selectivity. Through a medicinal chemistry effort described herein, specific inhibitors of either LMWPTP or Laforin have been provided. Importantly, the compounds identified in this disclosure exhibited in vivo activity in increasing Erk1/2 phosphorylation (for example, L319N53 inhibition of mPTPB) and in sensitizing insulin signaling pathway (for example, L335N15 inhibition of LMWPTP). These compounds allow for the development of pharmaceutical formulations for treating diseases associated with abnormal PTP activities, such as TB, cancer, diabetes, and obesity.

What is claimed is:

1. A compound of Formula 1b:

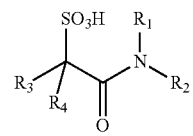

Formula 1b or a therapeutically suitable salt thereof, wherein:
$R_1$ is hydrogen;
$R_2$ is aryl substituted with —$(CH_2)_s$—NH—CO—$R_z$;
s is 0-4;
$R_z$ is aryl or furan optionally substituted with one or more substituent selected from the group consisting of $C_1$-$C_4$ alkyl, benzoyl, benzyl, benzyloxy (—OBn), phenyl, halogen, 1H-benzimidazole-2-yl, and 2-thiophenyl;
or $R_1$, $R_2$, and the N atom taken together form pyridine, piperidine, octahydroquinoline, decahydroquinoline, quinoline, or indoline;
$R_3$ is hydrogen or halogen; and
$R_4$ is hydrogen or aryl, the aryl optionally substituted with one or more substituents selected from the group consisting of halogen, $C_1$-$C_4$ alkyl, $C_1$-$C_4$ alkoxy, phenyl, nitro, cyano, and —$COCF_3$.

2. A compound of Formula 3:

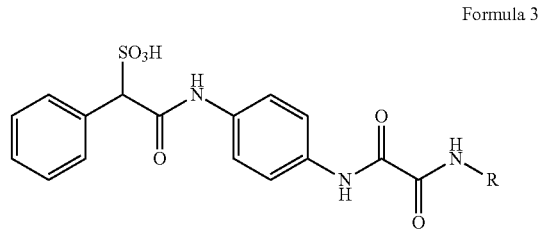

Formula 3 or a therapeutically suitable salt thereof, wherein R is phenyl, 4H-pyrazole, or 4,5-dihydro-1H-pyrazole optionally substituted with one or more substituents selected from the group consisting of $C_1$-$C_4$ alkyl, halogen, 1-imidazolyl, benzyl, benzyloxy, phenyl, 1H-benzo[d]imidazole, bromobenzene, and 2-thiophenyl.

3. The compound of claim 2, wherein R is selected from the group consisting of

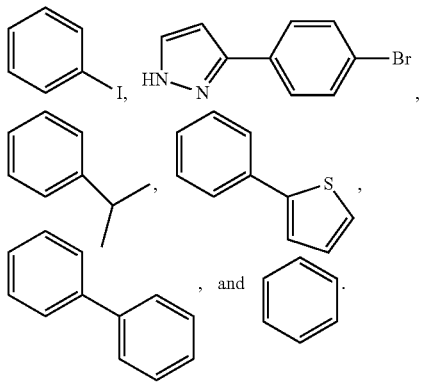

4. A method of inhibiting Src homology 2 tyrosine phosphatase (SHP2) in a subject, comprising administering to the subject a therapeutically effective amount of the compound of claim 1, wherein the subject has tuberculosis or Lafora disease.

5. A pharmaceutical composition comprising a compound of claim 1 and a pharmaceutically acceptable carrier.

6. A method of inhibiting Src homology 2 tyrosine phosphatase (SHP2) in a subject, comprising administering to the subject a therapeutically effective amount of the compound of claim 2, wherein the subject has tuberculosis or Lafora disease.

7. A pharmaceutical composition comprising a compound of claim 2 and a pharmaceutically acceptable carrier.

8. A method of inhibiting Src homology 2 tyrosine phosphatase (SHP2) in a subject, comprising administering to the subject a therapeutically effective amount of the compound of claim 3, wherein the subject has tuberculosis or Lafora disease.

9. A pharmaceutical composition comprising a compound of claim 3 and a pharmaceutically acceptable carrier.

* * * * *